United States Patent
Lee et al.

(10) Patent No.: US 7,714,146 B2
(45) Date of Patent: May 11, 2010

(54) AZULENE-OXINDOLE COMPOUNDS AS MULTIPLE-KINASE INHIBITORS AND USEFUL AS ANTICANCER AGENTS

(75) Inventors: On Lee, Hsinchu (TW); Chrong-Shiong Hwang, Hsinchu (TW); Chih-Hung Chen, Tainan County (TW); Yuan-Jang Tsai, Hsinchu County (TW); Chih-Peng Liu, Hsinchu (TW); Ching-Huai Ko, Changhua County (TW); Hsin-Hsin Shen, Hsinchu (TW); Ling-Mei Wang, Taipei (TW); Kuei-Tai Lai, Taipei (TW); Ying-Chu Shih, Hsinchu County (TW); Ting-Shou Chen, Taoyuan County (TW); Yen-Chun Chen, Hsinchu (TW); Lain-Tze Lee, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/980,767

(22) Filed: Oct. 31, 2007

(65) Prior Publication Data
US 2008/0125590 A1    May 29, 2008

Related U.S. Application Data

(60) Provisional application No. 60/855,781, filed on Nov. 1, 2006.

(51) Int. Cl.
*C07D 209/34* (2006.01)

(52) U.S. Cl. .................... 548/486; 544/373; 549/52; 549/466

(58) Field of Classification Search ............... 544/373; 548/486; 549/52, 466
See application file for complete search history.

(56) References Cited

FOREIGN PATENT DOCUMENTS

WO    WO-97/46551 A1    12/1997
WO    WO-03/074497 A1    9/2003

OTHER PUBLICATIONS

Database Registry Chemical Abstracts Service, Columbus, OH, retrieved from STN Database accession No. RN 259089-82-2, XP002524720, Mar. 13, 2000.

*Primary Examiner*—Kamal A Saeed
*Assistant Examiner*—Valerie Rodriguez-Garcia
(74) *Attorney, Agent, or Firm*—Birch, Stewart, Kolasch & Birch, LLP

(57) ABSTRACT

The invention is related to novel azulene-oxindole compounds having formula (I) shown below, wherein one of $R_1$, $R_2$ and $R_3$ represents a moiety of formula (II), each of $A_1$ and $A_2$ independently is nitrogen, oxygen or sulfur, each of the others of $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is as recited in the specification. The novel compound potentially inhibits multiple kinases and thus can be used to treat some disease like cancer or inflammatory.

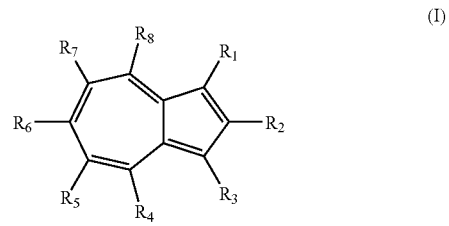

(I)

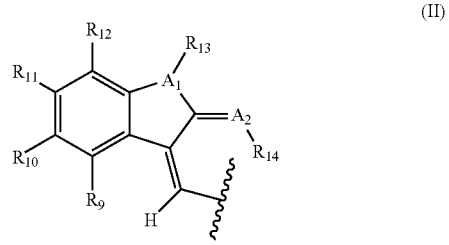

(II)

8 Claims, No Drawings

AZULENE-OXINDOLE COMPOUNDS AS MULTIPLE-KINASE INHIBITORS AND USEFUL AS ANTICANCER AGENTS

BACKGROUND OF THE INVENTION

1. Field of the Invention

The invention relates to a medicine, and in particular to azulene compounds which modulate the protein kinases (PKs) activity.

2. Description of the Related Art

Protein kinases (PKs) are enzymes which catalyze the phosphorylation of specific tyrosine or serine/threonine residues in cellular proteins. The PKs mediate cellular signal transduction in regulating cellular function—proliferation, differentiation, growth, cell cycle, cell metabolism, survival/apoptosis, DNA damage repair, cell motility, and response to the microenvironment. Disregulated PKs activity is a frequent cause of disease, particularly in cancers, where kinases regulate many aspects that control cell growth, movement and death.

The PKs can be divided into two classes: the protein tyrosine kinases (PTKs) and the serine/threonine kinases (STKs). PTKs, which catalyze the transfer of the γ phosphate of ATP to tyrosine residues of protein substrates is one of the key covalent modifications that occurs in multi-cellular organisms as a result of intercellular communication during embryogenesis and maintenance of adult tissues. Phosphorylation of tyrosine residues modulates enzymatic activity of PTKs and the recruitment of downstream signaling proteins. Two classes of PTKs are present in cells: the transmembrane receptor PTKs and the nonreceptor PTKs. PTKs are critical components of cellular signaling pathways, their catalytic activity is strictly regulated. Unregulated activation of these enzymes, through mechanisms such as point mutations or over-expression, can lead to various forms of cancer as well as benign proliferative conditions. The importance of PTKs in health and disease is further underscored by the existence of aberrations in PTK signaling occurring in inflammatory diseases and diabetes. Of the 91 protein tyrosine kinases identified thus far, 59 are receptor tyrosine kinases and 32 are non-receptor tyrosine kinases. The growth factor receptors with PTK activity are known as receptor tyrosine kinases ("RTKs"). They comprise a large family of transmembrane receptors with diverse biological activity. The intracellular kinase domains of RTKs can be divided into two classes: those containing a stretch of amino acids separating the kinase domain and those in which the kinase domain is continuous. Activation of the kinase is achieved by ligand binding to the extracellular domain, which induces dimerization or oligomerization of the receptors. Receptors thus activated are able to autophosphorylate tyrosine residues outside the catalytic domain via cross-phosphorylation. The results of this auto-phosphorylation are stabilization of the active receptor conformation and the creation of phosphotyrosine docking sites for proteins which transduce signals within the cell. Signaling proteins which bind to the intracellular domain of receptor tyrosine kinases in a phosphotyrosine-dependent manner include RasGAP, PI3-kinase, phospholipase C, phosphotyrosine phosphatase SHP and adaptor proteins such as Shc, Grb2 and Crk.

The EGFR, epidermal growth factor receptor, belongs to a family of receptor tyrosine kinases in mammals which is composed of four members: EGFR (ErB1), ErB2, ErB3, and ErB4. EGFR is an 1186 amino acid residue transmembrane glycoprotein. It consists of an extracellular ligand binding domain, an intracellular tyrosine kinase domain, and a COOH terminal region that contains autophosphorylation sites. The binding of specific ligands, such as EGF, transforming growth factor-beta, betacellulin, heparin-binding EGF, epiregulin, or amphiregulin, results in phosphorylation of multiple tyrosine residues in the COOH-terminal tail, triggering the cellular signaling pathway that regulates fundamental cellular processes such as proliferation, migration, differentiation and survival. EGFR is over expressed in many types of tumor cells, such as bladder, lung, gastric, breast, brain, head & neck, cervix, ovary, endometrium, etc. Abnormally high EGFR activity can be characteristic of non-small-cell lung cancers, breast cancers, ovarian cancers, bladder cancers, prostate cancers, salivary gland cancers, pancreatic cancers, endometrial cancers, colorectal cancers, kidney cancers, head and neck cancers, and glioblastoma multiforme. A tyrosine kinase inhibitor targeted to EGFR can be used for the treatment of cancers having abnormally high EGFR kinase activity and EFGR kinase disorder diseases.

One of RTK subfamily is referred to as the platelet derived growth factor receptor ("PDGFR") group, which includes PDGFR.alpha., PDGFR.beta., CSFIR, c-KIT and c-fms. These receptors consist of glycosylated extracellular domains composed of variable numbers of immunoglobin-like loops and an intracellular domain wherein the tyrosine kinase domain is interrupted by unrelated amino acid sequences. PDGFR signals induce expression of pro-angiogenic signals (including VEGF) in endothelial cells, further stimulating tumor angiogenesis. The PDGFR signaling pathway may play an important role in cell proliferation, cell migration, and angiogenesis, and may mediate the high interstitial fluid pressure of tumors.

Another group which, because of its similarity to the PDGFR subfamily, is sometimes subsumed into the later group is the fetus liver kinase ("flk") receptor subfamily. This group is believed to be made up of kinase insert domain-receptor fetal liver kinase-1 (KDR/FLK-1, VEGF-R2), flk-1R, flk-4 and fms-like tyrosine kinase 1 (flt-1). Abnormally high PDGFR activity can be characteristic of gastrointestinal stromal tumor, small cell lung cancer, glioblastoma multiforme, and prostate cancer. A tyrosine kinase inhibitor targeted to PDGFR can be used for the treatment of cancers having abnormally high PDGFR kinase activity and PDGFR kinase disorder diseases.

FLT-3 (FMS-like tyrosine kinase 3) is a class III RTK structurally related to PDGFR, and colony stimulating factor 1 (CSF1). These RTK contain five immunoglobulin-like domains in the extracellular region and an intracellular tyrosine kinase domain split in two by a specific hydrophilic insertion (kinase insert). FLT-3 expression was described on bone marrow CD34-positive cells, corresponding to multipotential, myeloid and B-lymphoid progenitor cells, and on monocytic cells. FLT3 expression is restricted to cells of the fetal liver expressing high levels of CD34. FLT3 receptor function can be defined by the activity of its ligand (FL). FL is an early acting factor and supports the survival, proliferation and differentiation of primitive hemopoietic progenitor cells. Ligand binding to FLT3 promotes receptor dimerization and subsequent signalling through phosphorylation of multiple cytoplasmatic proteins, including SHC, SHP-2, SHIP, Cb1, Cb1-b, Gab1 and Gab2, as well as the activation of several downstream signalling pathways, such as the Ras/Raf/MAPK and PI3 kinase cascades. Internal tandem duplications (ITD) and/or insertions and, rarely, deletions in the FLT3-gene are implicated in 20-25% of all acute myeloid leukemias (AML). The duplicated sequence belongs to exon 11 but sometimes involves intron 11 and exon 12. The most frequently used nomenclature is FLT3-ITD. Because of the very heterogeneous molecular structure the term FLT3-LM (length mutation) seems to be more adequate. It was also described to be involved in 5-10% myelodysplastic syndromes (MDS) refractory anemia with excess of blasts (RAEB 1 and RAEB 2) and rare cases with acute lymphoblastic leukemia (ALL). A tyrosine kinase inhibitor targeted to FLT-3 can be used for the treatment of cancers having abnormally high FLT-3 kinase activity and FLT3 kinase disorder diseases.

C-KIT, SCFR (Stem Cell Factor Receptor), is known as type III receptor tyrosine kinase, structurally related to CSF-1R, PDGFR, and FLT-3, containing an extracellular domains with 5 Ig-like loops, a highly hydrophobic transmembrane domain, and an intracellular domain with tyrosine kinase activity split by a kinase insert (KI) in an ATP-binding region and in the phosphotransferase domain. C-Kit is expressed on the cell plasma membrane in the hematopoietic stem cells, mast cells, melanocytes, and germ-cell lineages. SCF/MGF receptor with PTK activity, binding of ligand (SCF) induces receptor dimerization, autophosphorylation and signal transduction via molecules containing SH2-domains. With the abnormal activity expression, mast cell hyperplasia in the bone marrow, liver, spleen, lymph nodes, gastrointestinal tract and skin, gain of function mutations are detected in most patients. It is recognized as clinical features of malignant hematopoietic cell growth are influenced by the time, the location of c-kit mutative events, and the number of associated lesions. A tyrosine kinase inhibitor targeted to c-Kit can be used for the treatment of cancers having abnormally high c-Kit kinase activity and c-Kit kinase disorder diseases.

Another member of the tyrosine kinase growth factor receptor family is the vascular endothelial growth factor receptor (VEGFR) subgroup. VEGFR is a dimeric glycoprotein similar to PDGFR but has different biological functions and target cell specificity in vivo. In particular, VEGFR is presently thought to play an essential role is vasculogenesis and angiogenesis. Angiogenesis is essential for tumor growth and survival. There are 3 distinct VEGF receptors—VEGFR-1, -2, and -3. Each of them contributes separately to the angiogenic process. VEGFR-1 is thought to play a role in regulating VEGF binding to VEGFR-2 during angiogenesis. VEGFR-2 (KDR) stimulates the proliferation, migration, and survival of endothelial cells during angiogenesis and is recognized as a critical VEGF receptor for angiogenesis. VEGFR-3 stimulates the proliferation, migration, and survival of endothelial cells during lymphangiogenesis, which in turn facilitates metastases. Despite these seemingly distinct roles, all VEGFRs overlap to some degree in their function, leading to significant redundancy. Therefore, inhibition of all identified VEGF receptors may ensure more complete inhibition of angiogenesis. A tyrosine kinase inhibitor targeted to VEGFR can be used for the treatment of solid tumors and vascular disorder diseases.

c-Met (hepatocyte growth factor receptor), is the high affinity receptor for HGF/SF, a multifunctional cytokine. Upon ligand binding, MET dimerizes and transphosphorylates tyrosine residues in the C-terminal domain, which then interacts with members of a variety of signaling pathways. These include Grb-2 associated binder 1, phosphoinositide 3' kinase and c-Src. Under physiological conditions, MET-HGF/SF signaling has been shown to affect a wide range of biological activities depending on the cell target. These activities vary from cell proliferation (mitogenesis) to cellular shaping (morphogenesis) and motility (motogenesis). The coordination of these diverse activities constitutes a genetic program of invasive growth that allows branched morphogenesis (the formation of epithelial tubular structures), myoblast migration and neurite branching. MET/HGF cell targets comprise epithelial and mesenchymal cells, hematopoietic cells, myoblasts, spinal motor neurons. MET-HGF/SF signaling is also essential for normal development: mouse embryos carrying null mutations in both HGF alleles die in midgestation and show impaired liver formation. MET and its ligand hepatocyte growth factor/scatter factor (HGF/SF) are expressed in numerous tissues although predominantly in cells of epithelial and mesenchymal origin, respectively. MET is amplified and overexpressed in many types of tumors, including tumors of the kidney, thyroid, pancreas and osteosarcoma. A tyrosine kinase inhibitor targeted to c-Met can be used for the treatment of cancers having abnormally high c-Met kinase activity and c-Met kinase disorder diseases.

RET is a tyrosine kinase receptor whose ligands are neurotrophic factors of the glial-cell line derived neurotrophic factor (GDNF) family, including GDNF, neurturin, artemin and persefin. RET activation is mediated via different glycosyl phosphatidylinositol-linked GRF receptors. 3 main isoforms of RET is detected in human, such as long isoform (RET51): 1114 amino acids, middle isoform (RET 43): 1106 amino acids and short isoform (RET 9): 1072 amino acids. RET is mainly expressed in tumors of neural crest origin: medullary thyroid carcinoma, pheochromocytoma and neuroblastoma. In human embryos, RET is expressed in a cranial population of neural crest cells, and in the developing nervous and urogenital systems. RET expression is found in several crest-derived cell lines, spleen, thymus, lymph nodes, salivary glands, spermatogonia, and recently in normal thyroid tissue, thyroid adenoma and both papillary and follicular thyroid cell neoplasias. A tyrosine kinase inhibitor targeted to RET can be used for the treatment of cancers having abnormally high RET kinase activity and RET kinase disorder diseases.

c-ABL (v-abl Abelson murine leukemia viral oncogene homolog) exhibit a permanent nuclear and cytoplasmic shuttling activity, driven by 3 nuclear localization signals (NLS) and a single nuclear export signal (NES) close to the C-terminal region. BCR/ABL has a cytoplasmic localization role and all three BCR-ABL fusion proteins have been shown to exhibit oncogenic potential. All three hybrid proteins have increased protein kinase activity compared to ABL: 3BP1 (binding protein) binds normal ABL on SH3 domain, which prevents SH1 activation. Nuclear and cytoplasmic ABL may have different functions. 1—Nuclear c-ABL plays a major role in the regulation of cell death after DNA damage. All DNA damage inducing agents activate nuclear c-ABL kinase in a ATM-dependent manner and in the presence of the p53-homolog p73 protein. The latter is physically associated with c-ABL after DNA damage through the SH3 domain of c-ABL. DNA damage also activates simultaneously p53 pathway, leading to the activation of Rb which induces growth arrest and protects cells from apoptosis. The exact mechanisms of apoptosis induced by c-ABL are unknown. The nuclear entrapment of BCR-ABL has also been shown to induce apoptosis in leukemic cells. 2—Cytoplasmic c-ABL: possible function in adhesion signalling as an efflux of c-ABL from nucleus to the cytoplasm is found in fibroblasts after adhesion. A tyrosine kinase inhibitor targeted to c-ABL can be used for the treatment of cancers having abnormally high c-ABL kinase activity and c-ABL kinase disorder diseases.

TIE (tyrosine kinase with immunoglobulin-like and EGF-like domains) can be defined into two subgroups. TIE-1 (tyrosine kinase with Ig and EGF homology domains 1) and TIE-2/Tek comprise a receptor tyrosine kinase (RTK) subfamily with unique structural characteristics: two immunoglobulin-like domains flanking three epidermal growth factor (EGF)-like domains and followed by three fibronectin type III-like repeats in the extracellular region and a split tyrosine kinase domain in the cytoplasmic region. These receptors are expressed primarily on endothelial and hematopoietic progenitor cells and play critical roles in angiogenesis, vasculogenesis and hematopoiesis. Human TIE-1 cDNA encodes a 1124 amino acid (aa) residue precursor protein with an 18 residue putative signal peptide, a 727 residue extracellular domain and a 354 residue cytoplasmic domain. Two ligands, angiopoietin-1 (Ang1) and angiopoietin-2 (Ang2), which bind TIE-1 with high affinity, have been identified. Ang2 has been reported to act as an antagonist for Ang1. A tyrosine kinase inhibitor targeted to TIE can be used for the treatment of solid tumors and vascular disorder diseases.

FGFR (fibroblast growth factor receptors) consist of an extracellular ligand domain comprised of three immunoglobulin-like domains, a single transmembrane helix domain, and an intracellular domain with tyrosine kinase activity. The fibroblast growth factors are the largest family of growth factor ligands comprising of 23 members. FGFRs share a similar sequence structure, characterized by three extracellular immunoglobulin-like domains (IgI, IgII, and IgIII), a single-pass transmembrane segment, and a split tyrosine kinase (TK1/TK2) domain. The great majority of pathogenic FGFR mutations are missense, and all confer gain of function to the mutated protein. Some mutations are highly recurrent. The gain-of-function mechanisms identified for FGFR2 mutations are (a) selectively enhanced FGF-binding affinity, (b) illegitimate FGF-binding specificity, (c) FGF-independent covalent dimerization, and (d) ectopic spliceoform expression. These mechanisms account for the dominant inheritance of all the associated phenotypes. A tyrosine kinase inhibitor targeted to FGFR can be used for the treatment of cancers having abnormally high FGFR kinase activity and FGFR kinase disorder diseases.

Insulin-like growth factor 1 (IGF1) was considered a potential candidate for the treatment of heart failure. However, some animal studies and clinical trials have questioned whether elevating IGF1 chronically is beneficial. Secondary effects of increased serum IGF1 levels on other tissues may explain these unfavorable results. The aim of the current study was to examine the role of IGF1 in cardiac myocytes in the absence of secondary effects, and to elucidate downstream signaling pathways and transcriptional regulatory effects of the IGF1 receptor (IGF1R). Activation of the IGF-1 receptor is survival and proliferation in mitosis-competent cells, and growth (hypertrophy) in tissues such as skeletal muscle and cardiac muscle. The IGFR signalling pathway is of critical importance during normal development of mammary gland tissue during pregnancy and lactation. Several growth factors and hormones are involved in this overall process, and IGF-1R is believed to have roles in the differentiation of the cells and a key role in inhibiting apoptosis until weaning is complete. The IGF-1R is implicated in several cancers, most notably breast cancer. It is further implicated in breast cancer by increasing the metastatic potential of the original tumor by inferring the ability to promote vascularisation. A tyrosine kinase inhibitor targeted to IGFR can be used for the treatment of cancers having abnormally high IGFR kinase activity and IGFR kinase disorder diseases.

Kinases such as c-Src, c-Abl, mitogen activated protein (MAP) kinase, phosphotidylinositol-3-kinase (PI3K) AKT, and the epidermal growth factor (EGF) receptor are commonly activated in cancer cells, and are known to contribute to tumorigenesis. Many of these occur in the same signaling pathway—for example, HER-kinase family members (HER1 [EGFR], HER3, and HER4) transmit signals through MAP kinase and PI3 kinase to promote cell proliferation.

PTK disorder disease includes, such as cancer, asarthritis, diabetic retinopathy, restenosis, hepatic cirrhosis, atherosclerosis, angiogensis, glomerulonephritis, diabetic nephropathy, thrombic microangiopathy syndromes, transplant rejection, autoimmune disease, diabetes, and hyperimmune disorders.

Cancers include, without limitation, carcinoma of the bladder, breast, colon, kidney, liver, lung, head and neck, gallbladder, ovary, pancreas, stomach, cervix, thyroid, prostate, skin, hematopoietic tumor of lymphoid lineage (i.e. leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma), hematopoietic tumor of myeloid lineage (i.e. acute myelogenous leukemia, chronic myelogenous leukemia, multiple myelogenous leukemia, myelodysplastic syndrome and promyelocytic leukemia), tumor of mesenchymal origin (i.e. fibrosarcoma and rhabdomyosarcoma), tumor of the central or peripheral nervous system (i.e. astrocytoma, neuroblastoma, glioma and schwannomas), melanoma, seminoma, teratocarcinoma, osteosarcoma, thyroid follicular cancer; and Kaposi's sarcoma.

BRIEF SUMMARY OF THE INVENTION

The invention is based on the discovery that certain azulene compounds are effective in treating cancer by inhibiting the activity of protein kinases or phosphatases.

One embodiment of the invention features azulene compounds of formula (I):

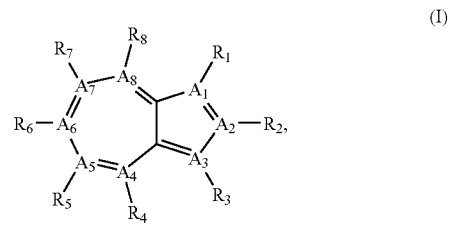

wherein one of $R_1$, $R_2$, $R_3$, $R_4$, $R_5$, $R_6$, $R_7$, and $R_8$ is a moiety of formula (II):

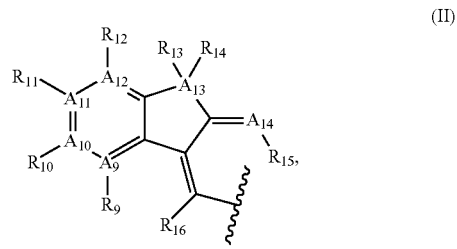

each of $A_1$, $A_2$, $A_3$, $A_4$, $A_5$, $A_6$, $A_7$, $A_8$, $A_9$, $A_{10}$, $A_{11}$, and $A_{12}$, independently, is carbon or nitrogen, provided that at most two of $A_1$, $A_2$, $A_3$, $A_4$, $A_5$, $A_6$, $A_7$, and $A_8$ are nitrogen and that at most two of $A_9$, $A_{10}$, $A_{11}$, and $A_{12}$ are nitrogen, each of $A_{13}$ and $A_{14}$, independently, is carbon, nitrogen, oxygen, or sulfur, each of the others of $R_1$, $R_2$, $R_3$, $R_4$, $R_5$, $R_6$, $R_7$, and $R_8$, independently, is H, halo, $C_1$-$C_2$ alkyl, $C_4$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, $NO_2$, NO, $N_3$, SCN, CN, OCN, OR, OC(O)R, OC(S)R, OC(S)OR, OC(O)SR, OC(S)SR, OC(O)NRR', OC(S)NRR', ONRR', OS(O)R, OS(O)$_2$R, SR, SC(O)R, SC(S)R, SC(S)OR, SC(O)SR, SC(S)SR, SC(O)NRR', SC(S)NRR', S(O)R, S(O)$_2$R, S(O)NRR', S(O)$_2$NRR', S(O)OR, S(O)$_2$OR, NCO, NCS, NRR', N(R)—C(O)R', N(R)—C(O)OR', N(R)—C(S)R', N(R)—C(S)OR', N(C(O)R)—C(O)R', N(R)—S(O)R', N(R)—S(O)OR', N(R)—S(O)$_2$R', N(R)—S(O)$_2$OR', N(R)—OR', N(OR)—C(O)R', N(OR)—C(O)OR', N(OR)—C(S)R', N(OR)—C(S)OR', N(OR)—C(S)SR', N(OR)—S(O)R', N(OR)—S(O)OR', N(OR)—S(O)$_2$R', N(OR)—S(O)$_2$OR', C(O)R, C(O)OR, C(O)NRR', C(O)SR, C(S)R, C(S)OR, C(S)NRR', C(S)SR, C(NR)—R', C(NR)—OR', C(NR)—NR'R", C(NR)—SR', C(NOR)—R', C(NOR)—OR', C(NOR)—NR'R", and C(NOR)—SR', or $R_1$ and $R_2$, $R_2$ and $R_3$, $R_4$ and $R_5$, $R_5$ and $R_6$, $R_6$ and $R_7$, or $R_7$ and $R_8$, together with the atoms to which they are attached, are $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl, provided that each of the others of $R_1$, $R_2$, $R_3$, $R_4$, $R_5$, $R_6$, $R_7$, and $R_8$, independently, is deleted if the atom to which it is attached is nitrogen, and each of $R_9$, $R_{10}$, $R_{11}$, $R_{12}$, $R_{13}$, $R_{14}$, $R_{15}$, and $R_{16}$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, $NO_2$, NO, $N_3$, SCN, CN, OCN, OR, OC(O)R, OC(S)R, OC(S)OR, OC(O)SR, OC(S)SR, OC(O)NRR', OC(S)NRR', ONRR', OS(O)R, OS(O)$_2$R, SR, SC(O)R, SC(S)R, SC(S)OR, SC(O)SR, SC(S)SR, SC(O)NRR', SC(S)NRR', S(O)R, S(O)$_2$R, S(O)NRR', S(O)$_2$NRR', S(O)OR, S(O)$_2$OR, NCO, NCS, NRR', N(R)—C(O)R', N(R)—C(O)OR', N(R)—C(S)R', N(R)—C(S)OR', N(C(O)R)—C(O)R', N(R)—S(O)R', N(R)—S(O)OR', N(R)—S(O)$_2$R', N(R)—S(O)$_2$OR', N(R)—OR', N(OR)—C(O)R', N(OR)—C(O)OR', N(OR)—C(S)R', N(OR)—C(S)OR', N(OR)—C(S)SR', N(OR)—S(O)R', N(OR)—S(O)OR', N(OR)—S(O)$_2$R', N(OR)—S(O)$_2$OR', C(O)R, C(O)OR, C(O)NRR', C(O)SR, C(S)R, C(S)OR, C(S)NRR', C(S)SR, C(NR)—R', C(NR)—OR', C(NR)—NR'R", C(NR)—SR', C(NOR)—R', C(NOR)—OR', C(NOR)—NR'R", and C(NOR)—SR', provided that each of $R_9$, $R_{10}$, $R_{11}$, and $R_{12}$ independently, is deleted if the atom to which it is attached is nitrogen, that one of $R_{13}$ and $R_{14}$ is deleted if the atom to which they are attached is nitrogen, that both of $R_{13}$ and $R_{14}$ are deleted if the atom to which they are attached is oxygen or sulfur, and that $R_{15}$ is deleted if the atom to which it is attached is oxygen or sulfur, in which each of R, R', and R", independently is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or R and R' or R' and R", together with the atom to which they are attached, are $C_1$-$C_{20}$ heterocycloalkyl or $C_1$-$C_{20}$ heterocycloalkenyl.

Referring to formula (I), $A_{13}$ can be nitrogen, $A_{14}$ can be oxygen, each of the others of $R_1$, $R_2$, $R_3$, $R_4$, $R_5$, $R_6$, $R_7$, and $R_8$, independently, can be H, halo (e.g., Cl or Br), $C_1$-$C_2$ alkyl (e.g., $CH_3$), OR (e.g., OH), NRR' (e.g., $N(CH_3)_2$), or C(O)OR (e.g., $COOCH_3$), each of $R_9$, $R_{10}$, $R_{11}$, $R_{12}$, and $R_{16}$, independently, can be H, halo (e.g., F, Cl, or Br), $C_1$-$C_{10}$ alkyl (e.g., $CH_3$), aryl (e.g., phenyl), OR (e.g., $OCH_3$), $NO_2$, or $S(O)_2$NRR' (e.g., $S(O)_2N(CH_3)_2$), one of $R_{13}$ and $R_{14}$ can be deleted, the other of $R_{13}$ and $R_{14}$ can be H or $C_1$-$C_{10}$ alkyl substituted with aryl, and $R_{15}$ can be deleted.

The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH=CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Another embodiment of the invention features a method for treating cancer. The method includes administering to a subject in need thereof an effective amount of one or more azulene compounds of formula (I) shown above except that each of the others of $R_1$, $R_2$, $R_3$, $R_4$, $R_5$, $R_6$, $R_7$, and $R_8$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, $NO_2$, NO, $N_3$, SCN, CN, OCN, OR, OC(O)R, OC(S)R, OC(S)OR, OC(O)SR, OC(S)SR, OC(O)NRR', OC(S)NRR', ONRR', OS(O)R, OS(O)$_2$R, SR, SC(O)R, SC(S)R, SC(S)OR, SC(O)SR, SC(S)SR, SC(O)NRR', SC(S)NRR', S(O)R, S(O)$_2$R, S(O)NRR', S(O)$_2$NRR', S(O)OR, S(O)$_2$OR, NCO, NCS, NRR', N(R)—C(O)R', N(R)—C(O)OR', N(R)—C(S)R', N(R)—C(S)OR', N(C(O)R)—C(O)R', N(R)—S(O)R', N(R)—S(O)OR', N(R)—S(O)$_2$R', N(R)—S(O)$_2$OR', N(R)—OR', N(OR)—C(O)R', N(OR)—C(O)OR', N(OR)—C(S)R', N(OR)—C(S)OR', N(OR)—C(S)SR', N(OR)—S(O)R', N(OR)—S(O)OR', N(OR)—S(O)$_2$R', N(OR)—S(O)$_2$OR', C(O)R, C(O)OR, C(O)NRR', C(O)SR, C(S)R, C(S)OR, C(S)NRR', C(S)SR, C(NR)—R', C(NR)—OR', C(NR)—NR'R", C(NR)—SR', C(NOR)—R', C(NOR)—OR', C(NOR)—NR'R", and C(NOR)—SR', or $R_1$ and $R_2$, $R_2$ and $R_3$, $R_4$ and $R_5$, $R_5$ and $R_6$, $R_6$ and $R_7$, or $R_7$ and $R_8$, together with the atoms to which they are attached, are $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl, provided that each of the others of $R_1$, $R_2$, $R_3$, $R_4$, $R_5$, $R_6$, $R_7$, and $R_8$ independently, is deleted if the atom to which it is attached is nitrogen. Examples of cancer include leukemia (e.g., acute myelogenous leukemia), gastrointestinal cancer (e.g., a gastrointestinal stromal tumor), kidney cancer (e.g., metastatic renal cell carcinoma), or lung cancer (e.g., small cell lung cancer).

The term "treating" or "treatment" refers to administering one or more azulene compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

In addition, another embodiment of the invention encompasses a pharmaceutical composition that contains an effective amount of at least one of the above-mentioned azulene compounds and a pharmaceutically acceptable carrier.

The azulene compounds described above include the compounds themselves, as well as their salts, prodrugs, solvates, complexes, or radioisotope labeled derivatives, if applicable. A salt, for example, can be formed between an anion and a positively charged group (e.g., amino) on an azulene compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on an azulene compound. Suitable cations include sodium ion, potassium ion, magnesium ion, calcium ion, and an ammonium cation such as tetramethylammonium ion. The azulene compounds also include those salts containing quaternary nitrogen atoms. Examples of prodrugs include esters and other pharmaceutically acceptable derivatives, which, upon administration to a subject, are capable of providing active azulene compounds. A solvate refers to a molecule formed between an active azulene compound and a pharmaceutically acceptable solvent. Examples of pharmaceutically acceptable solvents include water, ethanol, isopropanol, ethyl acetate, acetic acid, and ethanolamine. A complex can be formed between an active azulene compound and a complexing agent (e.g., cyclodextrins or cyclophanes) or between an active azulene compound and an inorganic cation (e.g., zinc, magnesium, calcium, silver, or copper cations).

Also within the scope of this invention is a composition containing one or more of the azulene compounds described above for use in treating cancer, and the use of such a composition for the manufacture of a medicament for the just-mentioned treatment.

A detailed description of the invention is provided in the following.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Table 1 shows azulene compounds of the invention.

TABLE 1

| Compounds | Structures | Names |
|---|---|---|
| 001 | 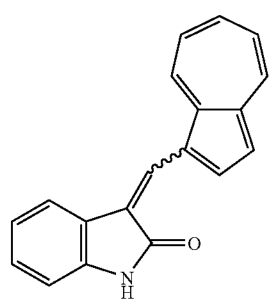 | 3-Azulen-1-ylmethylene-1,3-dihydro-indol-2-one |
| 002 | 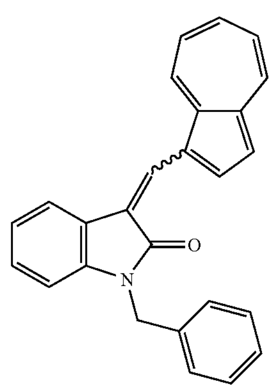 | 3-Azulen-1-ylmethylene-1-benzyl-1,3-dihydro-indol-2-one |

TABLE 1-continued
| Compounds | Structures | Names |
|---|---|---|
| 003 | 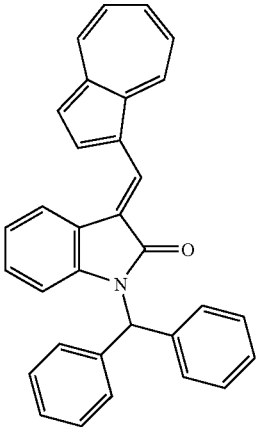 | 3-Azulen-1-ylmethylene-1-benzhydryl-1,3-dihydro-indol-2-one |
| 004 | 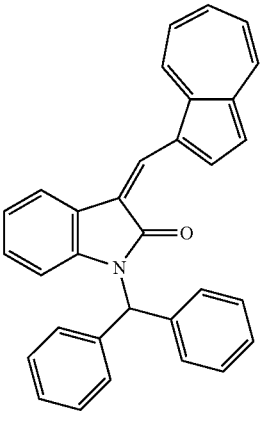 | 3-Azulen-1-ylmethylene-1-benzhydryl-1,3-dihydro-indol-2-one |
| 005 | | |
| 006 | 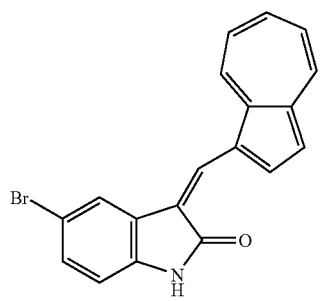 | 3-Azulen-1-ylmethylene-5-bromo-1,3-dihydro-indol-2-one |
| 007 | 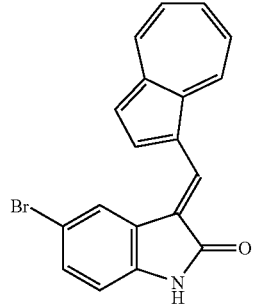 | 3-Azulen-1-ylmethylene-5-bromo-1,3-dihydro-indol-2-one |

TABLE 1-continued

| Compounds | Structures | Names |
|---|---|---|
| 008 | 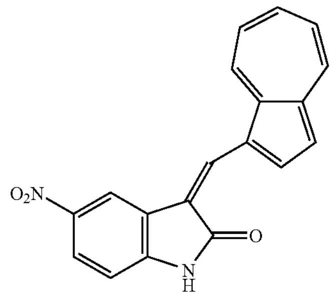 | 3-Azulen-1-ylmethylene-5-nitro-1,3-dihydro-indol-2-one |
| 009 | 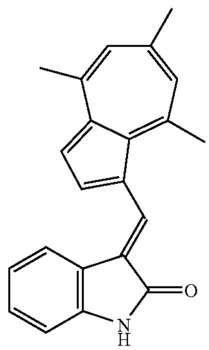 | 3-(4,6,8-Trimethyl-azulen-1-ylmethylene)-1,3-dihydro-indol-2-one |
| 010 | 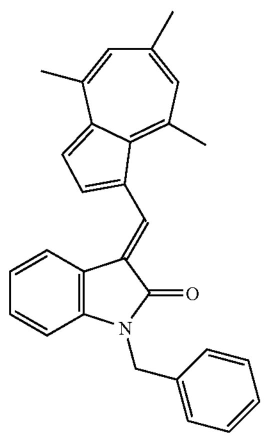 | 1-Benzyl-3-(4,6,8-trimethyl-azulen-1-ylmethylene)-1,3-dihydro-indol-2-one |
| 011 | 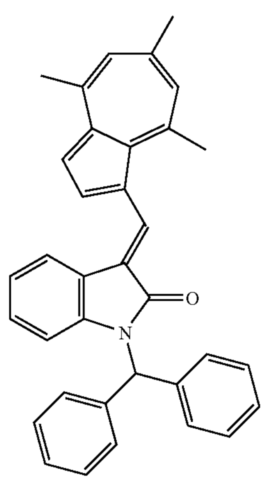 | 1-(2-Methylene-1-phenyl-but-3-enyl)-3-(4,6,8-trimethyl-azulen-1-ylmethylene)-1,3-dihydro-indol-2-one |

TABLE 1-continued
| Compounds | Structures | Names |
|---|---|---|
| 012 | 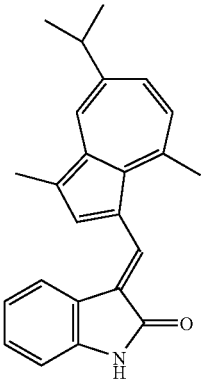 | 3-(5-Isopropyl-3,8-dimethyl-azulen-1-ylmethylene)-1,3-dihydro-indol-2-one |
| 013 | 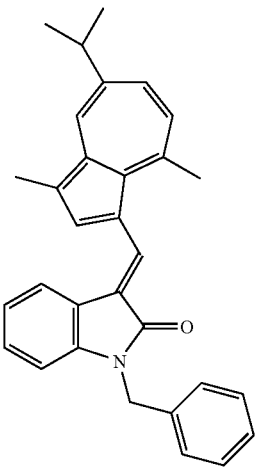 | 1-Benzyl-3-(5-isopropyl-3,8-dimethyl-azulen-1-ylmethylene)-1,3-dihydro-indol-2-one |
| 014 | 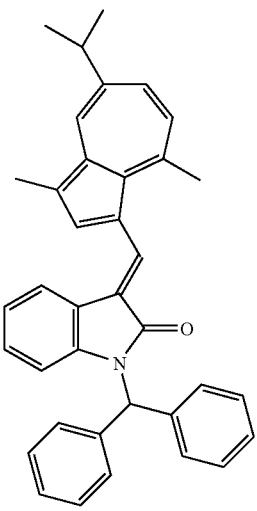 | 1-Benzhydryl-3-(5-isopropyl-3,8-dimethyl-azulen-1-ylmethylene)-1,3-dihydro-indol-2-one |
| 015 | | |

TABLE 1-continued
| Compounds | Structures | Names |
|---|---|---|
| 016 | 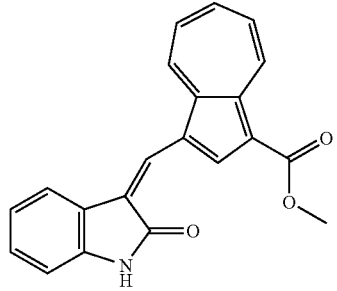 | 3-(2-Oxo-1,2-dihydro-indol-3-ylidenemethyl)-azulene-1-carboxylic acid methyl ester |
| 017 | | |
| 018 | | |
| 019 | 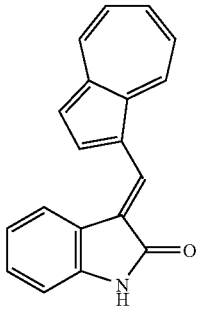 | 3-Azulen-1-ylmethylene-1,3-dihydro-indol-2-one |
| 020 | 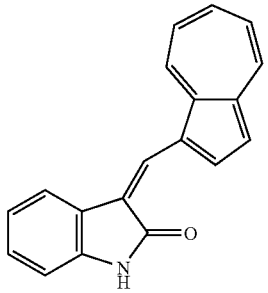 | 3-(2-Oxo-1,2-dihydro-indol-3-ylidenemethyl)-azulene-1-carboxylic acid methyl ester |
| 021 | | |
| 022 | 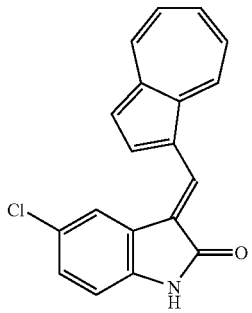 | 3-Azulen-1-ylmethylene-5-chloro-1,3-dihydro-indol-2-one |

TABLE 1-continued

| Compounds | Structures | Names |
|---|---|---|
| 023 | 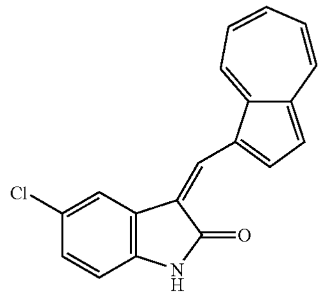 | 3-Azulen-1-ylmethylene-5-chloro-1,3-dihydro-indol-2-one |
| 024 | | |
| 025 | 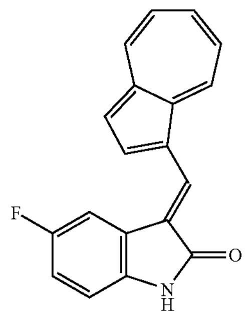 | 3-Azulen-1-ylmethylene-5-fluoro-1,3-dihydro-indol-2-one |
| 026 | 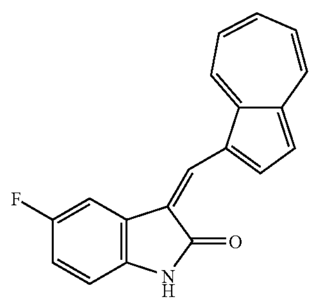 | 3-Azulen-1-ylmethylene-5-fluoro-1,3-dihydro-indol-2-one |
| 027 | 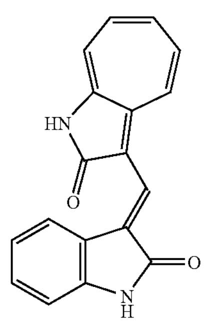 | 3-(2-Oxo-1,2-dihydro-indol-3-ylidenemethyl)-1H-cyclohepta[b]pyrrol-2-one |
| 028 | 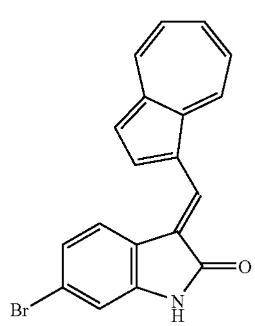 | 3-Azulen-1-ylmethylene-6-bromo-1,3-dihydro-indol-2-one |

TABLE 1-continued

| Compounds | Structures | Names |
|---|---|---|
| 029 | 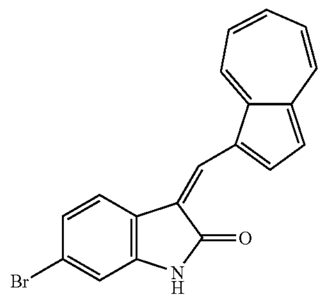 | 3-Azulen-1-ylmethylene-6-bromo-1,3-dihydro-indol-2-one |
| 030 | 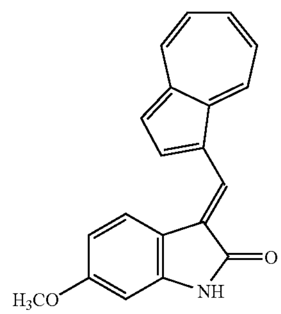 | 3-Azulen-1-ylmethylene-6-methoxy-1,3-dihydro-indol-2-one |
| 031 | 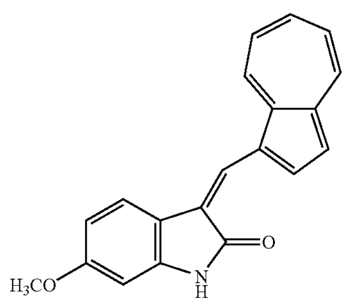 | 3-Azulen-1-ylmethylene-6-methoxy-1,3-dihydro-indol-2-one |
| 032 | 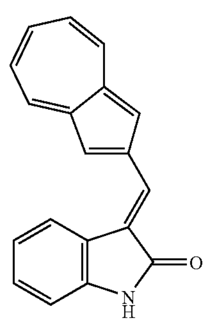 | 3-Azulen-2-ylmethylene-1,3-dihydro-indol-2-one |
| 033 | 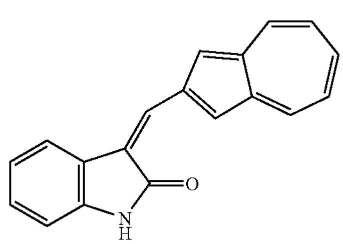 | 3-Azulen-2-ylmethylene-1,3-dihydro-indol-2-one |

TABLE 1-continued
| Compounds | Structures | Names |
|---|---|---|
| 034 | 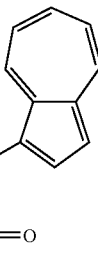 | 3-Azulen-1-ylmethylene-5-phenyl-1,3-dihydro-indol-2-one |
| 035 | 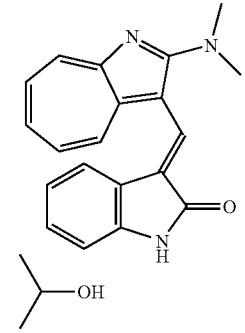 | 3-(2-Dimethylamino-cyclohepta[b]pyrrol-3-ylmethylene)-1,3-dihydro-indol-2-one, with propan-2-ol |
| 036 | 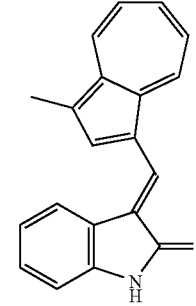 | 3-(3-Methyl-azulen-1-ylmethylene)-1,3-dihydro-indol-2-one |
| 037 | 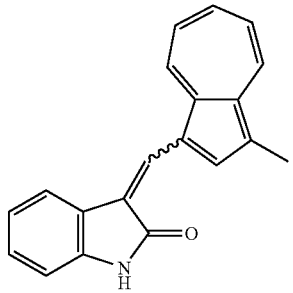 | 3-(3-Methyl-azulen-1-ylmethylene)-1,3-dihydro-indol-2-one |
| 038 | 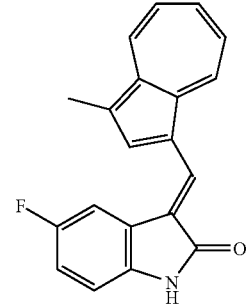 | 5-Fluoro-3-(3-methyl-azulen-1-ylmethylene)-1,3-dihydro-indol-2-one |

TABLE 1-continued
| Compounds | Structures | Names |
|---|---|---|
| 039 | 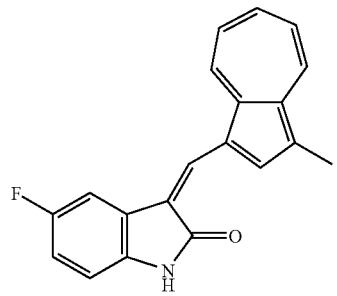 | 5-Fluoro-3-(3-methyl-azulen-1-ylmethylene)-1,3-dihydro-indol-2-one |
| 040 | 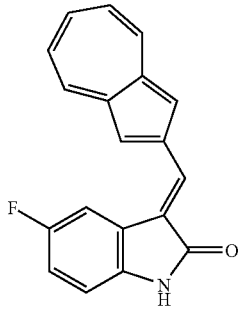 | 3-Azulen-2-ylmethylene-5-fluoro-1,3-dihydro-indol-2-one |
| 041 | 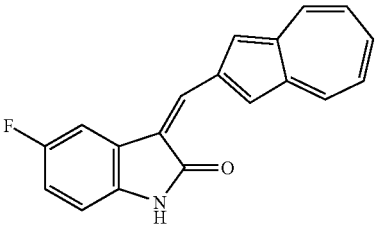 | 3-Azulen-2-ylmethylene-5-fluoro-1,3-dihydro-indol-2-one |
| 042 | 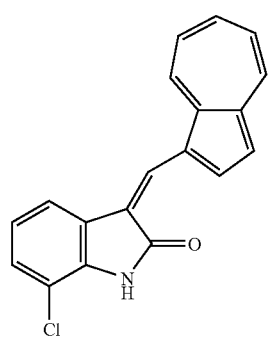 | 3-Azulen-1-ylmethylene-7-chloro-1,3-dihydro-indol-2-one |
| 043 | 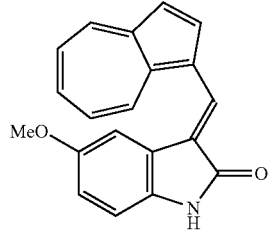 | 3-Azulen-1-ylmethylene-5-methoxy-1,3-dihydro-indol-2-one |

TABLE 1-continued

| Compounds | Structures | Names |
|---|---|---|
| 044 | 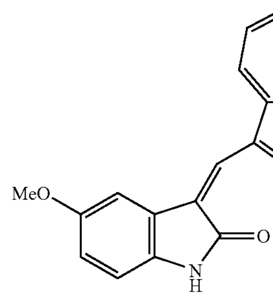 | 3-Azulen-1-ylmethylene-5-methoxy-1,3-dihydro-indol-2-one |
| 045 | 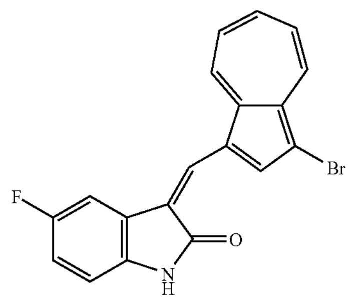 | 3-(3-Bromo-azulen-1-ylmethylene)-5-fluoro-1,3-dihydro-indol-2-one |
| 046 | 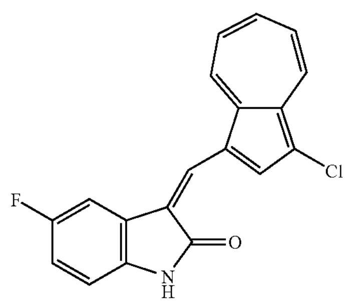 | 3-(3-Chloro-azulen-1-ylmethylene)-5-fluoro-1,3-dihydro-indol-2-one |
| 047 | 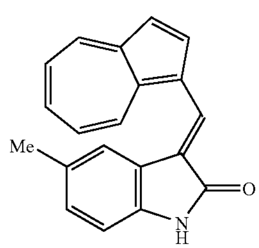 | 3-Azulen-1-ylmethylene-5-methyl-1,3-dihydro-indol-2-one |
| 048 | 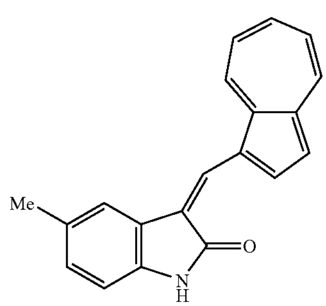 | 3-Azulen-1-ylmethylene-5-methyl-1,3-dihydro-indol-2-one |

TABLE 1-continued

| Compounds | Structures | Names |
|---|---|---|
| 049 | 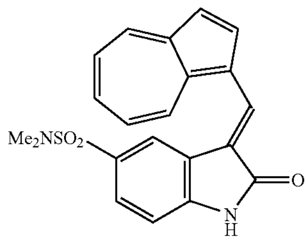 | (3E)-3-(((3aZ,5Z,7Z)-azulen-1-yl)methylene)-5-(N,N-dimethylsulfonyl)indolin-2-one |
| 050 | 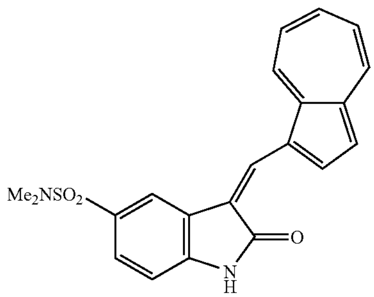 | (3Z)-3-(((3aZ,5Z,7Z)-azulen-1-yl)methylene)-5-(N,N-dimethylsulfonyl)indolin-2-one |
| 051 | 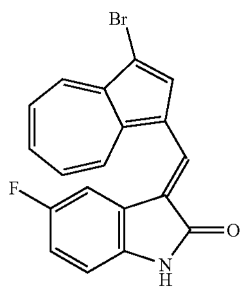 | 3-(3-Bromo-azulen-1-ylmethylene)-5-fluoro-1,3-dihydro-indol-2-one |
| 052 | 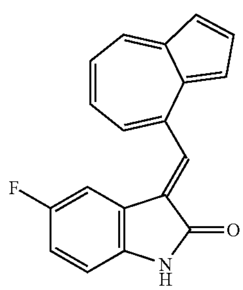 | 3-Azulen-4-ylmethylene-5-fluoro-1,3-dihydro-indol-2-one |
| 053 | 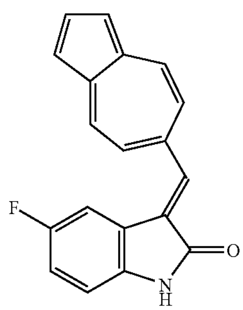 | 3-Azulen-6-ylmethylene-5-fluoro-1,3-dihydro-indol-2-one |

TABLE 1-continued

| Compounds | Structures | Names |
|---|---|---|
| 054 | 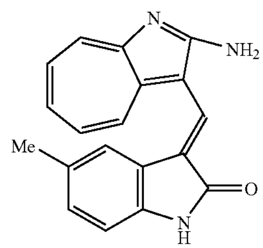 | 3-(2-Amino-cyclohepta[b]pyrrol-3-ylmethylene)-5-methyl-1,3-dihydro-indol-2-one |
| 055 | 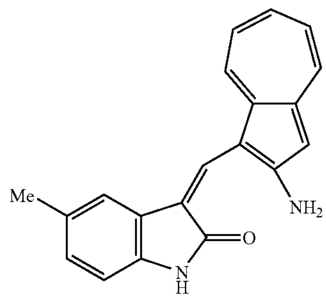 | 3-(2-Amino-cyclohepta[b]pyrrol-3-ylmethylene)-5-methyl-1,3-dihydro-indol-2-one |
| 056 | 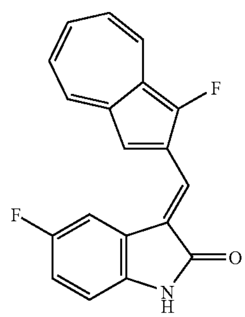 | 5-Fluoro-3-(1-fluoro-azulen-2-ylmethylene)-1,3-dihydro-indol-2-one |
| 057 | 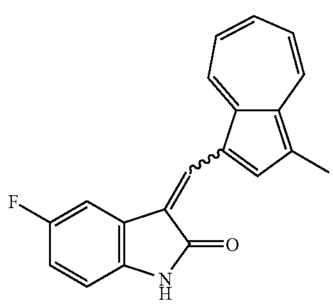 | 5-Fluoro-3-(3-methyl-azulen-1-ylmethylene)-1,3-dihydro-indol-2-one |
| 058 | 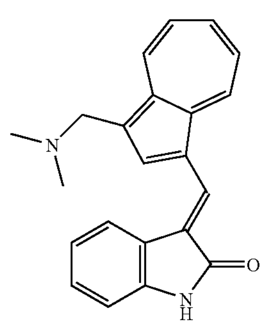 | 3-(3-Dimethylaminomethyl-azulen-1-ylmethylene)-1,3-dihydro-indol-2-one |

TABLE 1-continued

| Compounds | Structures | Names |
|---|---|---|
| 059 | 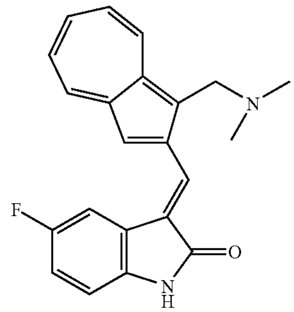 | 3-(1-Dimethylaminomethyl-azulen-2-ylmethylene)-5-fluoro-1,3-dihydro-indol-2-one |
| 060 | 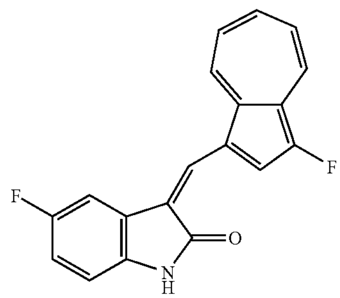 | 5-Fluoro-3-(3-fluoro-azulen-1-ylmethylene)-1,3-dihydro-indol-2-one |
| 061 | 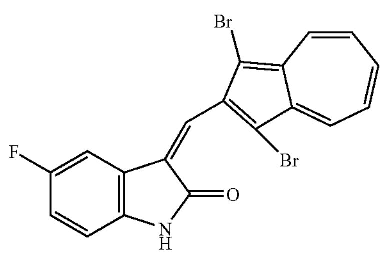 | 3-(1,3-Dibromo-azulen-2-ylmethylene)-5-fluoro-1,3-dihydro-indol-2-one |
| 062 | 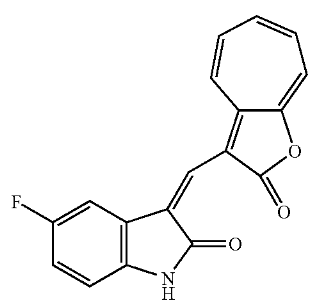 | 5-Fluoro-3-(2-oxo-2H-cyclohepta[b]furan-3-ylmethylene)-1,3-dihydro-indol-2-one |
| 063 | 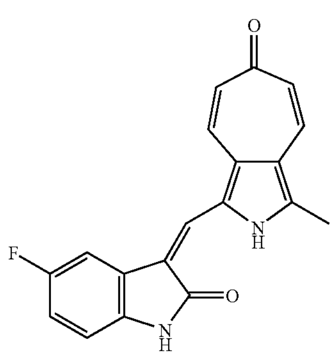 | 1-(5-Fluoro-2-oxo-1,2-dihydro-indol-3-ylidenemethyl)-3-methyl-2H-cyclohepta[c]pyrrol-6-one |

TABLE 1-continued

| Compounds | Structures | Names |
|---|---|---|
| 064 | 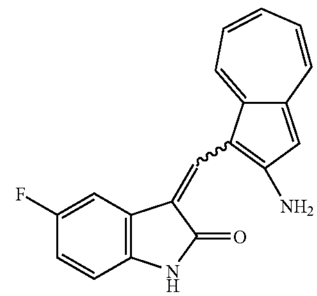 | 3-(2-Amino-azulen-1-ylmethylene)-5-fluoro-1,3-dihydro-indol-2-one |
| 065 | 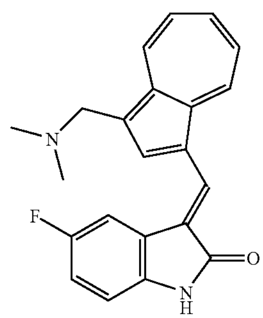 | 3-(3-Dimethylaminomethyl-azulen-1-ylmethylene)-5-fluoro-1,3-dihydro-indol-2-one |
| 066 | 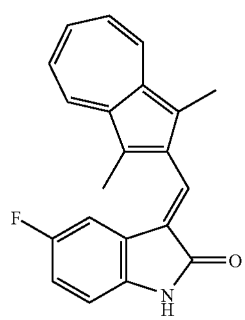 | 3-(1,3-Dimethyl-azulen-2-ylmethylene)-5-fluoro-1,3-dihydro-indol-2-one |
| 067 | 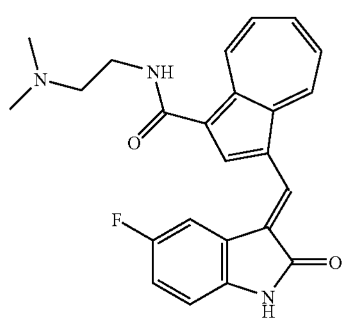 | 3-(5-Fluoro-2-oxo-1,2-dihydro-indol-3-ylidenemethyl)-azulene-1-carboxylic acid (2-dimethylamino-ethyl)-amide |

TABLE 1-continued

| Compounds | Structures | Names |
|---|---|---|
| 068 | 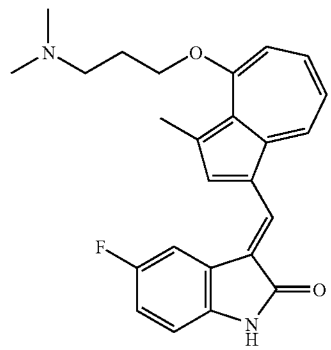 | 3-[4-(3-Dimethylamino-propoxy)-3-methyl-azulen-1-ylmethylene]-5-fluoro-1,3-dihydro-indol-2-one |
| 069 | 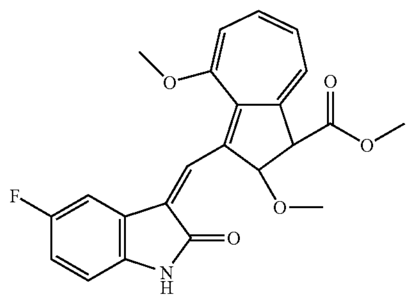 | 3-(5-Fluoro-2-oxo-1,2-dihydro-indol-3-ylidenemethyl)-2,4-dimethoxy-1,2-dihydro-azulene-1-carboxylic acid methyl ester |
| 070 | 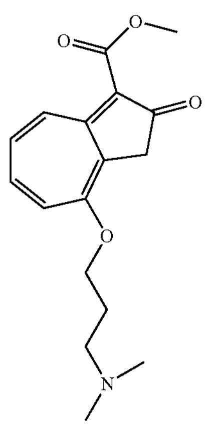 | 4-(3-Dimethylamino-propoxy)-2-oxo-2,3-dihydro-azulene-1-carboxylic acid methyl ester |
| 071 | 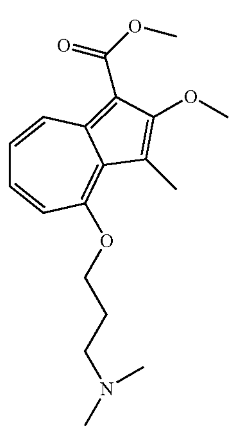 | 4-(3-Dimethylamino-propoxy)-2-methoxy-3-methyl-azulene-1-carboxylic acid methyl ester |

TABLE 1-continued

| Compounds | Structures | Names |
|---|---|---|
| 072 | 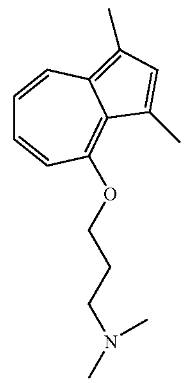 | [3-(1,3-Dimethyl-azulen-4-yloxy)-propyl]-dimethyl-amine |
| 073 | 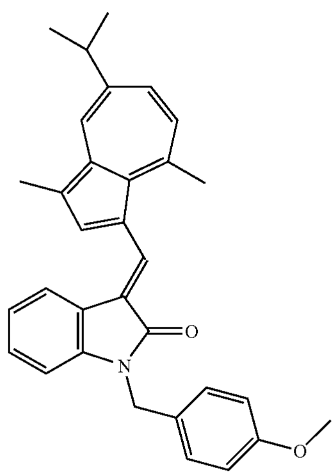 | 3-(5-Isopropyl-3,8-dimethyl-azulen-1-ylmethylene)-1-(4-methoxy-benzyl)-1,3-dihydro-indol-2-one |
| 074 | 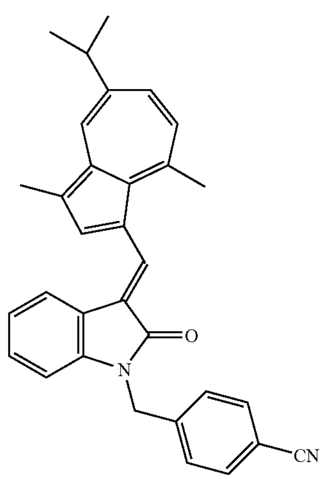 | 4-[3-(5-Isopropyl-3,8-dimethyl-azulen-1-ylmethylene)-2-oxo-2,3-dihydro-indol-1-ylmethyl]-benzonitrile |

TABLE 1-continued

| Compounds | Structures | Names |
|---|---|---|
| 075 | 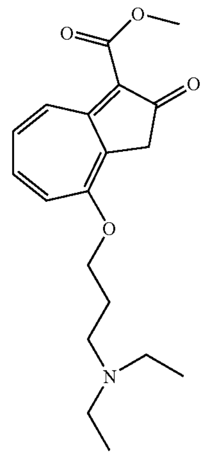 | 4-(3-Diethylamino-propoxy)-2-oxo-2,3-dihydro-azulene-1-carboxylic acid methyl ester |
| 076 | 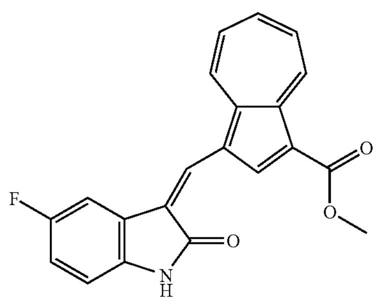 | 3-(5-Fluoro-2-oxo-1,2-dihydro-indol-3-ylidenemethyl)-azulene-1-carboxylic acid methyl ester |
| 077 | 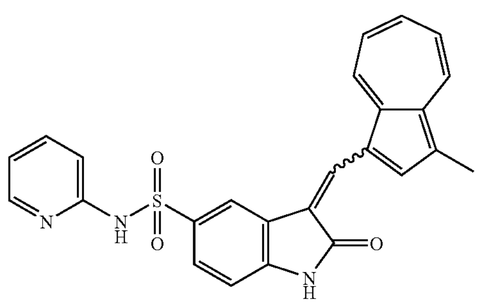 | 3-(3-Methyl-azulen-1-ylmethylene-2-oxo-2,3-dihydro-1H-indole-5-sulfonic acid pyridin-2-ylamide |
| 078 | | |
| 079 | | |
| 080 | 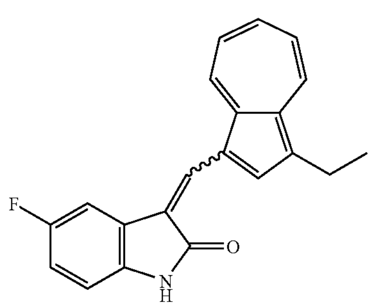 | 3-(3-Ethyl-azulen-1-ylmethylene)-5-fluoro-1,3-dihydro-indol-2-one |

TABLE 1-continued

| Compounds | Structures | Names |
|---|---|---|
| 081 | 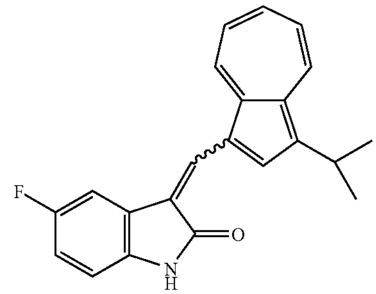 | 5-Fluoro-3-(3-isopropyl-azulen-1-ylmethylene)-1,3-dihydro-indol-2-one |
| 082 | 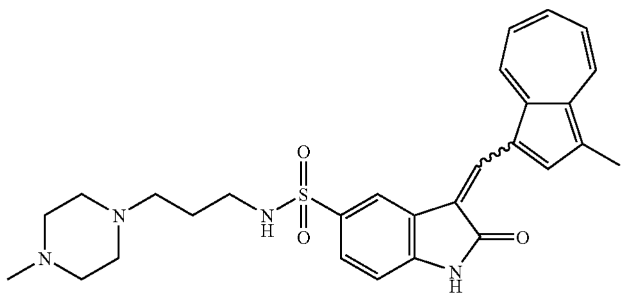 | 3-(3-Methyl-azulen-1-ylmethylene)-2-oxo-2,3-dihydro-1H-indole-5-sulfonic acid [3-(4-methyl-piperazin-1-yl)-propyl]-amide |
| 083 | 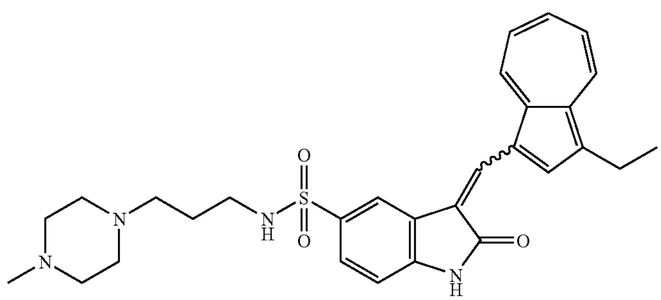 | 3-(3-Ethyl-azulen-1-ylmethylene)-2-oxo-2,3-dihydro-1H-indole-5-sulfonic acid [3-(4-methyl-piperazin-1-yl)-propyl]-amide |
| 084 | 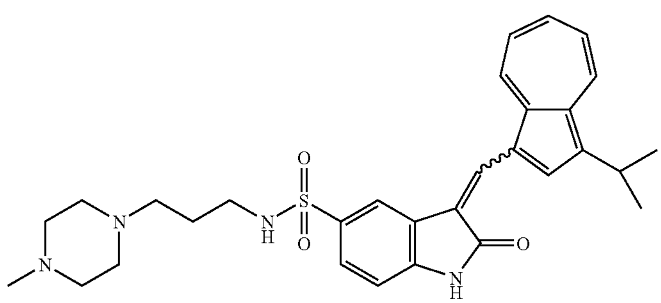 | 3-(3-Ethyl-azulen-1-ylmethylene)-2-oxo-2,3-dihydro-1H-indole-5-sulfonic acid [3-(4-methyl-piperazin-1-yl)-propyl]-amide |
| 085 | 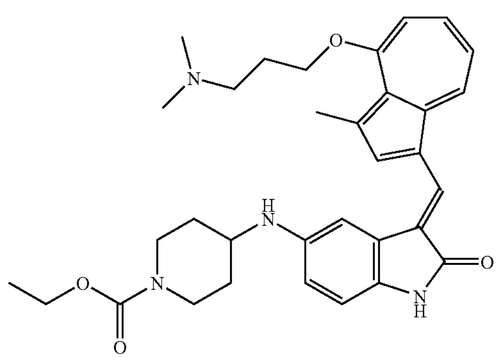 | 4-{3-[4-(3-Dimethylamino-propoxy)-3-methyl-azulen-1-ylmethylene]-2-oxo-2,3-dihydro-1H-indol-5-ylamino}-piperidine-1-carboxylic acid ethyl ester |

TABLE 1-continued

| Compounds | Structures | Names |
|---|---|---|
| 086 | 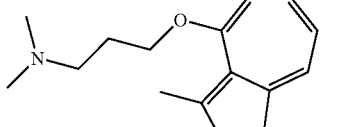 | 4-{3-[4-(3-Dimethylamino-propoxy)-3-methyl-azulen-1-ylmethylene]-2-oxo-2,3-dihydro-1H-indol-5-ylamino}-piperidine-1-carboxylic acid ethyl ester |
| 087 | 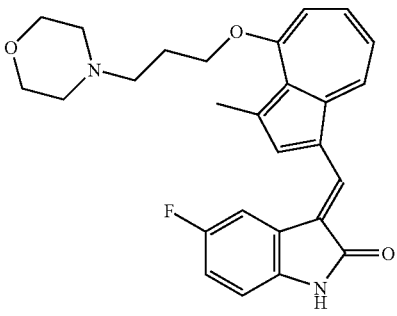 | 5-Fluoro-3-[3-methyl-4-(3-morpholin-4-yl-propoxy)-azulen-1-ylmethylene]-1,3-dihydro-indol-2-one |
| 088 | 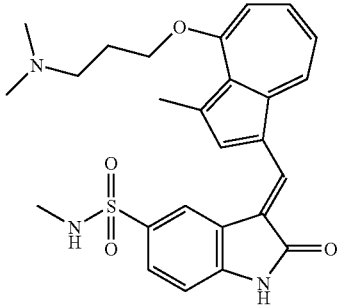 | 3-[4-(3-Dimethylamino-propoxy)-3-methyl-azulen-1-ylmethylene]-2-oxo-2,3-dihydro-1H-indole-5-sulfonic acid methylamide |
| 089 | 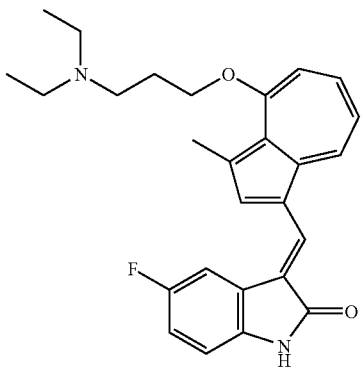 | 3-[4-(3-Diethylamino-propoxy)-3-methyl-azulen-1-ylmethylene]-5-fluoro-1,3-dihydro-indol-2-one |

TABLE 1-continued

| Compounds | Structures | Names |
|---|---|---|
| 090 | 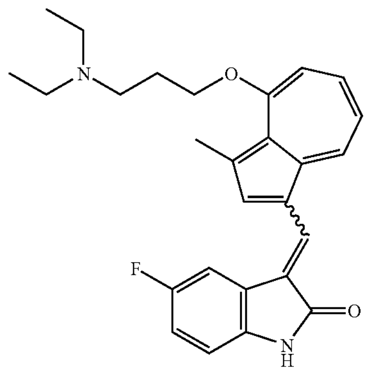 | 3-[4-(3-Diethylamino-propoxy)-3-methyl-azulen-1-ylmethylene]-5-fluoro-1,3-dihydro-indol-2-one |
| 091 | 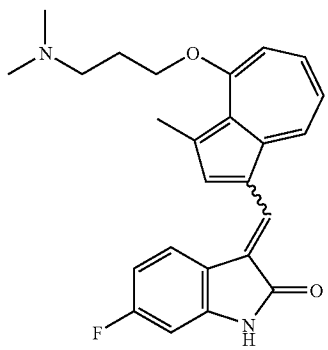 | 3-[4-(3-Dimethylamino-propoxy)-3-methyl-azulen-1-ylmethylene]-6-fluoro-1,3-dihydro-indol-2-one |
| 092 | 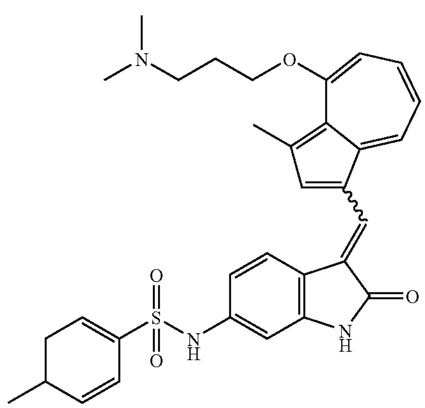 | N-{3-[4-(3-Dimethylamino-propoxy)-3-methyl-azulen-1-ylmethylene]-2-oxo-2,3-dihydro-1H-indol-6-yl}-4-methyl-benzenesulfonamide |
| 093 | 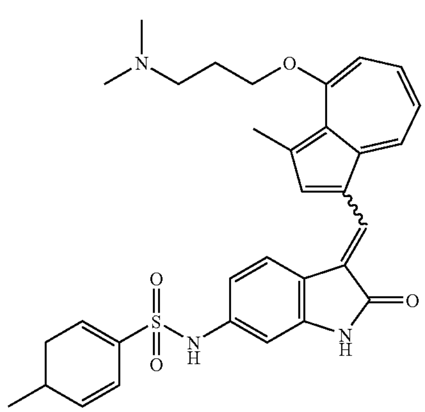 | N-{3-[4-(3-Dimethylamino-propoxy)-3-methyl-azulen-1-ylmethylene]-2-oxo-2,3-dihydro-1H-indol-6-yl}-4-methyl-benzenesulfonamide |

TABLE 1-continued

| Compounds | Structures | Names |
|---|---|---|
| 094 | 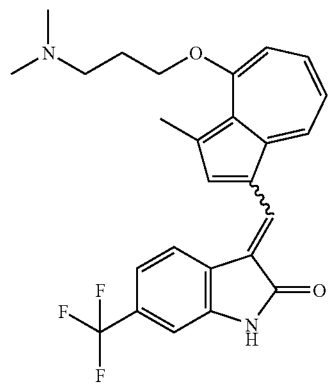 | 3-[4-(3-Dimethylamino-propoxy)-3-methyl-azulen-1-ylmethylene]-6-trifluoromethyl-1,3-dihydro-indol-2-one |
| 095 | 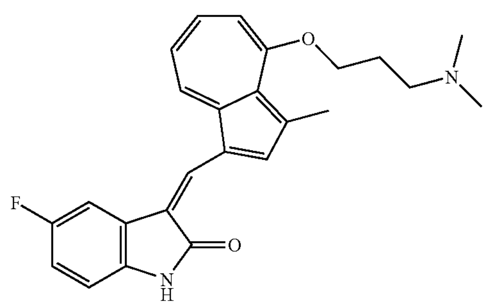 | 3-[4-(3-Dimethylamino-propoxy)-3-methyl-azulen-1-ylmethylene]-5-fluoro-1,3-dihydro-indol-2-one |
| 096 | 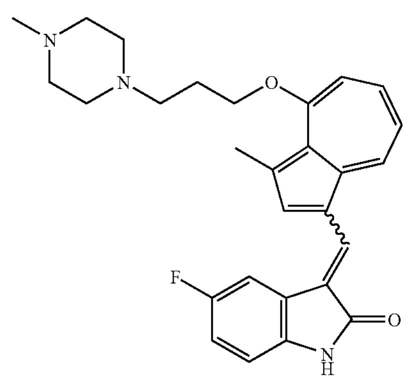 | 5-Fluoro-3-{3-methyl-4-[3-(4-methyl-piperazin-1-yl)-propoxy]-azulen-1-ylmethylene}-1,3-dihydro-indol-2-one |
| 097 | 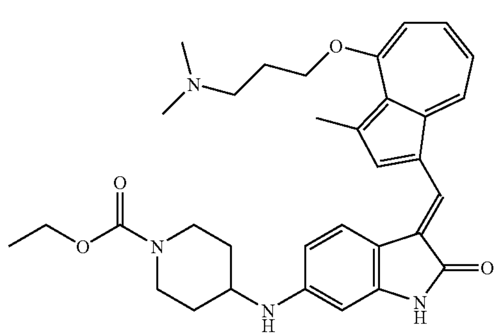 | 4-{3-[4-(3-Dimethylamino-propoxy)-3-methyl-azulen-1-ylmethylene]-2-oxo-2,3-dihydro-1H-indol-6-ylamino}-piperidine-1-carboxylic acid ethyl ester |

TABLE 1-continued

| Compounds | Structures | Names |
|---|---|---|
| 098 | 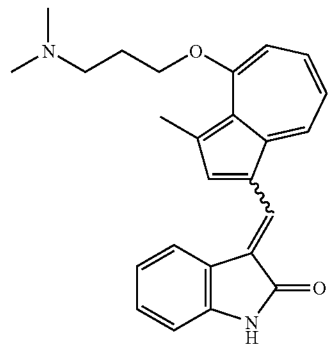 | 3-[4-(3-Dimethylamino-propoxy)-3-methyl-azulen-1-ylmethylene]-1,3-dihydro-indol-2-one |
| 099 | 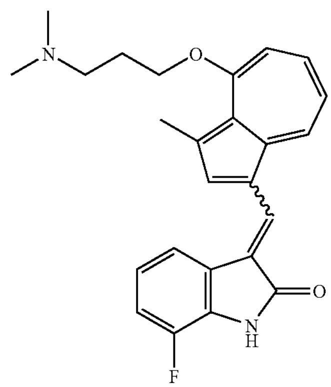 | 3-[4-(3-Dimethylamino-propoxy)-3-methyl-azulen-1-ylmethylene]-7-fluoro-1,3-dihydro-indol-2-one |
| 100 | 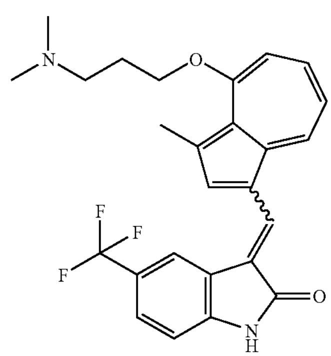 | 3-[4-(3-Dimethylamino-propoxy)-3-methyl-azulen-1-ylmethylene]-5-trifluoromethyl-1,3-dihydro-indol-2-one |
| 104 | 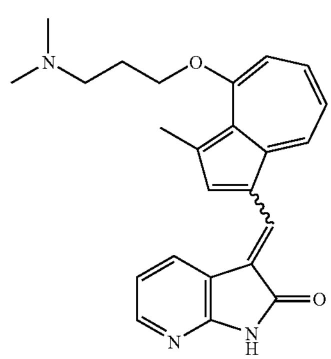 | 3-(((3aZ,5Z,7E)-8-(3-(dimethylamino)propoxy)-1-methylazulen-3-yl)methylene)-1H-pyrrolo[2,3-b]pyridin-2(3H)-one |

The azulene compounds described above can be prepared by methods well known in the art. For example, the following scheme illustrates a typical synthetic route for preparing compounds 001-104.

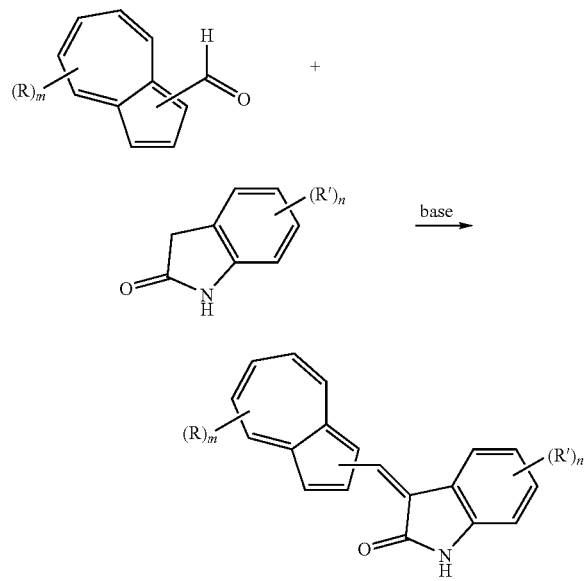

R = Cl, Br, OH, CH₃, NMe₂, NEt₂ or COOMe,
    OCH₃, O(CH₂)ᵢNR₁R₂
R' = F, Cl, Br, OCH₃, CH₃, CF₃, Ph, NMe₂,
    SO₂NR₁R₂, NO₂, or CH(Ph)₂, NR₁R₂
i = 1-4
m = 0-3, and
n = 0 or 1.

Specifically, compounds 001~104 can be prepared by reacting an azulene compound having a formyl group with an indolin-2-one compound. Examples below provide detailed descriptions.

As shown in the above scheme, a base can be used to facilitate synthesizing the azulene compounds of the invention. Preferably, the base is a compound containing a nitrogen atom, such as ammonia, methylamine, trimethylamine, triethylamine, aniline, N-methylaniline, dimethylaminopyridine, proline, 1,8-diazabicyclo[5.4.0]undec-7-ene, diisopropylethylamine, pyrrolidine, piperidine, sodium amide, lithium diisopropylamide, and sodium hexamethyldisilazanide. Other organic or inorganic bases can also be used in the reaction set forth in the above scheme. Examples of organic bases that do not contain a nitrogen atom include carbonates, bicarbonates, acetates, formates, alkyl lithium compounds, aryl lithium compounds, metal alkoxides, and Grignard reagents. Examples of inorganic bases include hydroxides, phosphates, bisulfates, hydrosulfides, and hydrides.

The reaction set forth in the above scheme can take place in the presence of a solvent, which can be either protic or aprotic. Examples of protic solvents include alcohols and water. Examples of aprotic solvents include hexane, toluene, benzene, methylene chloride, dimethylformamide, dimethylsulfoxide, chloroform, and tetrahydrofuran. The reaction set forth in the above scheme can also take place in the absence of a solvent.

An azulene compound thus synthesized can be purified by a suitable method such as column chromatography, high-pressure liquid chromatography, or recrystallization.

Other azulene compounds can be prepared using other suitable starting materials through the above synthetic routes and others known in the art. The methods described above may also additionally include steps, either before or after the steps described specifically herein, to add or remove suitable protecting groups in order to ultimately allow synthesis of the azulene compounds. In addition, various synthetic steps may be performed in an alternate sequence or order to give the desired compounds. Synthetic chemistry transformations and protecting group methodologies (protection and deprotection) useful in synthesizing applicable azulene compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The azulene compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing an effective amount of at least one azulene compound described above and a pharmaceutical acceptable carrier. Further, this invention covers a method of administering an effective amount of one or more of the azulene compounds to a patient having cancer. "An effective amount" refers to the amount of an active azulene compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

The azulene compounds of the invention are useful for detecting either azulene or oxindole recognition sites. An azulene or oxindole recognition site can be any enzyme, receptor, or transporter site that binds to the azulene or oxindole moiety of an azulene compound of the invention. Thus, the compounds of the invention can be used as diagnostic agents, prognostic agents, molecular probes, separation tools and therapeutic agents relating to diseases or disorders associated with such an enzyme, receptor, or transporter.

The invention also provides a method of regulating the activity of protein kinase or protein phosphatase with one of the azulene compounds described above. The method includes contacting cells expressing protein kinase or phosphatase with such an azulene compound. Protein kinase and phosphatase regulate signaling cascades. The cascades in turn regulate cell growth, migration, differentiation, gene expression, muscle contraction, glucose metabolism, cellular protein synthesis, and regulation of the cell cycle.

To practice the treatment method of the invention, a composition having one or more azulene compounds can be administered to a subject (e.g., a mammal) parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active azulene compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active azulene compound. Examples of other carriers include colloidal silicon oxide, magnesium stearate, cellulose, sodium lauryl sulfate, and D&C Yellow # 10.

The azulene compounds described above can be preliminarily screened for their efficacy in treating above-described diseases by in vitro assays and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Preparation of 3-Azulen-1-ylmethylene-1,3-dihydro-indol-2-one (001)

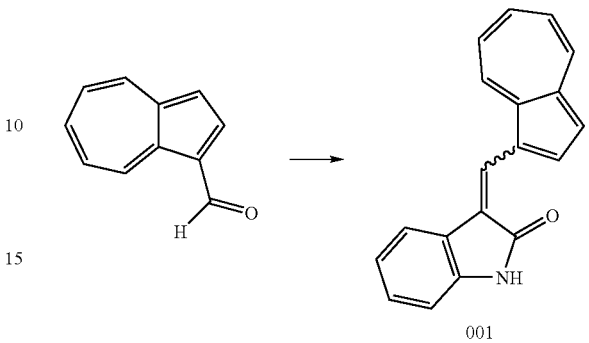

1-Formylazulene (2 mmol) was dissolved in 40 mL ethanol. 266 mg oxindole (2 mmol) and 200 mL ethanol were then added. Next, a 4 mL solution containing 1M pyrrolidine and ethanol was added to react at room temperature for three days. After removal of solvent, the resulting solution was extracted by 150 mL acetyl acetate and 50 mL water. The resulting solution was extracted again by 50 mL citric acid aqueous solution and ethyl acetate. The ethyl acetate layer was collected, dried with anhydrous magnesium sulfate, filtered, and concentrated under vacuum. The residue was then purified by column chromatography (Silica Gel 60, dichloromethane) and dried to give Compound 001 (552 mg, 95%).

001 $^1$H-NMR (500 MHz, CDCl$_3$) δ (ppm) 8.70 (d, J=10.0 Hz, 1H), 8.63 (d, J=4.5 Hz, 1H), 8.42 (s, 1H), 8.39 (s, 1H), 8.38 (d, J=10.0 Hz, 1H), 7.93 (d, J=8.0 Hz, 1H), 7.73 (t, J=10.0 Hz, 1H), 7.55 (d, J=4.5 Hz, 1H), 7.38 (t, J=10.0 Hz, 1H), 7.36 (t, J=10.0 Hz, 1H), 7.20 (t, J=8.0 Hz, 1H), 6.91 (t, J=8.0 Hz, 1H), 6.90 (t, J=8.0 Hz, 1H); 001 $^1$H-NMR (500 MHz, CDCl$_3$) δ (ppm) 9.74 (d, J=4.5 Hz, 1H), 8.70 (d, J=10.0 Hz, 1H), 7.64 (d, J=7.5 Hz, 1H), 7.42 (t, J=10.0 Hz, 1H), 7.18 (t, J=7.5 Hz, 1H), 7.06 (t, J=7.5 Hz, 1H), 6.90 (d, J=7.5 Hz, 1H), 8.40-6.80 (m, 5H).

Example 2

Preparation of 3-Azulen-1-ylmethylene-1-benzyl-1,3-dihydro-indol-2-one (002)

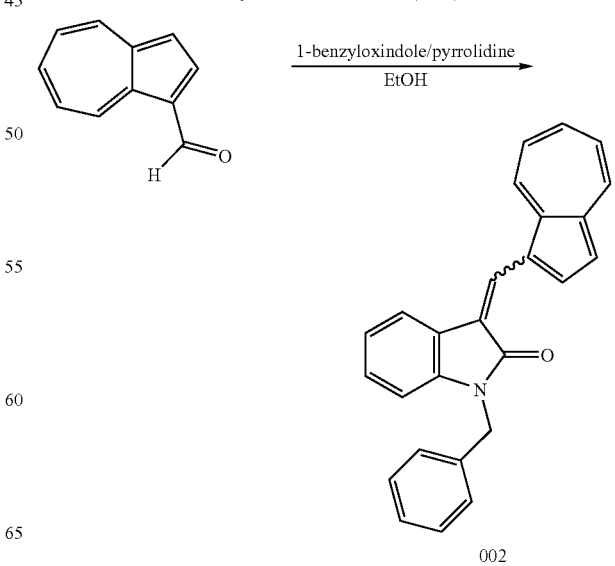

1-Formylazulene (1 mmol) was dissolved in 20 mL ethanol. 223 mg 1-benzylindolin-2-one (1 mmol) and 20 mL ethanol were then added. Next, a 2 mL solution (1 mmol) containing 1M pyrrolidine and ethanol was added to react at room temperature for three days. After removal of solvent, the resulting solution was extracted by 150 mL ethyl acetate and 50 mL water. The resulting solution was extracted again by 50 mL citric acid aqueous solution and ethyl acetate. The ethyl acetate layer was collected, dried with anhydrous magnesium sulfate, filtered, and concentrated under vacuum. Next, methanol was added and ultrasonically shaken at 40° C. for 1 hour. After filtration, washing by methanol, and drying, Compound 002 (315 mg, 87%) was obtained.

002 (E) $^1$H-NMR (500 MHz, CDCl$_3$) δ (ppm) 8.70 (d, J=10.0 Hz, 1H), 8.48 (s, 1H), 8.35 (d, J=9.0 Hz, 1H), 8.24 (s, 1H), 7.70 (t, J=10.0 Hz, 1H), 7.66 (dd, J=7.5, 0.5 Hz, 1H), 7.52 (d, J=4.5 Hz, 1H), 7.41 (t, J=10.0 Hz, 1H), 7.37-7.20 (m, 5H), 7.12 (dt, J=8.0, 1.0 Hz, 1H), 7.03 (dt, J=7.0, 0.5 Hz, 1H), 6.73 (d, J=7.0 Hz, 1H); 002 (Z) $^1$H-NMR (500 MHz, CDCl$_3$) δ (ppm) 8.64 (d, J=9.5 Hz, 1H), 8.53 (d, J=4.0 Hz, 1H), 8.37 (d, J=9.5 Hz, 1H), 7.93 (d, J=7.5 Hz, 1H), 7.72 (t, J=9.5 Hz, 1H), 7.50 (d, J=4.5 Hz, 1H), 7.37-7.20 (m, 5H), 7.13 (dt, J=8.0, 1.5 Hz, 1H), 6.90 (dt, J=11.0, 1.0 Hz, 1H), 6.75 (d, J=7.0 Hz, 1H). LC-MS (m/z) 362 [M+1].

Example 3

Preparation of (E)-3-(azulen-1-ylmethylene)-1-benzhydrylindolin-2-one (003) and (Z)-3-(azulen-1-ylmethylene)-1-benzhydrylindolin-2-one (004)

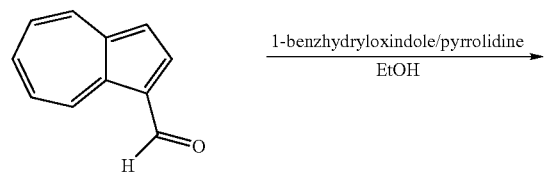

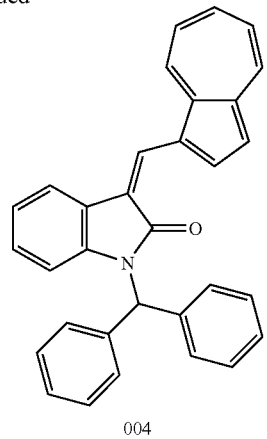

Compounds 003 and 004 were prepared in a manner similar to that described in Example 1. The results were purified by column chromatography (Silica Gel 60, dichloromethane: ethyl acetate=2:1) and dried to give Compounds 003 (176.6 mg) and 004 (242.5 mg).

003 $^1$H-NMR (500 MHz, CDCl$_3$) δ (ppm) 9.82 (s, 1H), 8.62 (d, J=10.0 Hz, 1H), 8.54 (d, J=4.5 Hz, 1H), 8.47 (s, 1H), 8.38 (d, J=10.0 Hz, 1H), 7.96 (d, J=7.5 Hz, 1H), 7.72 (t, J=10.0 Hz, 1H), 7.50 (d, J=4.5 Hz, 1H), 7.37 (t, J=10.0 Hz, 1H), 7.40-7.10 (m, 13H), 7.20 (s, 1H), 6.96 (t, J=7.5 Hz, 1H), 6.85 (t, J=7.5 Hz, 1H), 6.51 (d, J=8.0 Hz, 1H); 004 $^1$H-NMR (500 MHz, CDCl$_3$) δ (ppm) 9.83 (d, J=4.5 Hz, 1H), 8.71 (d, J=10.0 Hz, 1H), 8.35 (d, J=10.0 Hz, 1H), 8.27 (s, 1H), 7.71 (t, J=10.0 Hz, 1H), 7.67 (d, J=7.5 Hz, 1H), 7.51 (d, J=4.5 Hz, 1H), 7.42 (t, J=10.0 Hz, 1H), 7.40-7.10 (m, 14H), 6.99 (t, J=7.5 Hz, 1H), 6.92 (t, J=7.5 Hz, 1H), 6.40 (d, J=8.0 Hz, 1H). LC-MS (m/z) 438 [M+1].

Example 4

Preparation of (Z)-3-(azulen-1-ylmethylene)-5-bromoindolin-2-one (006) and (E)-3-(azulen-1-ylmethylene)-5-bromoindolin-2-one (007)

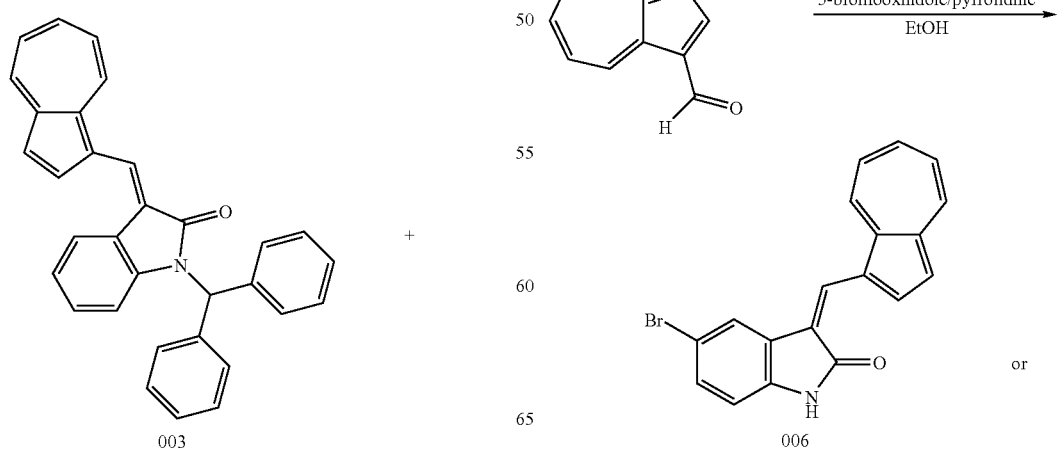

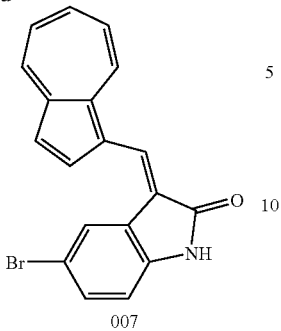

Compounds 006 and 007 were prepared in a manner similar to that described in Example 1. The results were purified by column chromatography (Silica Gel 60, dichloromethane: ethyl acetate=20:1) and dried to give Compounds 006 and 007.

006 $^1$H-NMR (500 MHz, DMSO-d$_6$) δ (ppm) 10.63 (s, 1H), 9.78 (d, J=4.5 Hz, 1H), 9.35 (d, J=10.0 Hz, 1H), 8.59 (d, J=10.0 Hz, 1H), 8.52 (s, 1H), 8.29 (d, J=7.5 Hz, 1H), 7.97 (t, J=10.0 Hz, 1H), 7.62 (t, J=10.0 Hz, 1H), 7.61 (d, J=4.5 Hz, 1H), 7.57 (t, J=10.0 Hz, 1H), 7.31 (d, J=8.0 Hz, 1H), 6.81 (d, J=8.0 Hz, 1H); 007 $^1$H-NMR (500 MHz, DMSO-d$_6$) δ (ppm) 10.68 (s, 1H), 8.71 (d, J=10.0 Hz, 1H), 8.65 (d, J=10.0 Hz, 1H), 8.48 (d, J=4.5 Hz, 1H), 8.21 (s, 1H), 7.97 (t, J=10.0 Hz, 1H), 7.87 (d, J=2.0 Hz, 1H), 7.71 (d, J=4.5 Hz, 1H), 7.59 (t, J=10.0 Hz, 1H), 7.57 (t, J=10.0 Hz, 1H), 7.41 (dd, J=8.5, 2.0 Hz, 1H), 6.90 (t, J=8.5 Hz, 1H). LC-MS (m/z) 350/352 ($^{79}$Br/$^{81}$Br) [M+1].

Example 5

Preparation of (Z)-3-(azulen-1-ylmethylene)-5-nitroindolin-2-one (008)

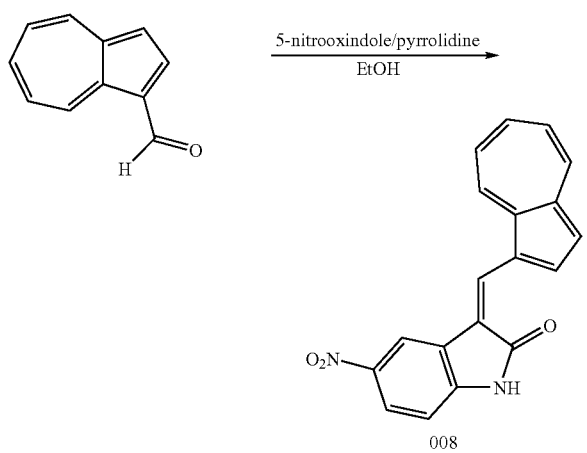

Compound 008 was prepared in a manner similar to that described in Example 1. The result was purified by column chromatography (Silica Gel 60, dichloromethane:ethyl acetate=10:1) and dried to give Compound 008.

008 $^1$H-NMR (500 MHz, DMSO-d$_6$) δ (ppm) 11.21 (s, 1H), 9.78 (d, J=4.5 Hz, 1H), 9.46 (d, J=10.0 Hz, 1H), 9.02 (d, J=2.0 Hz, 1H), 8.75 (s, 1H), 8.62 (d, J=10.0 Hz, 1H), 8.12 (dd, J=2.0, 8.5 Hz, 1H), 8.01 (t, J=10.0 Hz, 1H), 7.70 (t, J=10.0 Hz, 1H), 7.64 (d, J=7.5 Hz, 1H), 7.62 (t, J=10.0 Hz, 1H), 7.03 (t, J=8.5 Hz, 1H). LC-MS (m/z) 317 [M+1].

Example 6

Preparation of (E)-3-((4,6,8-trimethylazulen-1-yl)methylene)indolin-2-one (009)

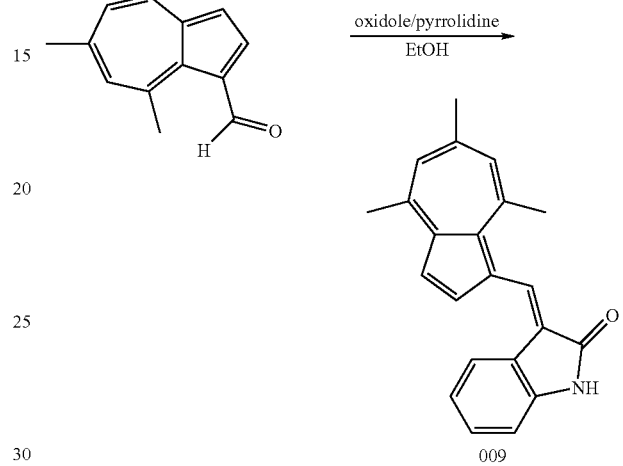

Compound 009 was prepared in a manner similar to that described in Example 1. The result was purified by column chromatography (Silica Gel 60, dichloromethane→dichloromethane:ethyl acetate=50:1→dichloromethane:ethyl acetate=25:1) and dried to give Compound 009 (513 mg, 54.6%).

009 (E) $^1$H-NMR (500 MHz, DMSO-d$_6$) δ (ppm) 10.48 (s, 1H), 8.32 (s, 1H), 7.98 (d, J=5.0 Hz, 1H), 7.67 (d, J=8.5 Hz, 1H), 7.46 (d, J=5.0 Hz), 7.30 (s, 1H), 7.26 (s, 1H), 7.18 (t, J=8.5 Hz, 1H), 6.88 (d, J=8.5 Hz, 1H), 6.79 (t, J=8.5 Hz, 1H), 3.01 (s, 3H), 2.87 (s, 3H), 2.63 (s, 3H); 009 (Z) $^1$H-NMR (500 MHz, DMSO-d$_6$) δ (ppm) 10.38 (s, 1H), 8.79 (d, J=4.5 Hz, 1H), 8.54 (s, 1H), 7.67 (d, J=7.5 Hz, 1H), 7.36 (d, J=4.5 Hz, 1H), 7.31 (s, 1H), 7.27 (s, 1H), 7.15 (t, J=7.5 Hz, 1H), 6.95 (t, J=7.5 Hz, 1H), 6.88 (d, J=7.5 Hz, 1H), 3.15 (s, 3H), 2.85 (s, 3H), 2.63 (s, 3H). LC-MS (m/z) 314 [M+1].

Example 7

Preparation of 1-Benzyl-3-((4,6,8-trimethylazulen-1-yl)methylene)indolin-2-one (010)

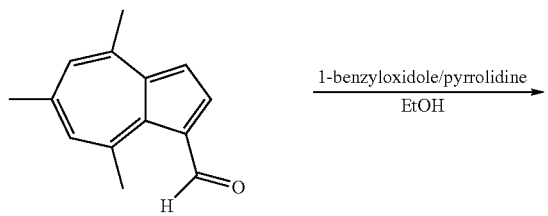

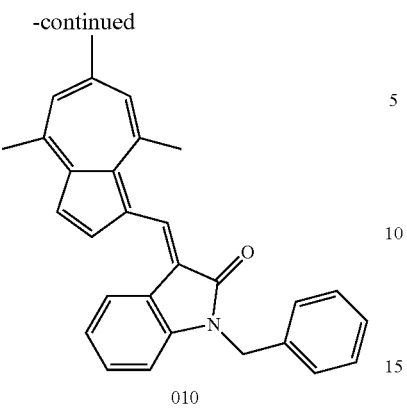

010

Compound 010 was prepared in a manner similar to that described in Example 1. The result was purified by column chromatography (Silica Gel 60, dichloromethane) and dried to give Compound 010 (430 mg, 71%).

010 $^1$H-NMR (500 MHz, CDCl$_3$) δ (ppm) 8.59 (s, 1H), 8.05 (d, J=4.5 Hz, 1H), 7.76 (d, J=7.5 Hz, 1H), 7.36-7.22 (m, 6H), 7.12 (s, 2H), 7.09 (dt, J=7.5, 1.0 Hz, 1H), 6.78 (dt, J=8.0, 1.0 Hz, 1H), 3.08 (s, 3H), 2.86 (s, 3H), 2.60 (s, 3H). LC-MS (m/z) 402 [M+1].

Example 8

Preparation of 1-Benzhydryl-3-((4,6,8-trimethylazulen-1-yl)methylene)indolin-2-one (011)

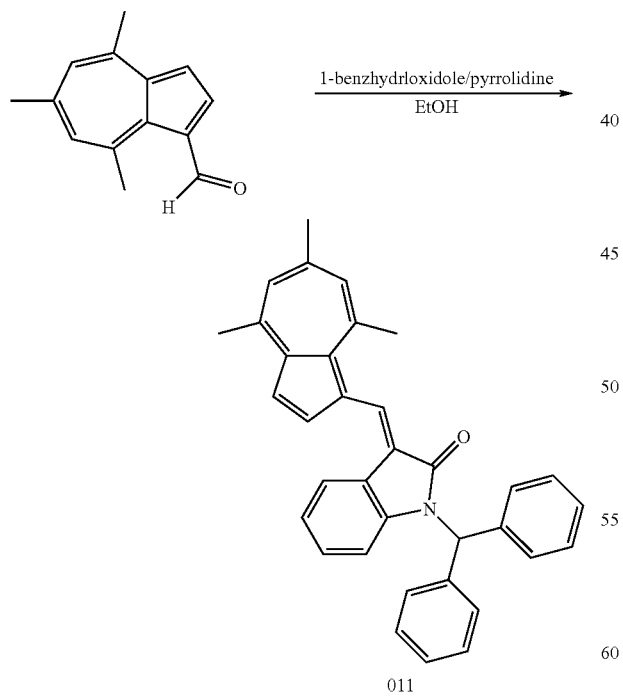

011

Compound 011 was prepared in a manner similar to that described in Example 1. The result was purified by column chromatography (Silica Gel 60, dichloromethane) and dried to give Compound 011 (344 mg, 47.8%).

011 $^1$H-NMR (500 MHz, CDCl$_3$) δ (ppm) 8.6h6 (s, 1H), 8.14 (d, J=4.0 Hz, 1H), 7.87 (d, J=7.0 Hz, 1H), 7.44-7.30 (m, 11H), 7.24 (s, 1H), 7.18 (s, 1H), 7.00-6.96 (m, 1H), 6.82-6.79 (m, 1H), 6.53 (d, J=8.0 Hz, 1H), 3.14 (s, 3H), 2.93 (s, 3H), 2.66 (s, 3H). LC-MS (m/z) 480 [M+1].

Example 9

Preparation of 3-((5-Isopropyl-3,8-dimethylazulen-1-yl)methylene)indolin-2-one (012)

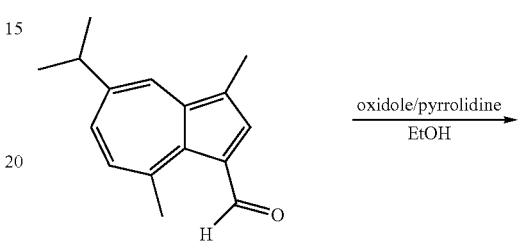

Compound 012 was prepared in a manner similar to that described in Example 2. After filtration, washing by methanol, and drying, Compound 012 (6.79 g) was obtained.

012 $^1$H-NMR (500 MHz, DMSO-d$_6$) δ (ppm) 8.84 (s, 1H), 8.55 (s, 1H), 8.14 (d, J=2.5 Hz, 1H), 8.06 (s, 1H), 7.78 (d, J=7.5 Hz, 1H), 7.40 (dd, J=1.0, 2.0 Hz, 1H), 7.16 (dt, J=7.5, 1.0 Hz, 1H), 7.10 (d, J=10.5 Hz, 1H), 6.93 (d, J=8.0 Hz, 1H), 6.83 (dt, J=8.0, 1.0 Hz, 1H), 3.09-3.06 (m, 1H), 3.06 (s, 3H), 2.62 (s, 3H), 1.37 (d, J=7.0 Hz, 6H). LC-MS (m/z) 342 [M+1].

Example 10

Preparation of 1-Benzyl-3-((5-isopropyl-3,8-dimethylazulen-1-yl)methylene)indolin-2-one (013)

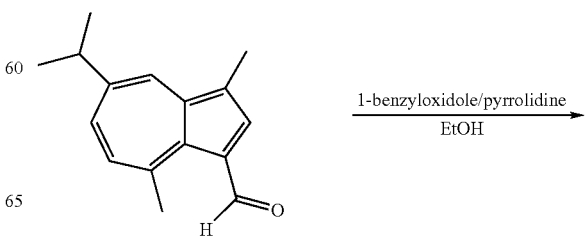

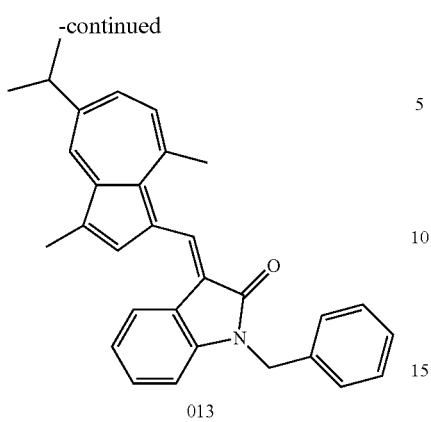
013

Compound 013 was prepared in a manner similar to that described in Example 2. After filtration, washing by methanol, and drying, Compound 013 (1.42 g) was obtained.

013 $^1$H-NMR (500 MHz, DMSO-$d_6$) δ (ppm) 8.63 (s, 1H), 8.14 (d, J=1.5 Hz, 1H), 8.07 (s, 1H), 7.81 (d, J=8.0 Hz, 1H), 7.41 (dd, J=10.5, 1.5 Hz, 1H), 7.37 (d, J=8.0 Hz, 2H), 7.31 (t, J=7.0 Hz, 2H), 7.24 (dt, J=7.5, 1.5 Hz, 1H), 7.12-7.09 (m, 2H), 6.82 (dt, J=7.5, 1.0 Hz, 1H), 6.73 (d, J=8.0 Hz, 1H), 3.07 (s, 3H), 2.63 (s, 3H), 1.37 (d, J=7.0 Hz, 6H). LC-MS (m/z) 432 [M+1].

Example 11

Preparation of 1-Benzhydryl-3-((5-isopropyl-3,8-dimethylazulen-1-yl)methylene)indolin-2-one (014)

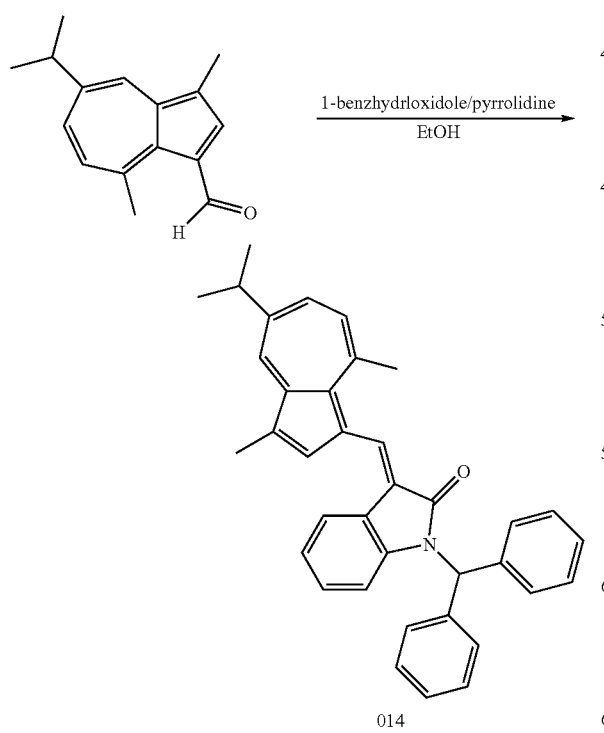
014

Compound 014 was prepared in a manner similar to that described in Example 2. After filtration, washing by methanol, and drying, Compound 014 (1.47 g) was obtained.

014 $^1$H-NMR (500 MHz, DMSO-$d_6$) δ (ppm) 8.61 (s, 1H), 8.12 (d, J=2.0 Hz, 1H), 8.07 (s, 1H), 7.82 (d, J=8.0 Hz, 1H), 7.41-7.25 (m, 11H), 7.16 (s, 1H), 7.09 (d, J=11.0 Hz, 1H), 6.91 (dt, J=7.5, 1.5 Hz, 1H), 6.75 (dt, J=7.5, 1.0 Hz, 1H), 6.46 (d, J=8.0 Hz, 1H), 3.05 (s, 3H), 2.61 (s, 3H), 1.36 (d, J=7.0 Hz, 6H). LC-MS (m/z) 508 [M+1].

Example 12

Preparation of Methyl 3-((2-oxoindolin-3-ylidene)methyl)azulene-1-carboxylate (015) and (Z)-methyl 3-((2-oxoindolin-3-ylidene)methyl)azulene-1-carboxylate (016)

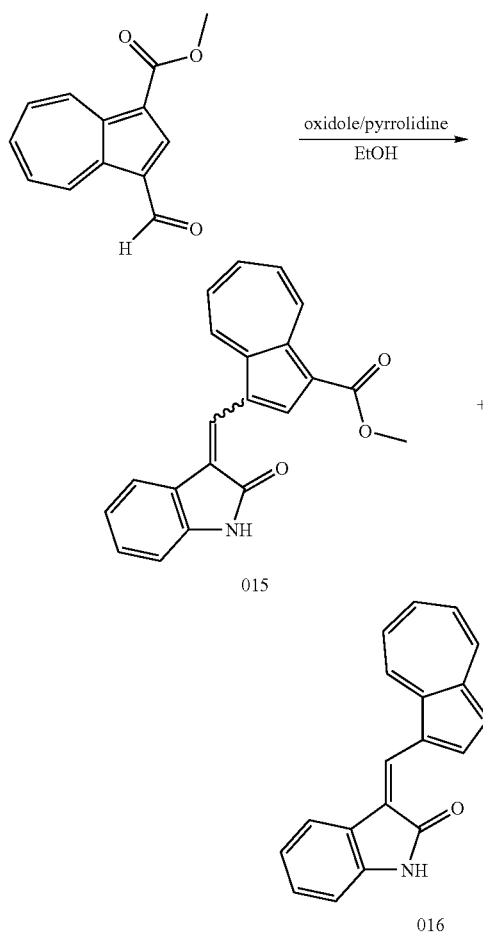

Compounds 015 and 016 were prepared in a manner similar to that described in Example 1. After removal of solvent, the results were extracted by citric acid aqueous solution and dichloromethane. The dichloromethane layer was collected, dried with anhydrous magnesium sulfate, filtered, and concentrated under vacuum to give a mixture (Compound 15, 350 mg). The aqueous layer was filtered and dried to give Compound 016 (1 g, 74%).

015 (E) (500 MHz, DMSO-$d_6$) δ (ppm) 10.60 (s, 1H), 9.66 (d, J=10.0 Hz, 1H), 8.83 (s, 1H), 8.83 (d, J=10.0 Hz, 1H), 8.16 (t, J=10.0 Hz, 1H), 8.13 (s, 1H), 7.92 (t, J=10.0 Hz, 1H), 7.83

(t, J=10.0 Hz, 1H), 7.59 (d, J=7.5 Hz, 1H), 7.26 (t, J=7.5 Hz, 1H), 6.94 (d, J=7.5 Hz, 1H), 6.91 (t, J=7.5 Hz, 1H), 3.95 (s, 3H); 015 (Z) (500 MHz, DMSO-d$_6$) δ (ppm) 10.38 (s, 1H), 10.56 (s, 1H), 10.18 (s, 1H), 9.66 (d, J=10.0 Hz, 1H), 9.40 (d, J=10.0 Hz, 1H), 8.43 (s, 1H), 8.17 (t, J=10.0 Hz, 1H), 8.02 (d, J=7.5 Hz, 1H), 7.91 (t, J=10.0 Hz, 1H), 7.88 (t, J=10.0 Hz, 1H), 7.23 (t, J=7.5 Hz, 1H), 7.06 (d, J=7.5 Hz, 1H), 6.84 (t, J=7.5 Hz, 1H); 3.96 (s, 3H) 016 (500 MHz, DMSO-d$_6$) δ (ppm) 10.38 (s, 1H), 10.56 (s, 1H), 10.18 (s, 1H), 9.66 (d, J=10.0 Hz, 1H), 9.40 (d, J=10.0 Hz, 1H), 8.43 (s, 1H), 8.17 (t, J=10.0 Hz, 1H), 8.02 (d, J=7.5 Hz, 1H), 7.91 (t, J=10.0 Hz, 1H), 7.88 (t, J=10.0 Hz, 1H), 7.23 (t, J=7.5 Hz, 1H), 7.06 (d, J=7.5 Hz, 1H), 6.84 (t, J=7.5 Hz, 1H), 3.96 (s, 3H). LC-MS (m/z) 330 [M+1].

Example 13

Preparation of (E)-3-(azulen-1-ylmethylene)indolin-2-one (019) and (Z)-3-(azulen-1-ylmethylene)indolin-2-one (020)

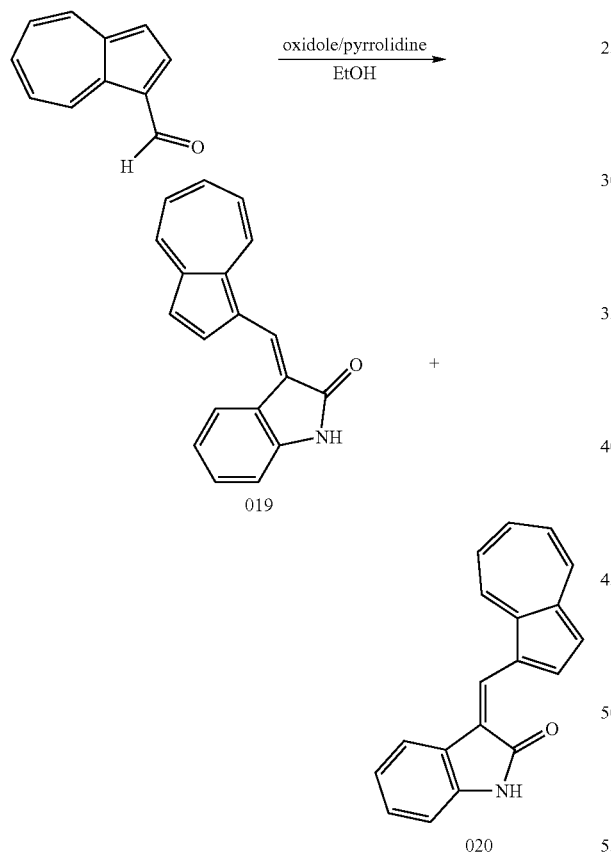

Compounds 019 and 020 were prepared in a manner similar to that described in Example 1. The results were purified by column chromatography (Silica Gel 60, dichloromethane: acetyl acetate=20:1) and dried to give Compounds 019 and 020.

019 $^1$H-NMR (500 MHz, CDCl$_3$) δ (ppm) 8.70 (d, J=10.0 Hz, 1H), 8.63 (d, J=4.5 Hz, 1H), 8.42 (s, 1H), 8.39 (s, 1H), 8.38 (d, J=10.0 Hz, 1H), 7.93 (d, J=8.0 Hz, 1H), 7.73 (t, J=10.0 Hz, 1H), 7.55 (d, J=4.5 Hz, 1H), 7.38 (t, J=10.0 Hz, 1H), 7.36 (t, J=10.0 Hz, 1H), 7.20 (t, J=8.0 Hz, 1H), 6.91 (t, J=8.0 Hz, 1H), 6.90 (t, J=8.0 Hz, 1H); 020 $^1$H-NMR (500 MHz, CDCl$_3$) δ (ppm) 9.74 (d, J=4.5 Hz, 1H), 8.70 (d, J=10.0 Hz, 1H), 7.64 (d, J=7.5 Hz, 1H), 7.42 (t, J=10.0 Hz, 1H), 7.18 (t, J=7.5 Hz, 1H), 7.06 (t, J=7.5 Hz, 1H), 6.90 (d, J=7.5 Hz, 1H), 8.40-6.80 (m, 5H). LC-MS (m/z) 272 [M+1].

Example 14

Preparation of (E)-3-(azulen-1-ylmethylene)-5-chloroindolin-2-one (022) and (Z)-3-(azulen-1-ylmethylene)-5-chloroindolin-2-one (023)

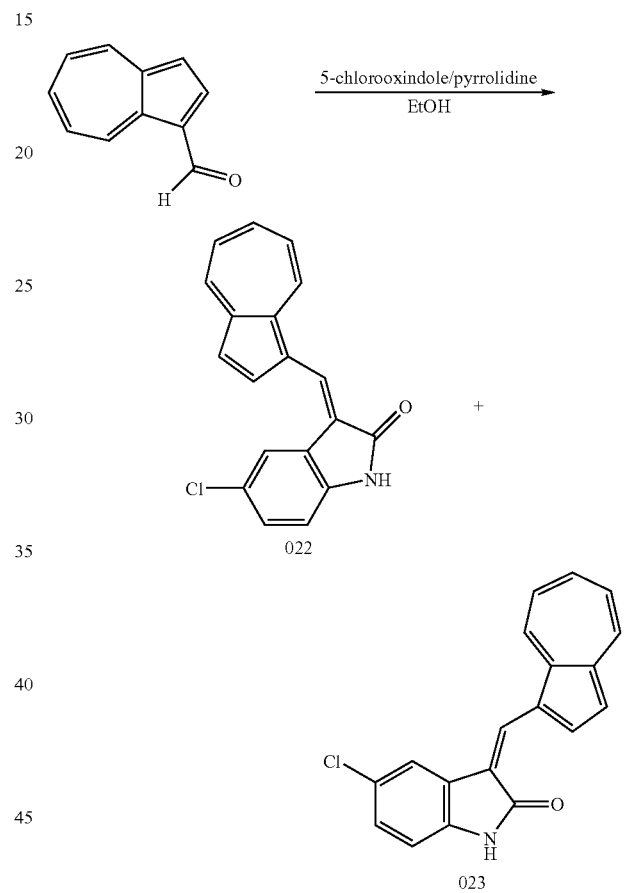

Compounds 022 and 023 were prepared in a manner similar to that described in Example 1. The results were purified by column chromatography (Silica Gel 60, dichloromethane: ethyl acetate=20:1) and dried to give Compounds 022 and 023.

022 (500 MHz, DMSO-d$_6$) δ (ppm) 10.67 (s, 1H), 8.72 (d, J=10.0 Hz, 1H), 8.65 (d, J=10.0 Hz, 1H), 8.50 (d, J=4.5 Hz, 1H), 8.28 (s, 1H), 7.98 (t, J=10.0 Hz, 1H), 7.75 (d, J=2.0 Hz, 1H), 7.71 (d, J=4.5 Hz, 1H), 7.59 (t, J=10.0 Hz, 1H), 7.58 (t, J=10.0 Hz, 1H), 7.28 (d, J=8.0 Hz, 1H), 6.94 (t, J=8.0 Hz, 1H); 023 (500 MHz, DMSO-d$_6$) δ (ppm) 10.62 (s, 1H), 9.78 (d, J=4.5 Hz, 1H), 9.35 (d, J=10.0 Hz, 1H), 8.59 (d, J=10.0 Hz, 1H), 8.52 (s, 1H), 8.17 (d, J=2.0 Hz, 1H), 7.97 (t, J=10.0 Hz, 1H), 7.63 (t, J=10.0 Hz, 1H), 7.62 (d, J=4.5 Hz, 1H), 7.57 (t, J=10.0 Hz, 1H), 7.19 (dd, J=8.0, 2.0 Hz, 1H), 6.85 (d, J=8.0 Hz, 1H). LC-MS (m/z) 306 [M+1].

Example 15

Preparation of (E)-3-(azulen-1-ylmethylene)-5-fluoroindolin-2-one (025) and (Z)-3-(azulen-1-ylmethylene)-5-fluoroindolin-2-one (026)

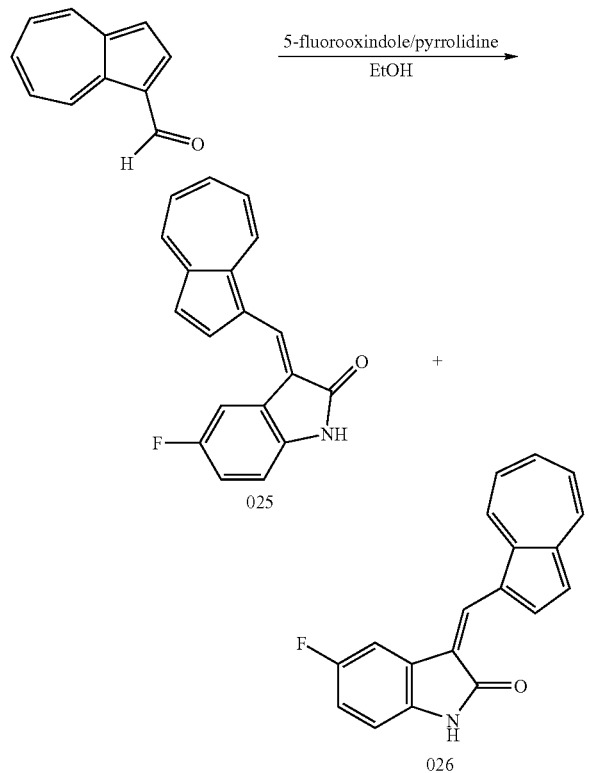

Compounds 025 and 026 were prepared in a manner similar to that described in Example 1. The results were purified by column chromatography (Silica Gel 60, dichloromethane:ethyl acetate=20:1) and dried to give Compounds 025 and 026.

025 (500 MHz, DMSO-$d_6$) δ (ppm) 10.55 (s, 1H), 8.72 (d, J=10.0 Hz, 1H), 8.64 (d, J=10.0 Hz, 1H), 8.52 (d, J=4.0 Hz, 1H), 8.28 (s, 1H), 7.96 (t, J=10.0 Hz, 1H), 7.70 (d, J=4.0 Hz, 1H), 7.59 (t, J=10.0 Hz, 1H), 7.57 (t, J=10.0 Hz, 1H), 7.59 (dd, J=9.5, 2 Hz, 1H), 7.58 (ddd, J=9.5, 7.5, 2.0 Hz, 1H), 7.57 (s, 1H), 6.90 (dd, J=7.5, 4.5 Hz, 1H); 026 (500 MHz, DMSO-$d_6$) δ (ppm) 10.50 (s, 1H), 9.79 (d, J=4.0 Hz, 1H), 9.30 (d, J=10.0 Hz, 1H), 8.58 (d, J=10.0 Hz, 1H), 8.48 (s, 1H), 7.96 (d, J=4.0 Hz, 1H), 7.95 (t, J=10.0 Hz, 1H), 7.62 (t, J=10.0 Hz, 1H), 7.61 (dd, J=9.5, 2 Hz, 1H), 7.56 (t, J=10.0 Hz, 1H), 6.97 (ddd, J=9.5, 7.5, 2.0 Hz, 1H), 6.82 (dd, J=7.5, 4.5 Hz, 1H). LC-MS (m/z) 290 [M+1].

Example 16

Preparation of 3-(((4Z,6Z,8E)-azulen-1-yl)methylene)-6-bromoindolin-2-one (028), (029)

Compounds 028 and 029 were prepared in a manner similar to that described in Example 1.

028 (500 MHz, DMSO-$d_6$) δ (ppm) 10.66 (s, 1H), 8.73 (d, J=10.0 Hz, 1H), 8.63 (d, J=10.0 Hz, 1H), 8.52 (d, J=4.5 Hz, 1H), 8.27 (s, 1H), 7.96 (t, J=10.0 Hz, 1H), 7.78 (d, J=8.0 Hz, 1H), 7.68 (d, J=4.5 Hz, 1H), 7.59 (t, J=10.0 Hz, 1H), 7.57 (t, J=10.0 Hz, 1H), 7.13 (d, J=8.0 Hz, 1H), 7.07 (s, 1H); 029 (500 MHz, DMSO-$d_6$) δ (ppm) 10.64 (s, 1H), 9.75 (d, J=4.5 Hz, 1H), 9.25 (d, J=10.0 Hz, 1H), 8.58 (d, J=10.0 Hz, 1H), 8.49 (s, 1H), 7.98 (d, J=8.5 Hz, 1H), 7.95 (t, J=10.0 Hz, 1H), 7.61 (t, J=10.0 Hz, 1H), 7.61 (d, J=4.5 Hz, 1H), 7.56 (t, J=10.0 Hz, 1H), 7.20 (d, J=8.5 Hz, 1H), 7.00 (d, J=1.0 Hz, 1H). LC-MS (m/z) 350/352 ($^{79}$Br/$^{81}$Br) [M+1].

Example 17

Preparation of 3-(((4Z,6Z,8E)-azulen-1-yl)methylene)-6-methoxyindolin-2-one (030), (031)

Compounds 030 and 031 were prepared in a manner similar to that described in Example 1.

030 (500 MHz, DMSO-$d_6$) δ (ppm) 10.48 (s, 1H), 8.65 (d, J=9.5 Hz, 1H), 8.59 (d, J=9.5 Hz, 1H), 8.49 (d, J=4.0 Hz, 1H), 8.04 (s, 1H), 7.89 (t, J=9.5 Hz, 1H), 7.74 (d, J=8.5 Hz, 1H), 7.64 (d, J=4.0 Hz, 1H), 7.48 (t, J=9.5 Hz, 1H), 7.47 (t, J=9.5 Hz, 1H), 6.51 (d, J=8.0 Hz, 1H), 6.50 (s, 1H), 3.81 (s, 3H); 031 (500 MHz, DMSO-$d_6$) δ (ppm) 10.46 (s, 1H), 9.69 (d, J=4.0 Hz, 1H), 9.14 (d, J=10.0 Hz, 1H), 8.57 (d, J=10.0 Hz, 1H), 8.26 (s, 1H), 7.88 (d, J=8.5 Hz, 1H), 7.86 (t, J=10.0 Hz, 1H), 7.57 (d, J=4.0 Hz, 1H), 7.52 (t, J=10.0 Hz, 1H), 7.47 (t, J=10.0 Hz, 1H), 6.60 (dd, J=8.0, 2.0 Hz, 1H), 7.00 (d, J=2.0 Hz, 1H), 3.81 (s, 3H). LC-MS (m/z) 302 [M+1].

Example 18

Preparation of 3-(((3aZ,5Z,7Z)-azulen-2-yl)methylene)indolin-2-one (032), (033)

Compounds 032 and 033 were prepared in a manner similar to that described in Example 1.

032 (500 MHz, DMSO-$d_6$) δ (ppm) 10.61 (s, 1H), 8.49 (d, J=10.0 Hz, 2H), 8.10 (d, J=7.5 Hz, 1H), 7.90 (s, 1H), 7.78 (s, 2H), 7.72 (d, J=10.0 Hz, 1H), 7.30 (t, J=10.0 Hz, 2H), 7.29 (t, J=7.5 Hz, 1H), 6.96 (t, J=7.5 Hz, 1H), 6.91 (d, J=7.5 Hz, 1H). (500 MHz, DMSO-$d_6$) δ (ppm); 033 10.63 (s, 1H), 8.42 (d, J=10.0 Hz, 2H), 8.27 (s, 2H), 8.10 (s, 1H), 7.77 (d, J=7.5 Hz, 1H), 7.65 (t, J=10.0 Hz, 1H), 7.24 (t, J=7.5 Hz, 1H), 7.22 (t, J=10.0 Hz, 2H), 7.01 (t, J=7.5 Hz, 1H), 6.85 (d, J=7.5 Hz, 1H). LC-MS (m/z) 272 [M+1].

Example 19

Preparation of (3Z)-3-(((4Z,6Z,8E)-azulen-1-yl)methylene)-5-phenylindolin-2-one (034)

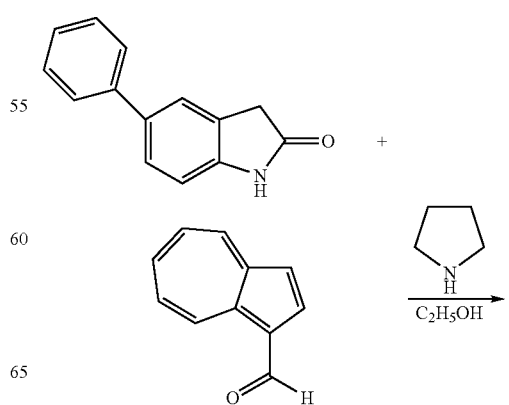

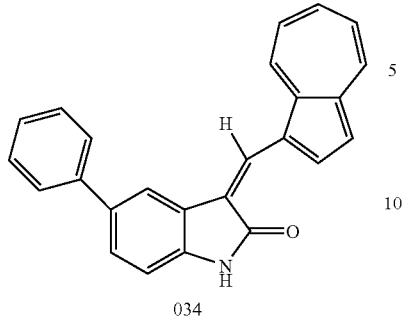

034

0.4389 g 5-phenyloxindole (0.0021 mole) and 0.323 g azulene aldehyde (0.0021 mole) were dissolved in 30 mL dried ethanol. 1.5 mL pyrrolidine (1M) was then added and uniformly stirred at reflux temperature for two hours. After removal of dried ethanol, the results were extracted by dichloromethane and citric acid aqueous solution. The organic layer was collected, dried with anhydrous magnesium sulfate, filtered, concentrated under vacuum, and separated by silica gel column chromatography to give Z-form Compound 034 (0.1621 g).

034 (500 MHz, DMSO-$d_6$) δ (ppm) 10.59 (s, 1H), 9.81 (d, J=4.0 Hz, 1H), 9.32 (d, J=10.0 Hz, 1H), 8.58 (s, 1H), 8.57 (d, J=10.0 Hz, 1H), 8.34 (d, J=2.0 Hz, 1H4), 7.94 (t, J=10.0 Hz, 1H), 7.79 (dd, J=7.5, 1.0 Hz, 2H), 7.62 (d, J=4.0 Hz, 1H), 7.61 (t, J=10.0 Hz, 1H), 7.54 (t, J=10.0 Hz, 1H), 7.51 (t, J=7.5 Hz, 2H), 7.49 (dd, J=8.0, 2.0 Hz, 1H), 7.37 (tt, J=7.5, 1.0 Hz, 2H), 6.95 (d, J=8.0 Hz, 1H). LC-MS (m/z) 348 [M+1].

Example 20

Preparation of (3E)-3-(((4Z,6Z,8E)-2-(dimethylamino)cyclohepta[b]pyrrol-3-yl)methylene)indolin-2-one IPA (035)

20 mg (4Z,6Z,8E)-2-(dimethylamino)cyclohepta[b]pyrrole-3-carbaldehyde, 25 mg oxindole, and 0.1 mg piperidine were added in IPA with reflux for 20 hours. After cooling, red crystals were precipitated. After filtration and washing by IPA, Compound 035 was obtained (55%).

035 $^1$H-NMR (500 MHz, CDCl$_3$) δ (ppm) 8.25 (b, 1H), 8.19 (s, 1H), 7.57 (m, 1H). 7.37 (m, 1H), 7.35 (m, 2H), 7.26 (s, 1H), 7.15 (t, 1H), 6.90 (d, J=5 Hz, 2H), 6.77 (t, 1H), 6.56 (d, J=5 Hz, 1H). 4.02 (m, 1H, IPA). 3.42 (s, 6H, IPA). LC-MS (m/z) 316 [M+1].

Example 21

Preparation of (3E)-3-(((4Z,6Z,8Z)-1-methylazulen-3-yl)methylene)indolin-2-one (036) and 3-(((3aZ,5Z,7Z)-1-methylazulen-3-yl)methylene)indolin-2-one (037)

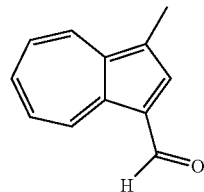

oxindole/pyrrolidine
——————→
EtOH

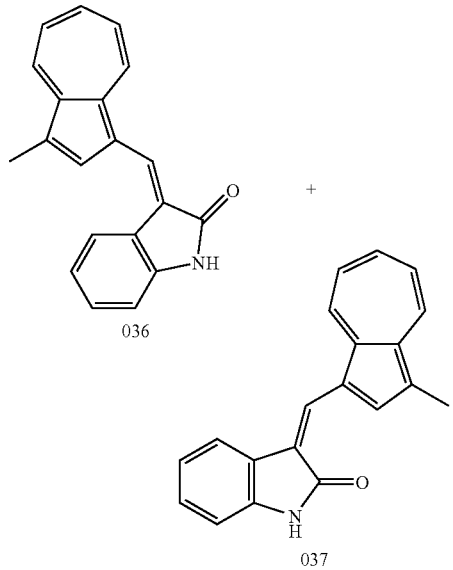

036

037

Compounds 036 and 037 were prepared in a manner similar to that described in Example 1. The results were extracted by 150 mL ethyl acetate and 50 mL water. The ethyl acetate layer was collected, dried with anhydrous magnesium sulfate, filtered, and concentrated under vacuum. The residue was then purified by column chromatography (Silica Gel 60, dichloromethane) and dried to give Compounds 036 and 037.

036 (500 MHz, DMSO-$d_6$) δ (ppm) 10.50 (s, 1H), 8.59 (d, J=10.0 Hz, 1H, 8.46 (d, J=10.0 Hz, 1H), 8.40 (s, 1H), 8.17 (s, 1H), 7.91 (d, J=7.5 Hz, 1H), 7.86 (t, J=10.0 Hz, 1H), 7.45 (t, J=10.0 Hz, 1H), 7.44 (t, J=10.0 Hz, 1H), 7.24 (t, J=7.5 Hz, 1H), 6.96 (t, J=7.5 Hz, 1H), 6.93 (t, J=8.0 Hz, 1H), 2.72 (s, 3H); 037 (Z) (500 MHz, DMSO-$d_6$) 10.48 (s, 1H), 9.62 (s, 1H), 9.10 (d, J=10.0 Hz, 1H), 8.42 (d, J=10.0 Hz, 1H), 8.36 (s, 1H), 7.97 (d, J=7.5 Hz, 1H), 7.86 (t, J=10.0 Hz, 1H), 7.45 (t, J=10.0 Hz, 1H), 7.44 (t, J=10.0 Hz, 1H), 7.17 (t, J=7.5 Hz, 1H), 7.03 (t, J=7.5 Hz, 1H), 6.85 (t, J=8.0 Hz, 1H), 2.68 (s, 3H); 037 (E) (500 MHz, DMSO-$d_6$) δ (ppm) 10.50 (s, 1H), 8.59 (d, J=10.0 Hz, 1H), 8.46 (d, J=10.0 Hz, 1H), 8.40 (s, 1H), 8.17 (s, 1H), 7.91 (d, J=7.5 Hz, 1H), 7.86 (t, J=10.0 Hz, 1H), 7.45 (t, J=10.0 Hz, 1H), 7.44 (t, J=10.0 Hz, 1H), 7.24 (t, J=7.5 Hz, 1H), 6.96 (t, J=7.5 Hz, 1H), 6.93 (t, J=8.0 Hz, 1H), 2.72 (s, 3H). LC-MS (m/z) 286 [M+1].

Example 22

Preparation of (3E)-5-fluoro-3-(((4Z,6Z,8Z)-1-methylazulen-3-yl)methylene)indolin-2-on (038) and (3Z)-5-fluoro-3-(((3aZ,5Z,7Z)-1-methylazulen-3-yl)methylene)indolin-2-one (039)

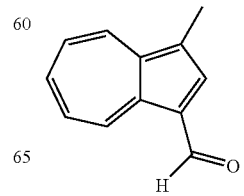

5-fluorooxindole/pyrrolidine
————————→
EtOH

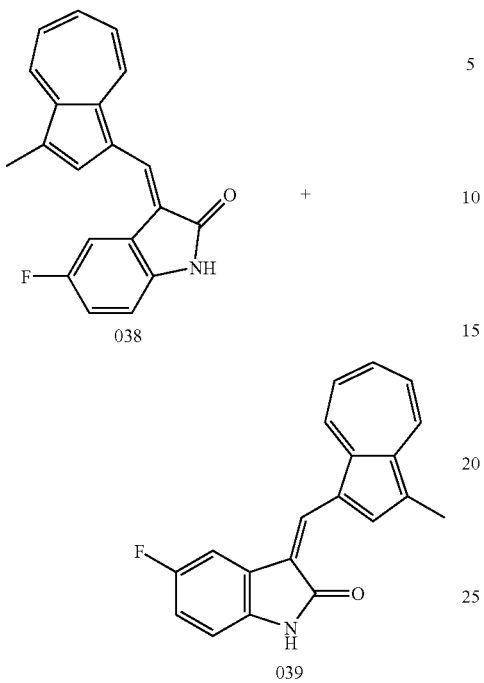

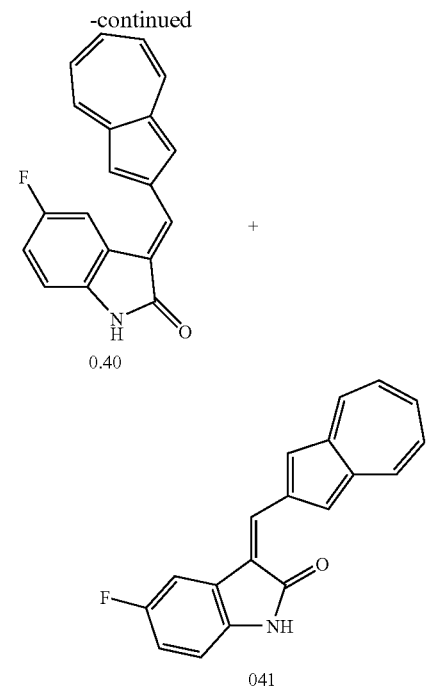

Compounds 038 and 039 were prepared in a manner similar to that described in Example 1. The results were extracted by 150 mL ethyl acetate and 50 mL water. The ethyl acetate layer was collected, dried with anhydrous magnesium sulfate, filtered, and concentrated under vacuum. The residue was then purified by column chromatography (Silica Gel 60, dichloromethane) and dried to give Compounds 038 (54 mg) and 039 (40 mg).

038 (500 MHz, DMSO-$d_6$) δ (ppm) 10.53 s, 1H), 8.61 (d, J=10.0 Hz, 1H), 8.49 (d, J=10.0 Hz, 1H), 8.37 (s, 1H), 8.23 (s, 1H), 7.89 (t, J=10.0 Hz, 1H), 7.59 (d, J=9.5 Hz, 1H), 7.49 (t, J=10.0 Hz, 1H), 7.48 (t, J=10.0 Hz, 1H), 7.07 (dd, J=9.5, 8.0 Hz, 1H), 6.91 (dd, J=8.0, 5.0 Hz, 1H), 2.72 (s, 3H); 039 (500 MHz, DMSO-$d_6$) δ (ppm) 10.48 (s, 1H), 9.63 (s, 1H), 9.20 (d, J=9.5 Hz, 1H), 8.45 (d, J=9.5 Hz, 1H), 8.41 (s, 1H), 7.94 (dd, J=9.5, 2.5 Hz, 1H), 7.89 (t, J=9.5 Hz, 1H), 7.52 (t, J=9.5 Hz, 1H), 7.50 (t, J=9.5 Hz, 1H), 6.96 (ddd, J=9.5, 7.5, 2.5 Hz, 1H), 6.81 (dd, J=7.5, 4.5 Hz, 1H), 2.68 (s, 3H). LC-MS (m/z) 304 [M+1].

Example 23

Preparation of (3E)-3-(((4Z,6Z,8Z)-azulen-2-yl)methylene)-5-fluoroindolin-2-one (040) and (3Z)-3-(((4Z,6Z,8Z)-azulen-2-yl)methylene)-5-fluoroindolin-2-one (041)

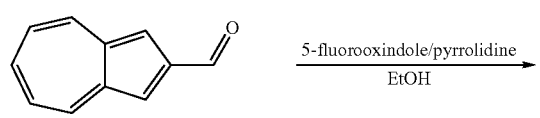

Compounds 040 and 041 were prepared in a manner similar to that described in Example 1. After removal of partial solvent, filtration, washing by methanol, and drying, Compound 040 (194 mg) was obtained. After purification by column chromatography (Silica Gel 60, ethyl acetate/n-hexane=1:3) and drying, Compounds 041 (9 mg) was obtained.

040 (500 MHz, DMSO-$d_6$) δ (ppm) 10.66 (s, 1H), 8.55 (d, J=9.5 Hz, 2H), 8.00 (s, 1H), 7.84 (d, J=7.5 Hz, 1H), 7.80 (s, 2H), 7.77 (t, J=9.5 Hz, 1H), 7.35 (t, J=9.5 Hz, 2H7), 7.17 (t, J=7.5 Hz, 1H), 6.93 (dd, J=7.5, 4.5 Hz, 1H); 041 (500 MHz, DMSO-$d_6$) δ (ppm) 10.66 (s, 1H), 8.47 (d, J=9.5 Hz, 2H), 7.29 (s, 2H), 8.22 (s, 1H), 7.74 (dd, J=9.0, 2.5 Hz, 1H), 7.70 (t, J=9.5 Hz, 1H), 7.26 (t, J=9.5 Hz, 2H), 7.09 (ddd, J=9.0, 8.5, 2.5 Hz, 1H), 6.85 (dd, J=8.5, 4.5 Hz, 1H). LC-MS (m/z) 290 [M+1].

Example 24

Preparation of (Z)-3-(azulen-1-ylmethylene)-7-chloroindolin-2-one (042)

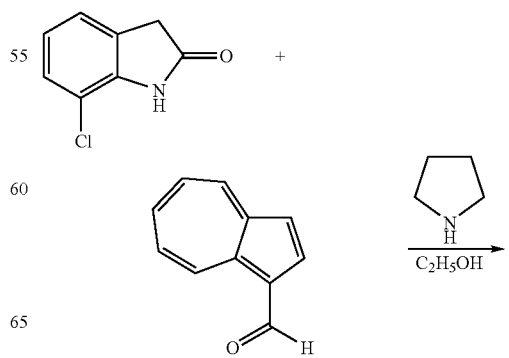

-continued

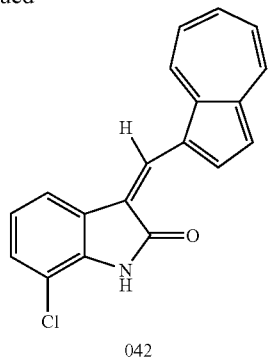

042

0.3519 g 7-chlorooxindole (0.0021 mole) and 0.323 g azulene aldehyde (0.0021 mole) were dissolved in 30 mL dried ethanol. 1.5 mL pyrrolidine (1M) was then added and uniformly stirred at reflux temperature for two hours. After removal of dried ethanol, the results were extracted by dichloromethane and citric acid aqueous solution. The organic layer was collected, dried with anhydrous magnesium sulfate, filtered, concentrated under vacuum, and separated by silica gel column chromatography to give Z-form Compound 042 (0.3693 g). The total weight of 7-chlorooxindole-azulene was 0.3693 g (57.56%).

042 (500 MHz, DMSO-$d_6$) δ (ppm) 10.89 (s, 1H), 9.75 (d, J=4.5 Hz, 1H), 9.25 (d, J=10.0 Hz, 1H), 8.57 (d, J=10.0 Hz, 1H), 8.48 (s, 1H), 7.97 (d, J=7.5 Hz, 1H), 7.94 (t, J=10.0 Hz, 1H), 7.61 (t, J=10.0 Hz, 1H), 7.60 (d, J=4.5 Hz, 1H), 7.55 (t, J=10.0 Hz, 1H), 7.20 (d, J=7.5 Hz, 1H), 7.03 (d, J=7.5 Hz, 1H). LC-MS (m/z) 306 [M+1].

Example 25

Preparation of (E)-3-(azulen-1-ylmethylene)-5-methoxyindolin-2-one (043) and (3Z)-3-(((4Z,6Z,8E)-azulen-1-yl)methylene)-5-methoxyindolin-2-one (044)

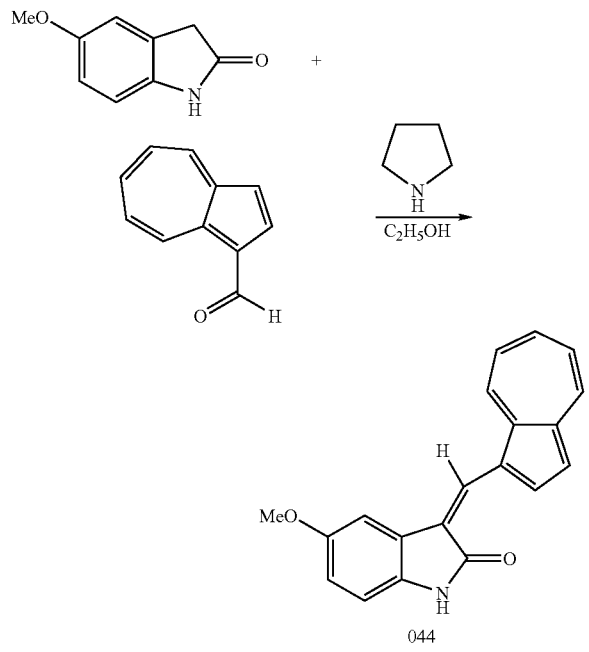

044

0.3759 g 5-methoxyoxindole (0.0021 mole) and 0.323 g azulene aldehyde (0.0021 mole) were dissolved in 30 mL dried ethanol. 1.5 mL pyrrolidine (1M) was then added and uniformly stirred at reflux temperature for two hours. After removal of dried ethanol, the results were extracted by dichloromethane and citric acid aqueous solution. The organic layer was collected, dried with anhydrous magnesium sulfate, filtered, concentrated under vacuum, and separated by silica gel column chromatography to give E-form Compound 043 (0.1472 g), Z-form Compound 044 (0.0179 g), and E/Z form compound (0.0816 g). The total weight of 5-methoxyoxindole-azulene was 0.2467 g (39.03%).

43 (500 MHz, DMSO-$d_6$) δ (ppm) 10.30 (s, 1H), 8.64 (d, J=9.5 Hz, 1H), 8.59 (d, J=9.5 Hz, 1H), 8.50 (d, J=4.0 Hz, 1H), 8.17 (s, 1H), 7.91 (t, J=9.5 Hz, 1H), 7.65 (d, J=4.0 Hz, 1H), 7.52 (t, J=9.5 Hz, 1H), 7.51 (t, J=9.5 Hz, 1H), 7.34 (s, 1H), 6.82 (s, 1H), 6.81 (s, 1H), 3.69 (s, 3H); 044 (500 MHz, DMSO-$d_6$) δ (ppm) 10.27 (s, 1H), 9.76 (d, J=4.0 Hz, 1H), 9.23 (d, J=9.5 Hz, 1H), 8.53 (d, J=9.5 Hz, 1H), 8.39 (s, 1H), 7.90 (t, J=9.5 Hz, 1H), 7.65 (s, 1H), 7.57 (d, J=4.0 Hz, 1H), 7.56 (t, J=9.5 Hz, 1H), 7.50 (t, J=9.5 Hz, 1H), 6.74 (s, 1H), 6.73 (s, 1H), 3.82 (s, 3H). LC-MS (m/z) 302 [M+1].

Example 26

Preparation of (3Z)-3-(((3aZ,5Z,7Z)-1-bromoazulen-3-yl)methylene)-5-fluoroindolin-2-one (045)

Compound 045 was prepared in a manner similar to that described in Example 19.

045 (500 MHz, DMSO-$d_6$) δ (ppm) 10.58 (s, 1H), 9.84 (s, 1H), 9.32 (d, J=10.0 Hz, 1H), 8.46 (d, J=10.0 Hz, 1H), 8.40 (s, 1H), 8.03 (t, J=10.0 Hz, 1H), 7.95 (d, J=8.5 Hz, 1H), 7.67 (t, J=10.0 Hz, 1H), 7.66 (t, J=10.0 Hz, 1H), 6.96 (dd, J=10.0, 8.5 Hz, 1H), 6.81 (dd, J=8.5, 4.5 Hz, 1H). LC-MS (m/z) 368/370 ($^{79}$Br/$^{81}$Br) [M+1].

Example 27

Preparation of (3Z)-3-(((3aZ,5Z,7Z)-1-chloroazulen-3-yl)methylene)-5-fluoroindolin-2-one (046)

Compound 046 was prepared in a manner similar to that described in Example 31. 129 mg 5-fluoro-2-oxindole (0.853 mmol), 162.6 mg 1-chloro-3-aldehyde azulene (0.853 mmol), 3 drops piperidine, and 20 mL ethanol were mixed with reflux for 2 hours. After removal of ethanol, the result was purified by silica gel column chromatography (DCM) to give Compound 046 (87.3 mg, 0.269 mmol, 31.6%).

046 (500 MHz, DMSO-$d_6$) δ (ppm) $^1$H, 10.601 (s, 1H), 9.792 (s, 1H), 9.362 (d, 1H, J=10 Hz), 8.534 (d, 1H, J=9.5 Hz), 8.449 (s, 1H), 8.053 (t, 1H, J=10 Hz), 7.982 (dd, 1H, J=2.5, 9.5 Hz), 7.670 (t, 2H, J=10 Hz), 7.003 (m, 1H), 6.832 (dd, 1H, J=4.5, 8.5 Hz). LC-MS (m/z) 324 [M+1].

Example 28

Preparation of (3E)-3-(((3aZ,5Z,7Z)-azulen-1-yl)methylene)-5-methylindolin-2-one (047), (048)

Compounds 047 and 048 were prepared in a manner similar to that described in Example 19.

047 (500 MHz, DMSO-$d_6$) δ (ppm) 10.40 (s, 1H), 8.69 (d, J=9.5 Hz, 1H), 8.61 (d, J=9.5 Hz, 1H), 8.55 (d, J=4 Hz, 1H), 8.18 (s, 1H), 7.93 (t, J=9.5 Hz, 1H), 7.68 (d, J=4.0 Hz, 1H), 7.66 (s, 1H), 7.52 (t, J=9.5 Hz, 1H), 7.51 (t, J=9.5 Hz, 1H), 7.05 (d, J=7.5 Hz, 1H), 6.82 (d, J=7.5 Hz, 1H), 2.26 (s, 3H);

048 δ (ppm) 10.39 (s, 1H), 9.77 (d, J=4.0 Hz, 1H), 9.22 (d, J=9.5 Hz, 1H), 8.56 (d, J=9.5 Hz, 1H), 8.38 (s, 1H), 7.94 (t, J=9.5 Hz, 1H), 7.83 (s, 1H), 7.60 (d, J=4.0 Hz, 1H), 7.58 (t, J=9.5 Hz, 1H), 7.52 (t, J=9.5 Hz, 1H), 6.99 (d, J=8.0 Hz, 1H), 6.75 (d, J=8.0 Hz, 1H), 2.53 (s, 3H). LC-MS (m/z) 286 [M+1].

Example 29

Preparation of (3E)-3-(((3aZ,5Z,7Z)-azulen-1-yl)methylene)-5-(N,N-dimethylsulfonyl)indolin-2-one (049)

Compound 049 was prepared in a manner similar to that described in Example 19.

049 (500 MHz, DMSO-$d_6$) δ (ppm) 11.00 (s, 1H), 9.80 (d, J=4.0 Hz, 1H, 9.41 (d, J=9.5 Hz, 1H), 8.68 (s, 1H), 8.61 (d, J=9.5 Hz, 1H), 8.43 (s, 1H), 7.99 (t, J=9.5 Hz, 1H), 7.68 (t, J=9.5 Hz, 1H), 7.64 (d, J=4.0 Hz, 1H), 7.63 (d, J=8.0 Hz, 1H), 7.58 (t, J=9.5 Hz, 1H), 7.06 (d, J=8.0 Hz, 1H), 2.69 (s, 6H).

Example 30

Preparation of 3-Azulen-1-ylmethylene-2-oxo-2,3-dihydro-1H-indole-5-sulfonicacid dimethylamide (050)

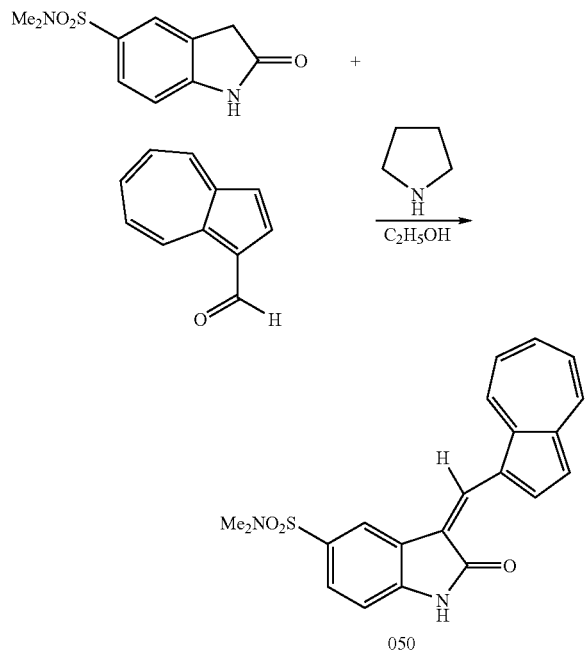

0.504 g 2-Oxo-2,3-dihydro-1H-indole-5-sulfonic acid dimethylamide (0.0021 mole) and 0.323 g azulene aldehyde (0.0021 mole) were dissolved in 30 mL dried ethanol. 1.5 mL pyrrolidine (1M) was then added and uniformly stirred at reflux temperature for two hours. After removal of dried ethanol, the results were extracted by dichloromethane and citric acid aqueous solution. The organic layer was collected, dried with anhydrous magnesium sulfate, filtered, concentrated under vacuum, and separated by silica gel column chromatography to give Compound 050 (E-form (0.0548 g), Z-form (0.1376 g)).

Example 31

Preparation of (3E)-3-(((4Z,6Z,8E)-1-bromoazulen-3-yl)methylene)-5-fluoroindolin-2-one (051)

18.5 mg 5-fluoro-2-oxindole (0.122 mmol), 40.8 mg 1-bromo-3-aldehyde azulene (0.122 mmol), 3 drops piperidine, and 20 mL ethanol were mixed with reflux for 2 hours. After removal of ethanol, the result was purified by silica gel column chromatography (DCM) to give Compound 051 (57 mg, 0.122 mmol, 100%).

051 (500 MHz, DMSO-$d_6$) δ (ppm) $^1$H, 10.576 (s, 1H), 9.841 (s, 1H), 9.320 (d, 1H, J=10 Hz), 8.460 (d, 1H, J=10 Hz), 8.400 (s, 1H), 8.030 (t, 1H, 10 Hz), 7.951 (d, 2H, 8.5 Hz), 7.443 (dd, 1H, J+2, 16 Hz), 6.799 (t, 1H, J=4.5 Hz). LC-MS (m/z) 369 [M+1].

Example 32

Preparation of (3E)-3-(((3aZ,5Z,7Z)-azulen-8-yl)methylene)-5-fluoroindolin-2-one (052)

Compound 052 was prepared in a manner similar to that described in Example 31. 47.2 mg 5-fluoro-2-oxindole (0.312 mmol), 48.7 mg 4-aldehyde azulene (0.3127 mmol), 3 drops piperidine, and 20 mL ethanol were mixed with reflux for 2 hours. After removal of ethanol, the result was purified by silica gel column chromatography (DCM) to give Compound 052 (81.6 mg, 0.282 mmol, 90.4%).

052 (500 MHz, CDCl$_3$) δ (ppm) $^1$H, 10.741 (s, 1H), 8.594 (d, 1H, J=9.5 Hz), 8.242 (s, 1H), 7.921 (t, 1H, J=3.5 Hz), 7.798 (t, 1H, J=10.5 Hz), 7.557 (d, 1H, J=3.5 Hz), 7.470 (d, 1H, J=5 Hz), 7.412 (t, 1H, J=9.5 Hz), 7.297 (d, 1H, J=3.5 Hz), 7.033 (m, 1H), 6.862 (dd, J=4, 8.5 Hz), 6.217 (dd, 1H, J=2.5, 9 Hz). LC-MS (m/z) 290 [M+1].

Example 33

Preparation of (3E)-3-(((3aZ,5E,7Z)-azulen-6-yl)methylene)-5-fluoroindolin-2-one (053)

Compound 053 was prepared in a manner similar to that described in Example 31. 55.61 mg 5-fluoro-2-oxindole (0.36 mmol), 57.4 mg 6-aldehyde azulene (0.36 mmol), 3 drops piperidine, and 20 mL ethanol were mixed with reflux for 2 hours. After removal of ethanol, the result was purified by silica gel column chromatography (DCM) to give Compound 053 (48.2 mg, 45%).

053 (500 MHz, DMSO-$d_6$) δ (ppm) $^1$H, 8.398 (d, 2H, J=10 Hz), 8.041 (s, 1H), 8.006 (t, 1H, J=3.5 Hz), 7.673 (s, 1H), 7.513-7.437 (m, 4H), 7.313 (dd, 1H, J=2.5, 9.5 Hz), 6.968-6.929 (m, 1H), 6.806 (dd, 1H, J=4, 8 Hz). LC-MS (m/z) 290 [M+1].

Example 34

Preparation of 3-(((4Z,6Z,8E)-2-aminocyclohepta[b]pyrrol-3-yl)methylene)-5-methylindolin-2-one (054), (055)

Compounds 054 and 055 were prepared in a manner similar to that described in Example 31. 46 mg 5-methyl-2-oxindole, 39.3 mg (4Z,6Z,8E)-2-aminocyclohepta[b]pyrrole-3- carbaldehyde, 3 drops piperidine, and 20 mL ethanol were mixed with reflux for 2 hours. After removal of ethanol, the result was purified by silica gel column chromatography (EA/methanol=5:1) to give Compounds 054 and 055.

054 (500 MHz, DMSO-$d_6$) δ (ppm) $^1$H 10.45 (s, 1H), 8.23 (b, 1H), 7.99 (s, 1H)), 7.98 (d, 1H), 7.84 (d, 1H), 7.63 (t, 1H), 7.49 (m, 2H), 7.58 (d, 1H), 6.89 (d, 1H, J=5 Hz), 6.79 (d, 1H), 2.01 (s, 3H); 055 10.43 (s, 1H), 7.88 (d, 1H), 7.84 (s, 1H)), 7.62 (m, 1H), 7.59 (b, 1H), 7.42 (m, 1H), 7.20 (m, 1H), 7.00 (d, 1H, J=5 Hz), 6.79 (d, 1H, J=5 Hz), 6.23 (s, 1H), 2.28 (s, 3H). LC-MS (m/z) 302 [M+1].

Example 35

Preparation of (3E)-5-fluoro-3-(((3aZ,5Z,7Z)-1-fluoroazulen-2-yl)methylene)indolin-2-one (056) and (3Z)-5-fluoro-3-(((3aZ,5Z,7Z)-1-fluoroazulen-3-yl)methylene)indolin-2-one (060)

Compounds 056 and 060 were prepared in a manner similar to that described in Example 31. 23.71 mg 5-fluoro-2-oxindole (0.156 mmol), 27.3 mg 1-fluoro-3-aldehyde azulene (0.156 mmol), 3 drops piperidine, and 20 mL ethanol were mixed with reflux for 2 hours. After removal of ethanol, the result was purified by silica gel column chromatography (EA/methanol=5:1) to give Compounds 056 and 060 (31.06 mg, 64.8%).

056 (500 MHz, DMSO-$d_6$) $^1$H 10.542 (s, 1H), 9.508 (s, 1H), 9.319 (d, 1H, J=9.5 Hz), 8.455 (s, 1H), 8.439 (d, 1H, J=10 Hz), 7.945 (m, 2H), 7.508 (t, 1H, J=10 Hz), 7.462 (t, 1H, J=9.5 Hz), 6.956 (m, 1H), 6.801 (dd, 1H, J=4.5, 8.5 Hz); 060 $^1$H 10.542 (s, 1H), 9.508 (s, 1H), 9.319 (d, 1H, J=9.5 Hz), 8.455 (s, 1H), 8.439 (d, 1H, J=10 Hz), 7.964-7.928 (m, 2H), 7.528-7.443 (m, 2H), 6.985-6.945 (m, 1H), 6.801 (dd, 1H, J=4.5, 8.5 Hz). LC-MS (m/z) 308 [M+1].

Example 36

Preparation of (3Z)-3-(((3aZ,5Z,7Z)-1-((dimethylamino)methyl)azulen-3-yl)methylene)indolin-2-one (058)

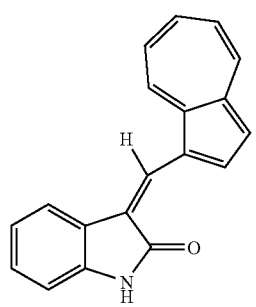

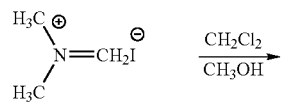

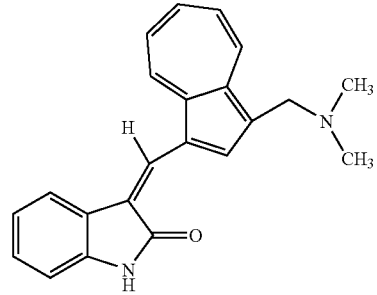

058

0.01 g N,N-Dimethylmethyleneammonium Iodide, 10 mL methanol, 2 mL dichloromethane, 0.01 g 3-Azulen-1-ylmethylene-1,3-dihydro-indol-2-one, and 0.1 mL acetic acid were mixed and uniformly stirred at reflux temperature for a period of time. After removal of methanol, the results were extracted by acetyl acetate and sodium bicarbonate aqueous solution. The organic layer was collected, dried with anhydrous magnesium sulfate, filtered, and concentrated under vacuum to give Compound 058.

Example 37

Preparation of (3Z)-3-(((3aZ,5Z,7Z)-1-((dimethylamino)methyl)azulen-3-yl)methylene)-5-fluoroindolin-2-one (059)

0.1053 g N,N-Dimethylmethyleneammonium Iodide, 10 mL methanol, 2 mL dichloromethane, 0.0147 g 3-Azulen-1-ylmethylene-5-fluoro-1,3-dihydro-indol-2-one, and 0.1 mL acetic acid were mixed and uniformly stirred at reflux temperature for a period of time. After removal of methanol, the results were extracted by ethyl acetate and sodium bicarbonate aqueous solution. The organic layer was collected, dried with anhydrous magnesium sulfate, filtered, and concentrated under vacuum to give Compound 059 (0.0042 g). LC-MS (m/z) 347 [M+1].

Example 38

Preparation of (3Z)-5-fluoro-3-(((4Z,6Z,8E)-2-oxo-2H-cyclohepta[b]furan-3-yl)methylene)indolin-2-one (062)

Compound 062 was prepared in a manner similar to that described in Example 31.

062 (E form) (500 MHz, CD$_3$OD) δ (ppm) $^1$H 9.217 (s, 1H), 8.500 (d, 1H, J=9.5 Hz), 8.266 (s, 1H), 8.044 (s, 1H), 7.994 (dd, 1H, J=5.5, 8.5 Hz), 7.717 (t, 1H, J=1 Hz), 7.202 (d, 1H, J=11.5 Hz), 7.138 (t, 1H, J=9.5 Hz), 6.758 (dd, 1H, J=2, 4.5 Hz), 4.463 (t, 2H, J=6.5 Hz), 2.921 (s, 3H), 2.864 (m, 2H), 2.520 (s, 6H), 2.285 (t, 2H, J=6.5 Hz). LC-MS (m/z) 308 [M+1].

Example 39

Preparation of (4Z,7Z)-1-((Z)-(5-fluoro-2-oxoindolin-3-ylidene)methyl)-3-methylcyclohepta[c]pyrrol-6 (2H)-one (063)

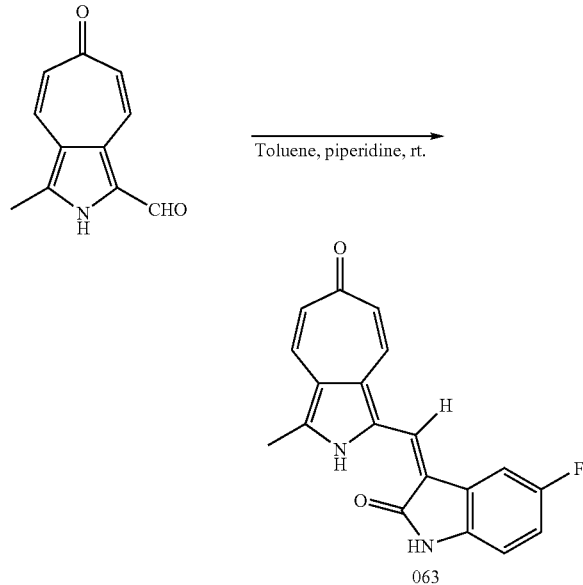

1.5 mg (3aZ,5Z,7Z)-methyl 3-formyl-2,4-dimethoxyazulene-1-carboxylate (0.007 mmol) was dissolved in 3 mL toluene. 2 mg oxindole (0.013 mmol) and 1 drop piperidine were then added and reacted at room temperature for one day. After removal of solvent, the result was extracted by dichloromethane and water. The organic layer was collected, dried with anhydrous magnesium sulfate, filtered, concentrated under vacuum, and purified by column chromatography (Silica Gel 60, methanol/dichloromethane=1/30) to give yellowish-brown Compound 063 (1.1 mg, 46%).

063 (500 MHz, Acetone-d$_6$) δ (ppm) 8.19 (s, 1H), 8.03 (d, J=11.5 Hz, 1H), 7.99 (s, 1H), 7.74 (d, J=10.0 Hz, 1H), 7.51 (d, J=11.5 Hz, 1H), 6.96-7.02 (m, 2H), 6.50 (dd, J=12.3, 2.0 Hz, 1H), 6.40 (dd, J=12.3, 2.0 Hz, 1H), 2.68 (s, 3H). LC-MS (m/z) 321 [M+1].

Example 40

Preparation of 3-(((4Z,6Z,8E)-2-aminoazulen-1-yl)methylene)-5-fluoroindolin-2-one (064)

Compound 064 was prepared in a manner similar to that described in Example 31. 15 mg (3aZ,5Z,7Z)-2-aminoazulene-1-carbaldehyde and 11.84 mg 5-fluoro-2-oxindole were reacted to give Compound 064 (E/Z form 1:3). LC-MS (m/z) 305 [M+1].

Example 41

Preparation of (3E)-5-fluoro-3-(((4Z,6Z,8Z)-1,3-dimethylazulen-2-yl)methylene)indolin-2-one (066)

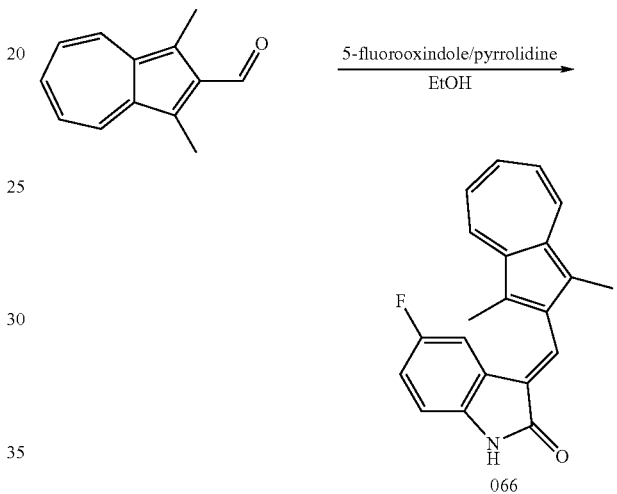

Compound 066 was prepared in a manner similar to that described in Example 1. The result was purified by column chromatography (Silica Gel 60, ether/n-hexane=5:1) and dried to give Compounds 066 (50 mg, 58%).

066 (500 MHz, DMSO-d$_6$) δ (ppm) 10.70 (s, 1H), 8.32 (d, J=9.5 Hz, 1H), 8.03 (s, 1H), 7.63 (t, J=10.0 Hz, 1H), 7.14 (t, J=9.5 Hz, 1H), 7.08 (t, J=9.5 Hz, 1H), 6.90-6.88 (m, 1H), 6.21 (d, 3.95 J=9.0 Hz, 1H), 5.76 (s, 3H), 2.49 (s, 6H). LC-MS (m/z) 318 [M+1].

Example 42

Preparation of 3-[4-(3-Dimethylamino-propoxy)-3-methyl-azulen-1-ylmethylene]-5-fluoro-1,3-dihydro-indol-2-one (068), (095)

17.6 mg (3aE,5Z,7Z)-4-(3-(dimethylamino)propoxy)-3-methylazulene-1-carbaldehyde, 24.5 mg 5-fluorooxindole, and 1-2 drops piperidine were added in dried ethanol with reflux for 12 hours. After removal of ethanol, ethyl acetate and water were added. A small quantity of hydrochloric acid was then added to acidify the solution to about pH 1-2. The solution was alkalized again, then the organic layer was collected, dried with magnesium sulfate, filtered and concentrated under vacuum, the results were purified by silica gel column chromatography (100% methanol) to give Compounds 068 and 095 (9.9 mg).

068 $^1$H-NMR (500 MHz, CDCl$_3$) δ (ppm) 8.61 (b, 1H), 8.46 (d, J=10 Hz, 1H), 8.36 (s, 1H). 8.01 (s, 1H), 7.74 (d, 1H), 7.53 (t, J=5 Hz, 1H), 7.02~6.83 (m, 4H), 4.36 (t, J=5 Hz, 2H), 2.87 (s, 3H), 2.56 (t, J=5 Hz, 2H), 2.30 (s, 6H), 2.17 (m, 2H); 095 $^1$H-NMR (500 MHz, DMSO-d$_6$) δ (ppm) 10.43 (s, 1H), 9.34 (s, 1H), 9.06 (d, J=10 Hz, 1H), 8.34 (s, 1H), 7.91 (d, 1H), 7.7 (t, J=10 Hz, 1H), 7.29 (d, 2H), 7.21 (t, 1H), 6.94 (m, 1H), 6.80 (m, 1H), 4.42 (t, J=5 Hz, 2H), 2.83 (s, H), 2.50 (t, 2H), 2.21 (s, 6H), 2.08 (m, 2H). LC-MS (m/z) 405 [M+1].

Example 43

Preparation of (3aZ,5Z,7Z)-methyl-3-((Z)-(5-fluoro-2-oxoindolin-3-ylidene)methyl)-2,4-dimethoxyazulene-1-carboxylate (069)

21.8 mg (3aZ,5Z,7Z)-methyl 3-formyl-2,4-dimethoxyazulene-1-carboxylate (0.08 mmol) was dissolved in 8 mL methanol. 12 mg oxindole (0.08 mmol) and 2 drops pyrrolidine (2M/in methanol) were then added with reflux for 3 hours. After removal of solvent, the result was extracted by dichloromethane and water. The organic layer was collected, dried with anhydrous magnesium sulfate, filtered, concentrated under vacuum, and purified by column chromatography (Silica Gel 60, acetyl acetate/n-hexane=3/1) to give yellowish-brown Compound 069 (7.1 mg, 22%).

069 (500 MHz, CDCl$_3$) δ (ppm) 9.37 (d, J=10.0 Hz, 1H), 8.45 (s, 1H), 7.83 (s, 1H), 7.65 (t, J=10.0 Hz, 1H), 7.36 (t, J=10.0 Hz, 1H), 7.12 (d, J=11.0 Hz, 1H), 6.82 (td, J=8.8, 2.0 Hz, 1H), 6.74 (dd, J=11.0, 4.5 Hz, 1H), 6.60 (dd, J=9.25, 3.0 Hz, 1H), 3.98 (s, 3H), 3.96 (s, 1H), 3.88 (s, 1H). LC-MS (m/z) 408 [M+1].

Example 44

Preparation of (3aZ,5Z,7Z)-methyl 3-((Z)-(5-fluoro-2-oxoindolin-3-ylidene)methyl)azulene-1-carboxylate (076)

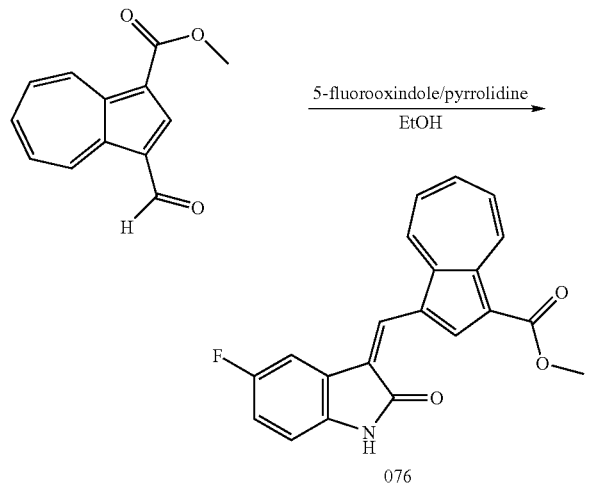

3960 mg (3aE,5Z,7Z)-methyl 3-formylazulene-1-carboxylate (18.5 mmol) was dissolved in 200 mL acetic acid. 3325 mg 5-fluorooxindole (22 mmol) and 50 mg zinc acetate were then added with reflux at 90° C. for 12 hours until the reaction was completed. After cooling to room temperature and removal of solvent, 50 mL ethyl acetate was added and ultrasonically shaken for 10 min. The filtered result was then washed by ethyl acetate and dried to give Compound 076.

076 (500 MHz, DMSO-d$_6$) δ (ppm) 10.63 (s, 1H), 9.67 (d, J=10.0 Hz, 1H), 8.84 (d, J=10.0 Hz, 1H), 8.81 (s, 1H), 8.22 (d, J=10.0 Hz, 1H), 8.20 (s, 1H), 7.95 (t, J=9.5 Hz, 1H), 7.86 (t, J=10.0 Hz, 1H), 7.30 (d, J=9.0 Hz, 1H), 7.11 (t, J=8.0 Hz, 1H), 6.942-6.917 (m, 1H), 3.95 (s, 3H). LC-MS (m/z) 348 [M+1].

Example 45

Preparation of 4-{3-[4-(3-Dimethylamino-propoxy)-3-methyl-azulen-1-ylmethylene]-2-oxo-2,3-dihydro-1H-indol-5-ylamino}-piperidine-1-carboxylic acid ethyl ester (085)

3.5 mg (3aE,5Z,7Z)-4-(3-(dimethylamino)propoxy)-3-methylazulene-1-carbaldehyde, 8 mg ethyl 4-(2-oxoindolin-5-ylamino)piperidine-1-carboxylate, and 1-2 drops piperidine were added in dried ethanol with reflux for 12 hours. After removal of ethanol, ethyl acetate and water were added. After removal of ethyl acetate, the result was purified by silica gel column chromatography (100% methanol) to give Compounds 085 (1.4 mg, E/Z=2:1).

085 (E-form) (500 MHz, CDCl$_3$) δ (ppm) 8.43 (d, J=10 Hz, 1H), 8.02 (s, 1H), 6.85~7.65 (m, 4H), 6.7 (d, 1H), 6.43 (d, 1H), 4.37 (t, 2H), 4.1 (q, 3H), 2.85 (s, 3H), 2.65 (t, 2H), 1.99~2.6 (m, 10H), 1.27 (t, 3H), 1.16 (t, 3H), 0.89 (m, 2H), 0.99 (m, 2H). LC-MS (m/z) 557 [M+1].

Example 46

Preparation of 4-{3-[4-(3-Dimethylamino-propoxy)-3-methyl-azulen-1-ylmethylene]-2-oxo-2,3-dihydro-1H-indol-5-ylamino}-piperidine-1-carboxylic acid ethyl ester (086)

3.8 mg (3aE,5Z,7Z)-4-(3-(dimethylamino)propoxy)-3-methylazulene-1-carbaldehyde and 2-fold mole 5-(1-ethylpiperidin-4-ylamino)indolin-2-one were reacted by a manner similar to that described in Example 45 to give Compounds 086 (35%, E/Z=8:1).

086 (E-form) (500 MHz, CDCl$_3$) δ (ppm) 8.425 (d, J=9.5 Hz, 1H), 8.248 (s, 1H), 8.028 (s, 1H), 7.505 (t, J=10 Hz, 2H), 7.352 (d, J=13 Hz, 3H), 7.029-6.885 (m, 6H), 6.664 (t, J=8.0 Hz, 2H), 4.37 (t, 2H), 2.85 (s, 3H), 2.59 (m, 1H), 2.3~2.55 (m, 13H), 1.55 (m, 4H), 1.16 (t, 3H). LC-MS (m/z) 513 [M+1].

Example 47

Preparation of 3-(((4Z,6Z,8E)-8-(3-morpholinopropoxy)-1-methylazulen-3-yl)methylene)-5-fluoroindolin-2-one (087)

1.7 mg (3aE,5Z,7Z)-4-(3-morpholinopropoxy)-3-methylazulene-1-carbaldehyde (0.005 mmol) was dissolved in 4 mL ethanol. 3.7 mg 5-fluorooxindole (0.025 mmol) and 2 drops piperidine were then added with reflux for 3.5 hours. After removal of solvent, the result was extracted by dichloromethane and water. The organic layer was collected, dried with anhydrous magnesium sulfate, filtered, concentrated under vacuum, and purified by column chromatography (Silica Gel 60, methanol/dichloromethane=1/30) to give yellowish-brown Compound 087 (2.3 mg, 95%, E/Z 3:1).

087 (500 MHz, CDCl$_3$) δ (ppm) 9.29 (s, 1H), 8.43 (d, J=10.5 Hz, 1H), 8.30 (s, 1H), 7.99 (s, 1H), 7.71 (d, J=8.5 Hz, 1H), 7.52 (dd, J=10.5, 8.5 Hz, 1H), 6.96-7.10 (m, 2H), 6.73-6.81 (m, 1H), 4.35-4.42 (m, 2H), 3.70-3.85 (m, 4H), 2.72 (s, 3H), 2.50-2.80 (m, 6H), 2.15-2.30 (m, 2H). LC-MS (m/z) 447 [M+1].

Example 48

Preparation of 3-[4-(3-Dimethylamino-propoxy)-3-methyl-azulen-1-ylmethylene]-2-oxo-2,3-dihydro-1H-indole-5-sulfonic acid methylamide (088)

6 mg (3aE,5Z,7Z)-4-(3-(dimethylamino)propoxy)-3-methylazulene-1-carbaldehyde and 10 mg 5-(N-methylsulfonyl)indolin-2-one were reacted by a manner similar to that described in Example 45 to give Compound 088 (6 mg).

088 (500 MHz, CDCl$_3$) δ (ppm) 8.50 (s, 1H), 8.39 (d, J=9.5 Hz, 1H), 8.32 (s, 1H), 8.00 (s, 1H), 7.68 (d, J=7 Hz, 1H), 7.49 (t, J=10.5 Hz, 1H), 6.94~6.98 (m, 3H), 4.29~4.32 (m, 2H), 2.79 (s, 3H), 2.65 (s, 3H), 2.51~2.55 (m, 2H), 2.27 (s, 6H), 2.09~2.13 (m, 2H). LC-MS (m/z) 480 [M+1].

Example 49

Preparation of 3-(((3aZ,5Z,7E)-8-(3-(diethylamino)propoxy)-1-methylazulen-3-yl)methylene)-5-fluoroindolin-2-one (090)

(3aE,5Z,7Z)-4-(3-(dimethylamino)propoxy)-3-methylazulene-1-carbaldehyde was replaced by (4E,6Z,8E)-4-(3-(diethylamino)propoxy)-3-methylazulene-1-carbaldehyde. Compound 090 was prepared in a manner similar to that described in Example 42 with a yield of 40-50%.

090 (E-form) (500 MHz, CDCl$_3$) δ (ppm) 8.48 (d, J=10 Hz, 1H), 8.28 (s, 1H), 8.24 (b, 1H), 8.06 (s, 1H), 7.26 (d, 1H), 6.89 (t, 1H), 6.77-6.88 (m, 3H), 4.35 (t, 2H), 2.88 (s, 3H), 2.71 (d, 2H), 2.62 (t, 4H), 2.16 (q, 2H), 1.04 (t, 6H). (Z-form) 9.33 (s, 1H), 8.43 (d, J=10 Hz, 1H), 8.23 (b, 1H), 7.76 (d, 1H), 7.53 (m, 1H), 7.01 (t, 1H), 6.77-6.90 (m, 3H), 4.34 (t, 2H), 2.88 (s, 3H), 2.71 (d, 2H), 2.59 (t, 4H), 2.18 (q, 2H), 1.05 (t, 6H). LC-MS (m/z) 433 [M+1].

Example 50

Preparation of 3-(((4Z,6Z,8E)-8-(3-(4-methylpiperazin-1-yl)propoxy)-1-methylazulen-3-yl)methylene)-5-fluoroindolin-2-one (096)

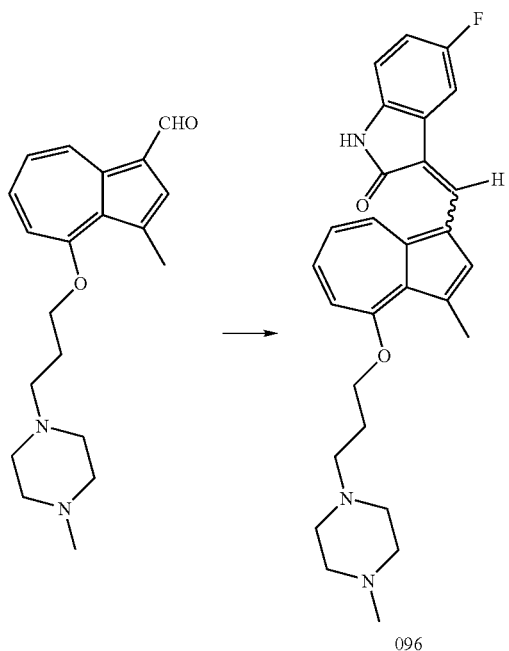

096

0.6 mg (3aE,5Z,7Z)-4-(3-(4-methylpiperazin-1-yl)propoxy)-3-methylazulene-1-carbaldehyde (0.002 mmol) was dissolved in 3 mL toluene. 3.5 mg 5-fluorooxindole (0.023 mmol) and 6 drops piperidine were then added and reacted at room temperature for two days. After removal of solvent, the result was extracted by dichloromethane and water. The organic layer was collected, dried with anhydrous magnesium sulfate, filtered, concentrated under vacuum, and purified by column chromatography (Silica Gel 60, methanol/dichloromethane=1/20) to give yellowish-brown Compound 096 (0.76 mg, 90%, E/Z 1.7:1).

096 (500 MHz, CDCl$_3$) δ (ppm) 9.31 (s, 1H), 8.45 (d, J=10.0 Hz, 1H), 8.33 (s, 1H), 8.00 (s, 1H), 7.72 (dd, J=9.5, 2.5 Hz, 1H), 7.53-7.58 (m, 2H), 6.94-7.40 (m, 2H), 6.72-6.80 (m, 1H), 4.30-4.40 (m, 2H), 2.73 (s, 3H), 2.70-2.80 (m, 4H), 2.45-2.50 (m, 2H), 2.16-2.25 (m, 2H). LC-MS (m/z) 460 [M+1].

Example 51

Preparation of 4-{3-[4-(3-Dimethylamino-propoxy)-3-methyl-azulen-1-ylmethylene]-2-oxo-2,3-dihydro-1H-indol-6-ylamino}-piperidine-1-carboxylic acid ethyl ester (097)

Compound 097 was prepared in a manner similar to that described in Example 45.

097 (500 MHz, CD$_3$OD) 8.443 (d, J=9.5 Hz, 1H), 8.028 (s, 1H), 7.975 (s, 1H), 7.764 (d, J=8.5 Hz, 1H), 7.633 (t, J=10.5 Hz, 1H), 7.111 (d, J=11 Hz, 1H), 7.030 (t, J=9.5 Hz, 1H), 6.339-6.294 (m, 2H), 4.438 (t, J=6.0 Hz, 2H), 4.193-4.105 (m, 4H), 3.398 (s, 3H), 2.923 (s, 3H), 2.697 (t, J=7.0 Hz, 2H), 2.370 (s, 6H), 2.253-2.199 (m, 2H), 2.073 (d, J=12 Hz, 2H), 1.938 (s, 4H), 1.460-1.297 (m, 8H). LC-MS (m/z) 557 [M+1].

Example 52

Preparation of 3-[4-(3-Dimethylamino-propoxy)-3-methyl-azulen-1-ylmethylene]-1,3-dihydro-indol-2-one (098)

6 mg (3aE,5Z,7Z)-4-(3-(dimethylamino)propoxy)-3-methylazulene-1-carbaldehyde and 3 mg 2-oxindole were reacted by a manner similar to that described in Example 45 to give Compound 098 (4 mg, E/Z 5.6:1).

098 (500 MHz, CDCl$_3$) δ (ppm) 8.47 (d, J=9 Hz, 1H), 8.33 (s, 1H), 8.08 (s, 1H), 8.03 (d, J=7.5 Hz, 1H), 7.46~7.54 (m, 1H), 7.19 (t, J=10.5 Hz, 1H), 6.90~6.98 (m, 4H), 4.37~4.35 (m, 2H), 2.88 (s, 3H), 2.57~2.60 (m, 2H), 2.31 (s, 6H), 2.15~2.18 (m, 2H). LC-MS (m/z) 387 [M+1].

Example 53

Preparation of 3-[4-(3-Dimethylamino-propoxy)-3-methyl-azulen-1-ylmethylene]-7-fluoro-1,3-dihydro-indol-2-one (099)

7 mg (3aE,5Z,7Z)-4-(3-(dimethylamino)propoxy)-3-methylazulene-1-carbaldehyde and 10 mg 7-Fluoro-2-oxindole were reacted by a manner similar to that described in Example 45 to give Compound 099 (4 mg, E/Z 2.3:1).

099 (500 MHz, CDCl$_3$) δ (ppm) 8.48 (d, J=9.5 Hz, 1H), 8.37 (s, 1H), 8.06 (s, 1H), 7.83 (d, J=9 Hz, 1H), 7.53~7.55 (m, 1H), 6.95~7.06 (m, 2H), 6.89~6.92 (m, 2H), 4.34~4.38 (m, 2H), 2.88 (s, 3H), 2.55~2.580 (m, 2H), 2.30 (s, 6H), 2.14~2.19 (m, 2H). LC-MS (m/z) 405 [M+1].

Example 54

Preparation of 3-[4-(3-Dimethylamino-propoxy)-3-methyl-azulen-1-ylmethylene]-5-trifluoromethyl-1,3-dihydro-indol-2-one (100)

(3aE,5Z,7Z)-4-(3-(dimethylamino)propoxy)-3-methylazulene-1-carbaldehyde and 5-Trifluoromethyl-1,3-dihydroindol-2-one were reacted by a manner similar to that described in Example 45 to give Compound 100 (E/Z 2:1).

100 (500 MHz, CD$_3$OD) δ (ppm) 9.249 (s, 1H), 8.807 (d, J=9.5 Hz, 1H), 8.503 (d, J=10 Hz, 1H), 8.368 (s, 1H), 8.330 (s, 1H), 8.241 (s, 1H), 8.047 (s, 1H), 7.984 (s, 1H), 7.755-7.697 (m, 2H), 7.254 (d, J=8.0 Hz, 1H), 7.450 (d, J=7.5 Hz, 1H), 7.246-7.146 (m, 4H), 7.106 (d, J=8.0 Hz, 1H), 7.031 (d, J=8.5 Hz, 1H), 4.444 (t, J=6.0 Hz, 2H), 4.382 (t, J=6.0 Hz, 2H), 2.885 (s, 3H), 2.861 (s, 3H), 2.695-2.651 (m, 4H), 2.361 (d, J=2.5 Hz, 12H), 2.242-2.166 (m, 4H). LC-MS (m/z) 455 [M+1].

Example 55

Preparation of 3-(((3aZ,5Z,7E)-8-(3-(dimethylamino)propoxy)-1-methylazulen-3-yl)methylene)-1H-pyrrolo[2,3-b]pyridin-2(3H)-one (104)

Compound 104 was prepared in a manner similar to that described in Example 45 (E/Z 3.3:1). LC-MS (m/z) 388 [M+1].

Biological Assays

Compounds 1-100 were treated for their efficacy in inhibiting activities of FLT-3, c-KIT, KDR/Flk-1, PDGFR-beta, EGFR, and PKC kinases by biochemical DELFIA (Dissociation Enhanced Lanthanide FIA) assays according to the procedure described below. The assays were conducted by, Division of Cell Engineering, Biomedical Engineering Research Laboratories, Industrial Technology Research Institute, Bldg. 53, 195, sec. 4, Chung Hsing Rd. Chutung, Hsinchu, Taiwan 310, R.O.C.

The FLT-3 assay was conducted following the protocol described in Protocol for HTScan® FLT-3 Kinase Assay Kit (Cell Signaling Technology®). The assay was conducted under the following conditions: FLT-3 source: The GST-kinase fusion protein was produced using a baculovirus expression system with a construct expressing human FLT-3 (Arg571-Ser993) (GenBank accession No. NM_004119) with an amino-terminal GST tag, substrate: 1.5 μM Gastrin Precursor Biotinylated Peptide (with Tyr87 as phosphorylation site), vehicle: 1% DMSO, pre-incubation time/temperature: 5 minutes at room temperature, incubation time/temperature: 30 minutes at room temperature, incubation buffer: 60 mM HEPES pH 7.5, 5 mM MgCl$_2$, 5 mM MnCl$_2$, 3 μM Na$_3$VO$_4$, 1.25 mM DTT, 20 μM ATP, and quantitative method: DELFIA® Assay.

The c-KIT assay was conducted following the protocol described in Protocol for HTScan® c-KIT Kinase Assay Kit (Cell Signaling Technology®). The assay was conducted under the following conditions: c-KIT source: The GST-c-KIT fusion protein was produced using a baculovirus expression system with a construct expressing human c-KIT (Thr544-Val976) with an amino-terminal GST tag, substrate: 1.5 μM This biotinylated peptide contains the residues surrounding Tyr-996 of KDR, vehicle: 1% DMSO, pre-incubation time/temperature: 5 minutes at room temperature, incubation time/temperature: 30 minutes at room temperature, incubation buffer: 60 mM HEPES pH 7.5, 5 mM MgCl$_2$, 5 mM MnCl$_2$, 3 μM Na$_3$VO$_4$, 1.25 mM DTT, 20 μM ATP, and quantitative method: DELFIA® Assay.

The KDR assay was conducted following the protocol described in Protocol for HTScan® VEGFR-2 Kinase Assay Kit (Cell Signaling Technology®). The assay was conducted under the following conditions: KDR source: The GST-Kinase fusion protein was produced using a baculovirus expression system with a construct expressing human VEGFR-2 (Val789-Val1356) (GenBank Accession No. NM_002253) with an amino-terminal GST tag, substrate: 1.5 μM Gastrin Precursor Biotinylated Peptide (with Tyr87 as phosphorylation site), vehicle: 1% DMSO, pre-incubation time/temperature: 5 minutes at room temperature, incubation time/temperature: 30 minutes at room temperature, incubation buffer: 60 mM HEPES pH 7.5, 5 mM MgCl$_2$, 5 mM MnCl$_2$, 3 μM Na$_3$VO$_4$, 1.25 mM DTT, 20 μM ATP, and quantitative method: DELFIA® Assay.

The EGFR assay was conducted following the protocol described in Protocol for HTScan® EGFR Kinase Assay Kit (Cell Signaling Technology®). The assay was conducted under the following conditions: EGFR source: The GST-kinase fusion protein was produced using a baculovirus expression system with a construct expressing human EGFR (His672-Ala1210) (GenBank Accession No. NM_005228) with an amino-terminal GST tag, substrate: 1.5 μM This biotinylated peptide contains the residues surrounding Tyr-66 of PTP1B, vehicle: 1% DMSO, pre-incubation time/temperature: 5 minutes at room temperature, incubation time/temperature: 30 minutes at room temperature, incubation buffer: 60 mM HEPES pH 7.5, 5 mM MgCl$_2$, 5 mM MnCl$_2$, 3 μM Na$_3$VO$_4$, 1.25 mM DTT, 20 μM ATP, and quantitative method: DELFIA® Assay.

The PDGFR-beta assay was conducted following the protocol described in Protocol for HTScan® PDGFR-beta Kinase Assay Kit (Cell Signaling Technology®). The assay was conducted under the following conditions: PDGFR-beta source: The GST-Kinase fusion protein was produced using a baculovirus expression system with a construct expressing human PDGFRβ (Gln557-Leu1106) (GenBank Accession No. NM_002609) with an amino-terminal GST tag, substrate: This biotinylated peptide contains the residues surrounding Tyr-589 of FLT-3, vehicle: 1% DMSO, pre-incubation time/temperature: 5 minutes at room temperature, incubation time/temperature: 30 minutes at room temperature, incubation buffer: 60 mM HEPES pH 7.5, 5 mM MgCl$_2$, 5 mM MnCl$_2$, 3 μM Na$_3$VO$_4$, 1.25 mM DTT, 20 μM ATP, and quantitative method: DELFIA® Assay.

The inhibitory effects of compounds 1-104 against kinases, FLT-3, c-KIT, KDR, EGFR, and PDGFR-beta, at 1 and 0.1 μM are summarized in the Table 2.

TABLE 2 the inhibitory activity of example against kinases (% of inhibition relative to control)

| Compound | c-KIT 1 μM | c-KIT 0.1 μM | FLT-3 1 μM | FLT-3 0.1 μM | KDR 1 μM | KDR 0.1 μM | EGFR 1 μM | EGFR 0.1 μM | PDGFR-β 10 μM |
|---|---|---|---|---|---|---|---|---|---|
| vehicle | 0.0 | 0.0 | 0.0 | 0.0 | 0.0 | 0.0 | | | 0.0 |
| 2 | 24.7 | 24.7 | — | — | 10.3 | — | | | 3.6 |
| 3 | — | — | 5.1 | — | — | — | | | 14.4 |
| 4 | — | — | 14.7 | — | — | — | | | — |
| 6 | 36.6 | 36.6 | — | — | 29.7 | 19.6 | | | 35.5 |
| 7 | 30.9 | 30.9 | 40.1 | 17.8 | 28.8 | 29.5 | | | 4.7 |
| 8 | 36.4 | 36.4 | 11.5 | — | 55.9 | 26.4 | | | 16.2 |
| 9 | 11.5 | 11.5 | 3.8 | — | 33.4 | 12.3 | | | 14.7 |
| 10 | 8.4 | 8.4 | — | — | 38.5 | 22.1 | | | 18.6 |
| 11 | 1.8 | 1.8 | 1.1 | — | 25.1 | 1.7 | | | 4.2 |
| 12 | 14.7 | 14.7 | — | — | 34.3 | 17.3 | | | 7.3 |
| 13 | 66.2 | 66.2 | 0.2 | 4.4 | 83.9 | 54.1 | | | — |
| 14 | 31.5 | 31.5 | 6.0 | — | 69.2 | 17.1 | | | — |
| 16 | 2.8 | 2.8 | — | 7.7 | 20.1 | 15.4 | | | 3.6 |
| 19 | 0.6 | 0.6 | 7.6 | — | 22.1 | 33.8 | | | — |
| 20 | 6.3 | 6.3 | 42.5 | 4.1 | 46.8 | 46.9 | | | 16.7 |
| 22 | 16.6 | 16.6 | 30.3 | 28.8 | 40.6 | 15.6 | | | 5.3 |
| 23 | — | — | 43.4 | 18.6 | 28.3 | 39.5 | | | — |
| 25 | 75.0 | 75.0 | 58.8 | 26.2 | 45.7 | 7.7 | | | — |
| 26 | 60.4 | 60.4 | 34.7 | 5.0 | 59.1 | 33.9 | | | 7.9 |
| 27 | 25.7 | 25.7 | 30.9 | 8.6 | 39.5 | 25.9 | | | 5.3 |
| 28 | 6.8 | 6.8 | 24.5 | 1.9 | 22.4 | — | | | |
| 29 | 46.1 | 46.1 | 53.3 | — | 48.2 | 18.5 | | | |
| 30 | 26.9 | 26.9 | 34.6 | 7.3 | 15.6 | 9.5 | | | |
| 31 | — | — | 14.9 | — | — | — | — | 0.2 | |
| 32 | 60.3 | 60.3 | 89.5 | 48.5 | 6.2 | — | 13.7 | 7.7 | |
| 33 | 63.1 | 63.1 | 85.6 | 50.5 | 50.8 | 24.6 | 13.0 | 15.2 | |
| 34 | — | — | 1.9 | 0.8 | 18.2 | 8.9 | 11.7 | 6.1 | |
| 35 | — | — | — | — | 20.3 | — | 12.1 | 9.5 | |
| 36 | 49.2 | 49.2 | 39.3 | — | 0.3 | — | 10.9 | 9.6 | |
| 37 | 53.2 | 53.2 | 61.5 | 5.9 | 27.6 | — | 13.6 | 2.9 | |
| 38 | 72.6 | 72.6 | 79.0 | 40.5 | 8.4 | 2.3 | 1.7 | 0.8 | |
| 39 | 80.1 | 80.1 | 93.2 | 45.6 | 20.2 | — | 14.1 | 6.1 | |
| 40 | 80.0 | 80.0 | 95.5 | 84.3 | 22.2 | 13.8 | 17.3 | 10.0 | |
| 41 | 76.6 | 76.6 | 87.6 | 74.7 | 30.4 | 25.2 | 9.4 | 6.4 | |
| 42 | 8.3 | 8.3 | 24.3 | 8.9 | 13.6 | 6.0 | 10.8 | 8.8 | |
| 43 | 14.7 | 14.7 | 24.3 | — | 6.8 | — | 11.9 | 6.2 | |
| 44 | 7.2 | 7.2 | 8.2 | 5.7 | 38.4 | — | 9.3 | 4.7 | |
| 45 | 73.9 | 73.9 | 69.7 | 51.4 | 41.9 | 32.8 | — | 2.5 | |
| 46 | 70.9 | 70.9 | 73.5 | 45.9 | 33.2 | 10.0 | 18.5 | 11.0 | |
| 47 | 30.7 | 30.7 | 48.6 | 0.5 | 34.0 | 7.8 | 14.6 | 8.3 | |
| 48 | 32.2 | 32.2 | 61.6 | 4.5 | 13.8 | — | 10.4 | 7.8 | |
| 50 | 19.5 | 19.5 | 29.6 | 4.0 | 25.8 | 22.3 | 10.4 | 7.9 | |
| 51 | 73.9 | 73.9 | 82.6 | 38.4 | 26.4 | — | 11.5 | — | |
| 52 | 20.2 | 20.2 | 44.2 | 14.1 | 9.1 | 12.6 | | | |
| 53 | 39.8 | 39.8 | 52.7 | 30.6 | 20.1 | 16.3 | | | |
| 54 | 27.5 | 27.5 | 52.5 | 33.3 | 25.7 | 17.0 | | | |
| 55 | 36.1 | 36.1 | 53.0 | 35.4 | 38.4 | 33.7 | | | |
| 56 | 34.8 | 34.8 | 53.0 | 12.6 | 34.2 | 35.4 | | | |
| 58 | 18.0 | 18.0 | 43.9 | 16.5 | 23.8 | 12.1 | | | |
| 59 | 24.2 | 24.2 | 49.8 | 43.0 | 28.5 | 19.9 | | | |
| 60 | 28.3 | 28.3 | 52.8 | 52.6 | 40.3 | 55.6 | | | |
| 61 | 30.5 | 30.5 | 42.5 | 62.5 | 52.6 | 44.2 | | | |
| 62 | 45.6 | 45.6 | 74.9 | 68.3 | 35.1 | 21.9 | | | |
| 63 | 57.1 | 57.1 | 55.7 | 50.5 | 32.2 | 6.7 | | | |
| 64 | 34.2 | 34.2 | 74.9 | 68.3 | 47.8 | 46.5 | | | |
| 65 | 51.3 | 51.3 | 30.9 | 23.3 | 46.9 | 46.8 | | | |
| 66 | 33.7 | 33.7 | 19.6 | 15.8 | 40.6 | 14.8 | | | |
| 67 | 30.2 | 30.2 | 14.0 | — | 7.4 | — | | | |
| 68 | 34.4 | 34.4 | 96.8 | 74.3 | 63.8 | 38.6 | | | |
| 69 | — | — | — | 17.2 | 42.5 | 32.9 | | | |
| 73 | — | — | 32.8 | 33.9 | 52.4 | 40.4 | | | |
| 74 | — | — | 69.4 | 45.8 | 70.9 | 5.1 | | | |
| 76 | 28.2 | 28.2 | — | — | — | — | | | |
| 77 | 23.4 | 23.4 | — | — | — | — | | | |
| 80 | 29.6 | 29.6 | 19.7 | 17.6 | 32.0 | 30.2 | | | |
| 81 | 48.7 | 48.7 | 43.5 | 19.1 | 36.6 | 33.0 | | | |
| 82 | 30.7 | 30.7 | 13.5 | 12.8 | 18.5 | 17.6 | | | |
| 83 | 19.6 | 19.6 | 17.7 | 10.5 | 26.7 | 20.8 | | | |
| 84 | 20.1 | 20.1 | 31.6 | 30.1 | 10.4 | 22.4 | | | |
| 85 | 2.4 | 2.4 | 2.0 | — | 4.4 | — | | | |
| 86 | 9.5 | 9.5 | 36.8 | 30.3 | 11.4 | 5.3 | | | |
| 87 | 71.0 | 71.0 | 85.7 | 56.9 | 11.5 | 1.9 | | | |

TABLE 2-continued the inhibitory activity of example against kinases (% of inhibition relative to control)

| | c-KIT | | FLT-3 | | KDR | | EGFR | | PDGFR-β |
|---|---|---|---|---|---|---|---|---|---|
| Compound | 1 μM | 0.1 μM | 1 μM | 0.1 μM | 1 μM | 0.1 μM | 1 μM | 0.1 μM | 10 μM |
| 88 | 19.3 | 19.3 | 47.3 | 24.2 | 16.8 | — | | | |
| 90 | 83.2 | 83.2 | 85.5 | 33.9 | 32.8 | — | | | |
| 91 | 56.5 | 56.5 | 52.4 | 15.2 | 9.4 | 1.1 | | | |
| 93 | — | — | 29.3 | 6.8 | 9.3 | — | | | |
| 94 | 47.6 | 47.6 | 14.4 | 6.5 | 52.4 | 35.8 | | | |
| 95 | 65.1 | 65.1 | 98.4 | 70.9 | 93.6 | 35.5 | | | |
| 96 | 58.0 | 58.0 | 97.2 | 68.9 | 89.8 | 29.3 | | | |
| 97 | 30.6 | 30.6 | 23.9 | 19.1 | 41.8 | 30.5 | | | |
| 98 | 60.4 | 60.4 | 85.4 | 46.1 | 80.3 | 38.6 | | | |
| 99 | 34.4 | 34.4 | 59.4 | 7.3 | 73.9 | 28.7 | | | |
| 100 | 48.1 | 48.1 | 89.1 | 64.9 | 73.2 | 33.3 | | | |
| 104 | 57.4 | 42.5 | 44.8 | 14.6 | 88.0 | 30.1 | | | |

The concentration of a compound demonstrated 50% inhibition ($IC_{50}$) on tyrosine kinase activity of Compounds 39, 41, 68, 87, 90, and 95, are summarized in the Table 3.

TABLE 3 kinase inhibition ($IC_{50}$) of Compounds

| Compounds | FLT-3 (nM) | c-KIT (nM) | KDR (nM) |
|---|---|---|---|
| 039 | 491.4 | 128.5 | 6380 |
| 041 | 43.4 | 6.0 | — |
| 068 | 25.3 | >1000 | 500 |
| 087 | 4.8 | 17.8 | — |
| 090 | 10.1 | 77.9 | — |
| 095 | 9.3 | 158.4 | — |

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An azulene compound having following formula (I):

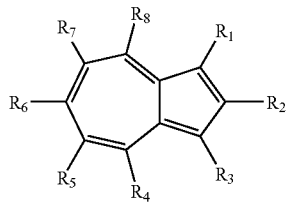

(I)

wherein one of $R_1$, $R_2$ and $R_3$ represents a moiety of formula (II):

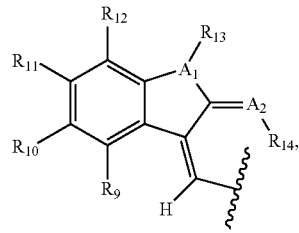

(II)

each of $A_1$ and $A_2$ independently is nitrogen, oxygen or sulfur;

each of the others of $R_1$, $R_2$, $R_3$, $R_4$, $R_5$, $R_6$, $R_7$ and $R_8$ independently is H, halo, $C_1$-$C_2$ alkyl, $C_4$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, $NO_2$, NO, $N_3$, SCN, CN, OCN, OR, OC(O)R, OC(S)R, OC(S)OR, OC(O), OC(S)SR, OC(O)NRR', OC(S)NRR', ONRR', OS(O)R, OS(O)$_2$R, SR, SC(O)R, SC(S)R, SC(S)OR, SC(O)SR, SC(S)SR, SC(O)NRR', SC(S)NRR', S(O)R, S(O)$_2$R, S(O)NRR', S(O)$_2$NRR', S(O)OR, S(O)$_2$OR, NCO, NCS, NRR', N(R)—C(O)R', N(R)—C(O)OR, N(R)—C(S)R', N(R)—C(S)OR, N(C(O)R)—C(O)R', N(R)—S(O)R', N(R)—S(O)OR, N(R)—S(O)$_2$R', N(R)—S(O)$_2$OR', N(R)—OR, N(OR)—C(O)R', N(OR)—C(O)OR, N(OR)—C(S)R', N(OR)—C(S)OR', N(OR)—C(S)SR', N(OR)—S(O)R', N(OR)—S(O)OR', N(OR)—S(O)$_2$R', N(OR)—S(O)$_2$OR', C(O)R, C(O)OR, C(O)NRR', C(O)SR, C(S)R, C(S)OR, C(S)NRR', C(S)SR, C(NR)—R', C(NR)—OR, C(NR)—NR'R", C(NR)—SR', C(NOR)—R', C(NOR)—OR', C(NOR)—NR'R", and C(NOR)—SR'; or $R_1$ and $R_2$, $R_2$ and $R_3$, $R_1$ and $R_5$, $R_5$ and $R_6$, $R_6$ and $R_7$, or $R_7$ and $R_8$, together with the atoms to which they are attached, are $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_3$-$C_{20}$ aryl, or $C_1$-$C_{20}$ heteroaryl; and each of $R_9$, $R_{10}$, $R_{11}$, $R_{12}$, $R_{13}$, and $R_{14}$ independently is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, $NO_2$, NO, $N_3$, SCN, CN, OCN, OR, OC(O)R, OC(S)R, OC(S)OR, OC(O)SR, OC(S)SR, OC(O)NRR', OC(S)

NRR', ONRR', OS(O)R, OS(O)$_2$R, SR, SC(O)R, SC(S)R, SC(S)OR, SC(O)SR, SC(S)SR, SC(O)NRR', SC(S)NRR', S(O)R, S(O)$_2$R, S(O)NRR', S(O)$_2$NRR', S(O)OR, S(O)$_2$OR, NCO, NCS, NRR', N(R)—C(O)R', N(R)—C(O)OR', N(R)—C(S)R', N(R)—C(S)OR', N(C(O)R)—C(O)R', N(R)—S(O)R', N(R)—S(O)OR', N(R)—S(O)$_2$R', N(R)—S(O)$_2$OR', N(R)—OR', N(OR)—C(O)R', N(OR)—C(O)OR', N(OR)—C(S)R', N(OR)—C(S)OR', N(OR)—C(S)SR', N(OR)—S(O)R', N(OR)—S(O)OR', N(OR)—S(O)$_2$R', N(OR)—S(O)$_2$OR', C(O)R, C(O)OR, C(O)NRR', C(O)SR, C(S)R, C(S)OR, C(S)NRR', C(S)SR, C(NR)—R', C(NR)—OR', C(NR)—NR'R", C(NR)—SR', C(NOR)—R', C(NOR)—OR', C(NOR)—NR'R", and C(NOR)—SR', each of $R_{13}$ and $R_{14}$ independently is deleted if the atom to which they are attached is oxygen or sulfur, in which each of R, R', and R" independently is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_3$-$C_{20}$ aryl, or $C_1$-$C_{20}$ heteroaryl, or R and R' or R' and R", together with the atom to which they are attached, are $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_3$-$C_{20}$ aryl, or $C_1$-$C_{20}$ heteroaryl, and with the proviso that the compound in which $A_1$ is nitrogen, $A_2$ is oxygen, $R_1$ is formula (II), $R_2$, $R_4$, $R_6$, $R_7$, $R_9$, $R_{10}$, $R_{11}$, $R_{12}$, and $R_{13}$ are H, $R_3$ and $R_8$ are methyl, $R_{14}$ is deleted, and $R_5$ is isopropyl is excluded wherein the alkyl, alkenyl, alkynyl, cycloalkyl, cycloalkenyl, heterocycloalkyl, heterocycloalkenyl, aryl and heteroaryl are substituted or unsubstituted.

2. The azulene compound as claimed in claim 1, wherein $A_1$ is nitrogen, $R_{13}$ is H or $C_1$-$C_{10}$ alkyl substituted with aryl.

3. The azulene compound as claimed in claim 1, wherein formula (I) is prepared by reaction of an azulene aldehyde with an indoline-2-one compound.

4. The azulene compound as claimed in claim 2, wherein $A_2$ is oxygen and $R_{14}$ is deleted.

5. The azulene compound as claimed in claim 4, wherein each of $R_9$, $R_{10}$, $R_{11}$, and $R_{12}$ independently is H, halo, $CF_3$, $C1$-$C_{10}$ alkyl, aryl, OR, $NO_2$, $S(O)_2$NRR', NRR'.

6. The azulene compound as claimed in claim 5, wherein each of $R_9$, $R_{10}$, $R_{11}$, and $R_{12}$ independently is H, F, Cl, Br, $CF_3$, $CH_3$, phenyl, $OCH_3$, $NO_2$, or $S(O)_2N(CH_3)_2$.

7. The azulene compound as claimed in claim 6, wherein each of the others of $R_1$, $R_2$, $R_3$, $R_4$, $R_5$, $R_6$, $R_7$, and $R_8$ independently is H, halo, $C_1$-$C_2$ alkyl, OR, NRR', or C(O)OR.

8. The azulene compound as claimed in claim 7, wherein each of the others of $R_1$, $R_2$, $R_3$, $R_4$, $R_5$, $R_6$, $R_7$, and $R_8$ independently is H, F, Cl, Br, $CH_3$, $CH_2CH_3$, $CH(CH_3)_2$, $O(CH_2)_{1-4}NR_1R_2$, $N(CH_2)_{1-2}NR_1R_2$, or $COOCH_3$.

* * * * *